US011932664B2

(12) United States Patent
Slusher et al.

(10) Patent No.: US 11,932,664 B2
(45) Date of Patent: *Mar. 19, 2024

(54) PRODRUGS OF PROSTATE SPECIFIC MEMBRANE ANTIGEN (PSMA) INHIBITOR

(71) Applicants: THE JOHNS HOPKINS UNIVERSITY, Baltimore, MD (US); INSTITUTE OF ORGANIC CHEMISTRY AND BIOCHEMISTRY AS CR v.v.i., Prague (CZ)

(72) Inventors: Barbara Slusher, Kingsville, MD (US); Rana Rais, Kingsville, MD (US); Marcela Krecmerova, Prague (CZ); Tomas Tichy, Prague (CZ); Pavel Majer, Sykesville, MD (US); Andrej Jancarik, Koprivnice (CZ)

(73) Assignees: THE JOHNS HOPKINS UNIVERSTY, Baltimore, MD (US); INSTITUTE OF ORGANIC CHEMISTRY AND BIOCHEMISTRY AS CR V.V.I., Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/739,669

(22) Filed: May 9, 2022

(65) Prior Publication Data

US 2023/0115651 A1 Apr. 13, 2023

Related U.S. Application Data

(60) Continuation of application No. 16/751,556, filed on Jan. 24, 2020, now Pat. No. 11,325,931, which is a division of application No. 15/968,074, filed on May 1, 2018, now Pat. No. 10,544,176, which is a division of application No. 15/502,105, filed as application No. PCT/US2015/044053 on Aug. 6, 2015, now Pat. No. 9,988,407.

(60) Provisional application No. 62/033,926, filed on Aug. 6, 2014.

(51) Int. Cl.
*C07F 9/6558* (2006.01)
*C07F 9/38* (2006.01)
*C07F 9/40* (2006.01)
*C07F 9/44* (2006.01)

(52) U.S. Cl.
CPC ........ *C07F 9/65586* (2013.01); *C07F 9/3808* (2013.01); *C07F 9/4006* (2013.01); *C07F 9/4075* (2013.01); *C07F 9/4084* (2013.01); *C07F 9/4087* (2013.01); *C07F 9/4465* (2013.01)

(58) Field of Classification Search
CPC ............. C07F 9/65586; C07F 9/3808
See application file for complete search history.

(56) References Cited

U.S. PATENT DOCUMENTS

| 6,071,965 | A | 6/2000 | Jackson et al. |
| 9,988,407 | B2 | 6/2018 | Slusher et al. |
| 10,544,176 | B2 | 1/2020 | Slusher et al. |
| 10,849,915 | B2 * | 12/2020 | Slusher ................ A61K 9/0053 |
| 11,325,931 | B2 * | 5/2022 | Slusher .................. A61P 25/28 |
| 2003/0194400 | A1 | 10/2003 | Liu et al. |
| 2006/0046978 | A1 | 3/2006 | Pierau et al. |
| 2011/0200677 | A1 | 8/2011 | Chandran et al. |
| 2018/0244705 | A1 | 8/2018 | Slusher et al. |

FOREIGN PATENT DOCUMENTS

WO WO 2016/022827 2/2016

OTHER PUBLICATIONS

Alex, P. et al. Clc-5 Knockout mice exhibit novel immunomodulatory effects and are more susceptible to dextran sulphate sodium induced colitis. J. Immunol. 2010, 184:3988-3996.

Alex, P., et al. Distinct cytokine patterns identified from multiplex profiles of murine DSS and TNBS-induced colitis. Inflamm. Bowel Dis. 2009, 15:341-352.

Baker et al., Dendrimer-based compositions in disease diagnosis and therapy. Chemical Abstracts Service. 2009. Accession No. 2009:53865, 2 pages.

Barditch-Crovo, P. et al. Phase i/ii trial of the pharmacokinetics, safety, and antiretroviral activity of tenofovir disoproxil fumarate in human immunodeficiency virus-infected adults. Antimicrob. Agents Chemother. 2001, 45:2733-2739.

Barditch-Crovo, P., et al. Anti-human immunodeficiency virus (HIV) activity, safety, and pharmacokinetics of adefovir dipivoxil (9-[2-(bis-pivaloyloxymethyl)phosphonylmethoxyethyl] adenine) in RN-infected patients. J. Infect. Dis. 1997, 176:406-413.

Barinka, et al., Glutamate Carboxypeptidase II in Diagnosis and Treatment of Neurologic Disorders and Prostate Cancer. Curr Med Chem. 2012; 19(6): 856-870.

Calabrese M., et al., Cortical lesions and atrophy associated with cognitive impairment in relapsing-remitting multiple sclerosis. Arch Neurol, 2009.66(9): p. 1144-50.

Colombel, J.F., et al. Adalimumab for maintenance of clinical response and remission in patients with Crohn's disease: the CHARM trial. Gastroenterology 2007, 132:52-65.

Cundy K.C., et al. Oral formulations of adefovir dipivoxil: in vitro dissolution and in vivo bioavailability in dogs. J. Pharm. Sci. 1997, 86:1334-1338.

Deeks, S.G., et al., The safety and efficacy of adefovir dipivoxil, a novel anti-human immunodeficiency virus (HIV) therapy, in HIV-infected adults: a randomized, double-blind, placebo-controlled trial. Jinfect Dis, 1997. 176(6): p. 1517-23.

(Continued)

Primary Examiner — Golam M Shameem
(74) Attorney, Agent, or Firm — Casimir Jones, SC; Jeffrey W. Childers

(57) ABSTRACT

Methods and compounds are disclosed for treating a disease or condition by inhibiting PSMA (Prostate Specific Membrane Antigen) using prodrugs of 2-PMPA.

9 Claims, 29 Drawing Sheets

(56) References Cited

OTHER PUBLICATIONS

Ding et al., Design and synthesis of a siderophore conjugate as a potent PSMA inhibitor and potential diagnostic agent for prostate cancer. Bioorg Med Chem. Feb. 15, 2008;16(4):1648-57.

Dutta, R. et al. Pathogenesis of axonal and neuronal damage in multiple sclerosis. Neurology, 2007. 68(22 Suppl 3): p. S22-31; discussion S43-54.

Egan M.F., et al., Variation in GRM3 affects cognition, prefrontal glutamate, and risk for schizophrenia. Proc Natl Acad Sci US A, 2004. 101(34): p. 12604-9.

Ginsburg et al., Addition of trialkyl phosphites to acrylic systems. Chemical Abstracts Service. 1961. Accession No. 1961:136955. 2 pages.

Gurkoff, G.G., et al., NAAG peptidase inhibitor improves motor function and reduces cognitive dysfunction in a model of TB! with secondary hypoxia. Brain Res, 2013. 1515:p. 98-107.

Hamilton, M.J., et al. Update on biologic pathways in inflammatory bowel disease and their therapeutic relevance. J. Gastroenterol. 2012, 47:1-8.

Hanauer, S.B. et al. Maintenance infliximab for Crohn's disease: the Accent I randomised trial. Lancet 2002, 359:1541-1549.

Harrison P.J., et al., The group II metabotropic glutamate receptor 3 (mGluR3, mGlu3, GRM3): expression, function and involvement in schizophrenia. J Psychopharmacol, 2008. 22(3): p. 308-22.

Harsanyi et al., Synthesis of 2-phosphinoxidomethyl- and 2-phosphonomethyl glutaric acid derivatives. Chemical Abstracts Service. 2005. Accession No. 2005:1263876, 2 pages.

Harsanyi, Synthesis of 2-phosphinoxidomethyl- and 2-phosphonomethyl glutaric acid derivatives. (2005) 16(7): 562-565.

Jaarsma D., L. et al. N-acetylaspartate and Nacetylaspartylglutamate levels in Alzheimer's disease post-mortem brain tissue. J Neurol Sci, 1994. 127(2): p. 230-3.

Jablensky, A., et al., Polymorphisms associated with normal memory variation also affect memory impairment in schizophrenia. Genes Brain Behav, 2011. 10(4): p. 410-7.

Jackson, P.F., et al., Design and pharmacological activity of phosphinic acid based NAALADase inhibitors. J Med Chem, 2001. 44(24): p. 4170-5.

Jackson, P.F., et al., Design, synthesis, and biological activity of a potent inhibitor of the neuropeptidase N-acetylated alpha-linked acidic dipeptidase. J Med Chem, 1996. 39(2): p. 619-22.

Jackson et al., Certain phosphinyl derivatives useful as NAALADase inhibitors. Chemical Abstracts Service. 1998. Accession No. 1998:28658, 2 pages.

Jancurza, K.J., et al., NAAG peptidase inhibitors and deletion of NAAG peptidase gene enhance memory in novel object recognition test. Eur J Pharmacol, 2013. 701(1-3): p. 27-32.

Kaser, A., et al. Inflammatory bowel disease. Annu. Rev. Immunol. 2010, 28:573-621.

Kearney B.P., et al. Tenofovir disoproxil fumarate: clinical pharmacology and pharmacokinetics. Clin Pharmacokinet, 2004. 43(9): p. 595-612.

Kim et al., An Efficient Conjugate Addition of Dialkyl Phosphate to Electron-Deficient Olefins: The Use of a Nucleophilic Organocatalyst to Form a Strong Base. Chemical Abstracts Service. Accession No. 2013:551288, 1 page.

Kim et al., An Efficient Conjugate Addition of Dialkyl Phosphate to Electron-Deficient Olefins: The Use of a Nucleophilic Organocatalyst to Form a Strong Base. Bulletin of the Korean Chemical Society, 2013. 34(3):989-92.

Kozuch, P.L. et al. Treatment of inflammatory bowel disease: A review of medical therapy. World J. Gastroenterol. 2008, 14:354-377.

Lawrance, LC. What is left when anti-tumour necrosis factor therapy in inflammatory bowel diseases fails? World J. Gastroenterol. 2014, 20: 1248-1258.

Liu et al., Pseudoirreversible inhibition of prostate-specific membrane antigen by phosphoramidate peptidomimetics. Biochemistry. Dec. 2, 2008;47(48):12658-60.

Mesters, J.R. et al. Structure of glutamate carboxypeptidase II, a drug target in neuronal damage and prostate cancer. EMBO J. 2006, 25:1375-1384.

Neale, J.H., et al. N-Acetylaspartylglutamate: the most abundant peptide neurotransmitter in the mammalian central nervous system. J Neurochem, 2000. 75(2): p. 443-52.

Oliver et al., Conformational and SAR analysis of NAALADase and PSMA inhibitors. Bioorg Med Chem. Oct. 1, 2003;11(20):4455-61.

Olszewski, R.T., et al. mGluR3 and not mGluR2 receptors mediate the efficacy of NAAG peptidase inhibitor in validated model of schizophrenia. Schizophr Res, 2012. 136(1-3): p. 160-1.

Olszewski, R.T., et al., NAAG peptidase inhibitors block cognitive deficit induced by MK-801 and motor activation induced by d-amphetamine in animal models of schizophrenia. Transl Psychiatry, 2012. 2: p. e145.

Rahn, K.A., et al., Inhibition of glutamate carboxypeptidase II (GCPII) activity as a treatment for cognitive impairment in multiple sclerosis. Proc Natl Acad Sci US A, 2012. 109(49): p. 20101-6.

Rais, R. et al., Bioanalytical method for evaluating the pharmacokinetics of the GCP-II inhibitor 2-phosphonomethyl pentanedioic acid (2-PMPA). J. Pharm. Biomed. Anal. 2014, 88:162-169.

Regueiro, M., et al. Infliximab dose intensification in Crohn's disease. Inflamm. Bowel Dis. 2007, 13:1093-1099.

Ristau, et al. The prostate-specific membrane antigen: Lessons and current clinical implications from 20 years of research. Ural. Oneal. 2013, 32(3):272-9.

Robinson, et al., Hydrolysis of the brain dipeptide N-acetyl-L-aspartyl-L-glutamate. Identification and characterization of a novel N-acetylated alpha-linked acidic dipeptidase activity from rat brain. J. Biol. Chem. (1987) 262 (30):14498-14506.

Rowland, L.M., et al., In vivo measurements of glutamate, GABA, and NAAG in schizophrenia. Schizophr Bull, 2013. 39(5): p. 1096-104.

Sartor, R.B., Mechanisms of disease: pathogenesis of Crohn's disease and ulcerative colitis. Nat. Clin. Pract. Gastroenterol. Hepatol. 2006, 3:390-407.

Sartorius L.J., et al., Expression of a GRM3 splice variant is increased in the dorsolateral prefrontal cortex of individuals carrying a schizophrenia risk SNP. Neuropsychopharmacology, 2008. 33(11): p. 2626-34.

Schmidt C. et al., Predictive value of mucosal TNF-alpha transcripts in steroid-refractory Crohn's disease patients receiving intensive immunosuppressive therapy. Inflamm. Bowel Dis. 2007, 13:65-70.

Schreiber, S. et al., Maintenance therapy with certolizumab pegol for Crohn's disease. N Engl. J. Med. 2007, 357:239-250.

Shi et al., Dendrimer based compositions for therapeutic and diagnostic applications. Chemical Abstracts Service. 2008. Accession No. 2008:71328, 2 pages.

Slusher, B.S., et al., Selective inhibition of NAALADase, which converts NAAG to glutamate, reduces ischemic brain injury. Nat Med, 1999. 5(12): p. 1396-402.

Strober W. et al., The fundamental basis of inflammatory bowel disease. J. Clin. Invest. 2007, 117:514-521.

Thackaberry, E.A. Vehicle selection for nonclinical oral safety studies. Expert Opin. Drug Metab. Toxicol. 2013, 9:1635-1646.

Tsai, G.C., et al., Reductions in acidic amino acids and Nacetylaspartylglutamate in amyotrophic lateral sclerosis CNS. Brain Res, 1991. 556(1): p. 151-6.

Van Assche, G. et al. Progressive multifocal leukoencephalopathy after natalizumab therapy for Crohn's disease. N Engl. J. Med. 2005, 353:362-368.

Villablanca, E.J. et al. beta7 integrins are required to give rise to intestinal mononuclear phagocytes with tolerogenic potential. Gut, Sep. 12, 2013.

Wu et al., The molecular pruning of a phosphoramidate peptidomimetic inhibitor of prostate-specific membrane antigen. Bioorg Med Chem. Dec. 1, 2007;15(23):7434-43.

Xavier, R.J. et al. Unravelling the pathogenesis of inflammatory bowel disease. Nature 2007, 448:427-434.

Yamada, T., et al., NAAG peptidase inhibition in the periaqueductal gray and rostral ventromedial medulla reduces flinching in the formalin model of inflammation. Mol Pain, 2012. 8: p. 67.

(56) References Cited

OTHER PUBLICATIONS

Zhang, T., et al., An ileal Crohn's disease gene signature based on whole human genome expression profiles of disease unaffected ileal mucosa! biopsies. PLoS ONE 2012;7:e37139.

Ziehn, M.O., et al., Hippocampal CA1 atrophy and synaptic loss during experimental autoimmune encephalomyelitis, EAE. Lab Invest, 2010. 90(5): p. 774-86.

* cited by examiner

N-Acetylaspartylglutamate (NAAG) ⇧    N-Acetylaspartate    Glutamate ⇩

PRODRUGS OF PROSTATE SPECIFIC MEMBRANE ANTIGEN (PSMA) INHIBITOR

CROSS-REFERENCE TO RELATED APPLICATIONS

This application is a continuation of U.S. patent application Ser. No. 16/751,556, filed Jan. 24, 2022, now U.S. Pat. No. 11,325,931, of U.S. patent application Ser. No. 15/968,074, filed May 1, 2018, which is a divisional of U.S. patent application Ser. No. 15/502,105, filed Feb. 6, 2017, now U.S. Pat. No. 9,988,407, which is a § 371 U.S. National Entry of PCT/US2015/044053, filed Aug. 6, 2015, which claims the benefit of U.S. Provisional Application No. 62/033,926, filed Aug. 6, 2014, which is incorporated herein by reference in its entirety.

FEDERALLY SPONSORED RESEARCH OR DEVELOPMENT

This invention was made with government support under CA161056 awarded by the National Cancer Institute (NCI). The government has certain rights in the invention.

BACKGROUND

The prodrug approach is a well-established strategy to improve physicochemical, biopharmaceutic and pharmacokinetic properties of potential drug molecules. Approximately 5-7% of drugs approved worldwide are prodrugs with annual sales in 2013 of $11.2 billion. Most prodrugs are simple chemical derivatives of the original molecule. Ester prodrugs, the most common prodrugs, constitute 49% of all marketed prodrugs. Reasons for the popularity of ester prodrugs include their generally straight forward synthesis, their improved lipophilicity and membrane permeability, and the ubiquitousness of estereases. An example of an approach to make an ester prodrug is capping the acidic moiety(ies) with lipophilic alkyl or alkyloxymethyl esters (i.e., pivaloyloxymethyl (POM) or propyloxycarbonyloxymethyl (POC); e.g., Enalapril, Adefovir). Another approach is to cap the acidic moiety(ies) with amino acids to make amides that are recognizable by transporters, such as Peptide transporter 1 (PEPT1) (e.g., Pomaglumetad methionil, Valacyclovir).

PSMA (Prostate Specific Membrane Antigen), also termed GCPII (glutamate carboxypeptidase II) and FOLH1, is a metallopeptidase that catalyzes the hydrolysis of N-acetylated aspartate-glutamate (NAAG) to N-acetyl aspartate (NAA) and glutamate and cleaves terminal glutamate moieties sequentially from folate polyglutamate (Ristau et al., 2013; Mesters et al., 2006; Slusher et al., 2013). One of the most potent, selective, and efficacious PSMA inhibitors is 2-PMPA ($K_i$ or $IC_{50}$=300 pM). After 50-100 mg/kg intraperitoneal injection (i.p.) doses, it achieves 30-50 µM concentrations in the brain and provides efficacy in over 20 animal models of the central nervous system (CNS) or peripheral nervous system (PNS) including diabetic neuropathy, peripheral neuropathy, neuropathic pain, general pain, stroke, drug addiction, amyotrophic lateral sclerosis (ALS), multiple sclerosis (MS), schizophrenia, epilepsy and several others associated with pathological increase of glutamate concentration leading to excito-toxic effects and neuronal death. However, 2-PMPA is a highly polar compound with multiple carboxylates and a zinc binding group and it has negligible oral availability. Therefore, in most cases, it must be dosed intravenously, intraperitoneally, or locally to achieve the desired effects. This fact limits its potential use as a drug since most of the above disorders require long term dosing for which the oral route is strongly preferred.

SUMMARY

In some aspects, the presently disclosed subject matter provides a compound of formula (I) or formula (II):

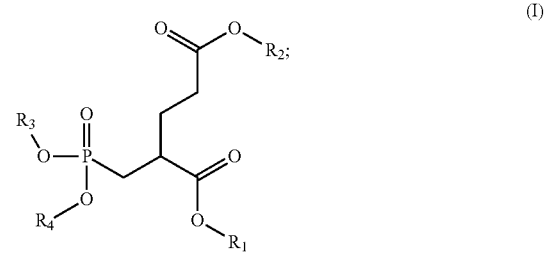

(I)

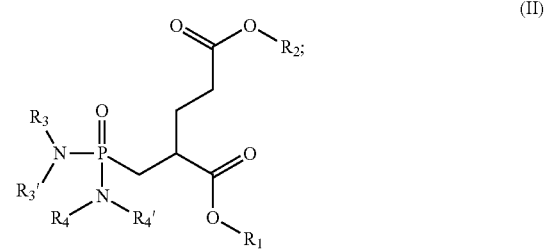

(II)

wherein:

each $R_1$, $R_2$, $R_3$, and $R_4$ is independently selected from the group consisting of H, alkyl, Ar, —$(CR_5R_6)_n$—Ar, —$(CR_5R_6)_n$—O—C(=O)—$R_7$, —$(CR_5R_6)_n$—C(=O)—O—$R_7$, —$(CR_5R_6)_n$—O—C(=O)—O—$R_7$, —$(CR_5R_6)_n$—O—$R_7$, —$(CR_5R_6)_n$—O—[$(CR_5R_6)_n$—O]$_m$—$R_7$, —$(CR_5R_6)_n$—Ar—O—C(=O)—$R_7$, —Ar—C(=O)—O—$(CR_5R_6)_n$—$R_7$, —$(CR_5R_6)_n$—$NR_8R_9$, and —$(CR_5R_6)_n$—C(=O)—$NR_8R_9$;

wherein:

n is an integer from 1 to 20;

m is an integer from 1 to 20;

each $R_3'$ and $R_4'$ are independently H or alkyl;

each $R_5$ and $R_6$ is independently selected from the group consisting of H, alkyl, and alkylaryl;

each $R_7$ is independently straightchain or branched alkyl;

Ar is aryl, substituted aryl, heteroaryl or substituted heteroaryl; and $R_8$ and $R_9$ are each independently H or alkyl; and pharmaceutically acceptable salts thereof.

In particular aspects, the compound of formula (I) is selected from the group consisting of:

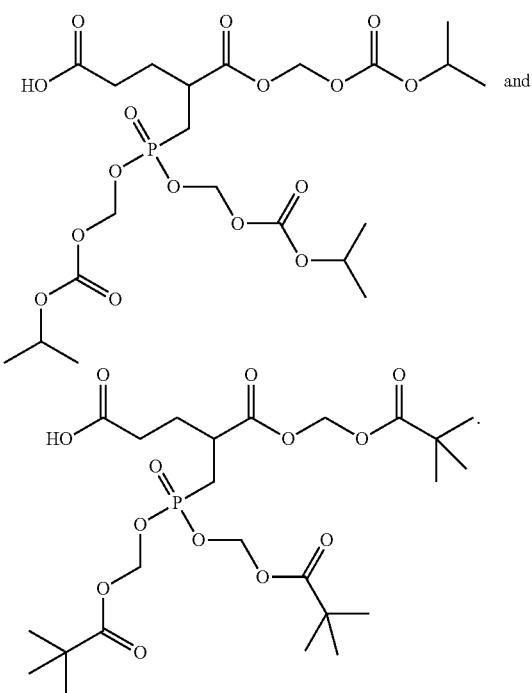

In other aspects, the presently disclosed subject matter provides a method for treating a disease or a condition, the method comprising administering to a subject in need of treatment thereof, a compound of formula (I), a compound of formula (II), or a pharmaceutical composition thereof, in an amount effective for treating the disease or condition.

In particular aspects, the disease or condition is selected from the group consisting of a neurodegenerative disease, multiple sclerosis (MS), cancer, angiogenesis, and inflammatory bowel disease.

In certain aspects, the neurodegenerative disease is selected from the group consisting of amyotrophic lateral sclerosis (ALS), Parkinson's disease (PD), Alzheimer's disease (AD), Huntington's disease, dementia with Lewy Bodies (DLB), schizophrenia, pain, epilepsy, stroke, and traumatic brain injury (TBI).

In some aspects, the disease or condition results in excess PSMA activity. In such aspects, the method further comprises inhibiting the excess PSMA activity when the compound of formula (I), the compound of formula (II), or a pharmaceutical composition thereof, is administered.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
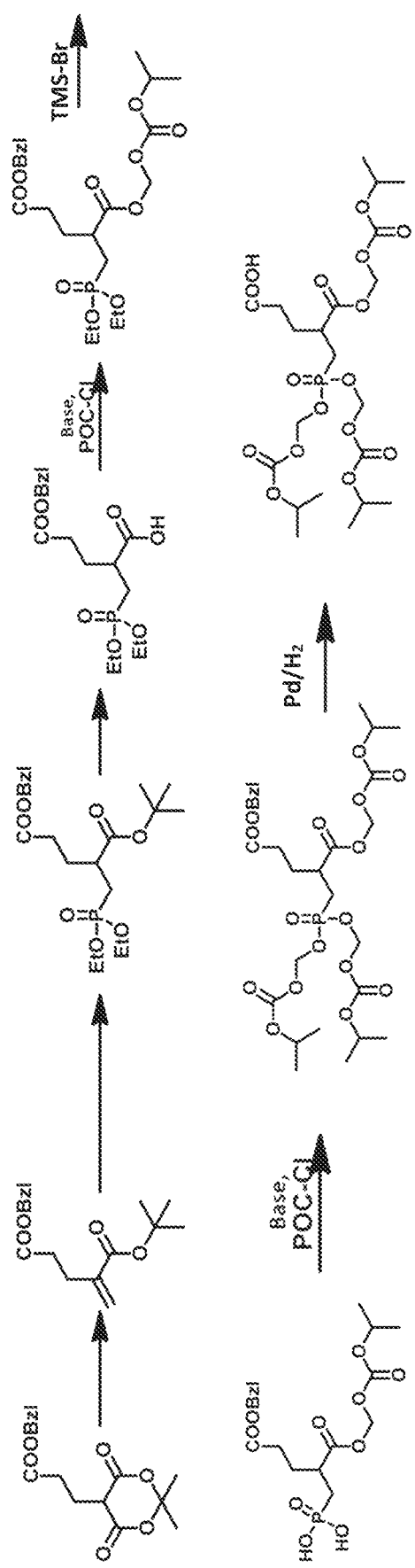
Figure 2:
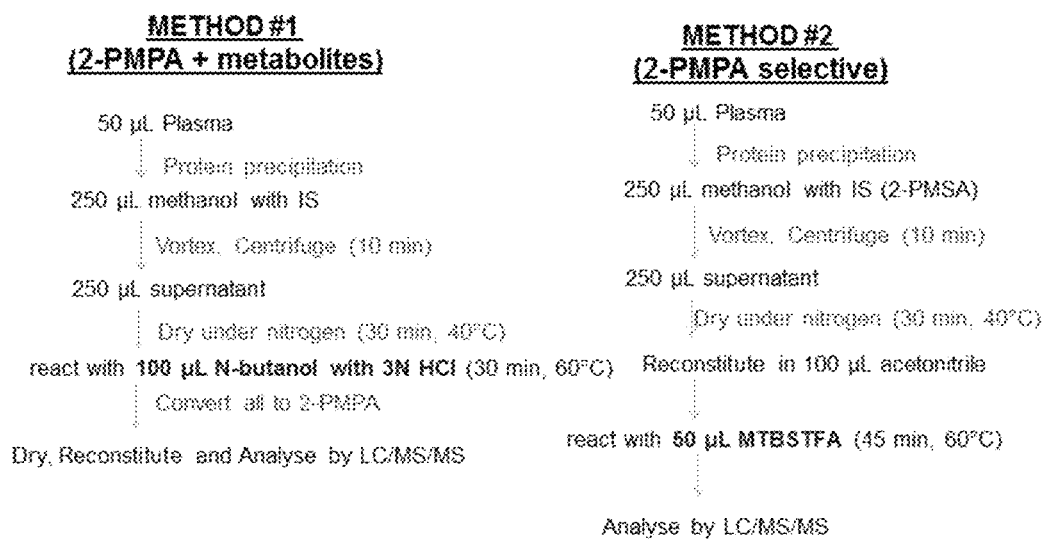
Figure 3:
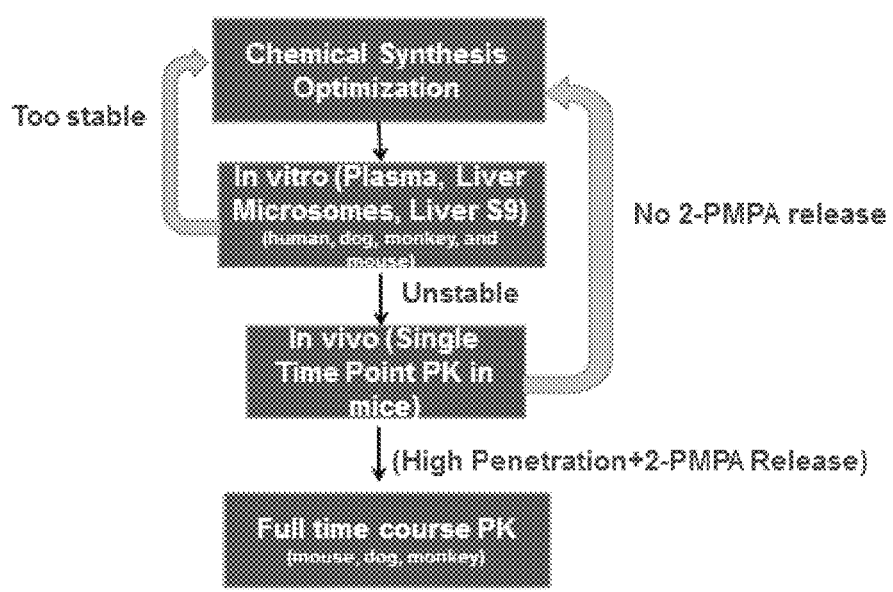
Figure 4:
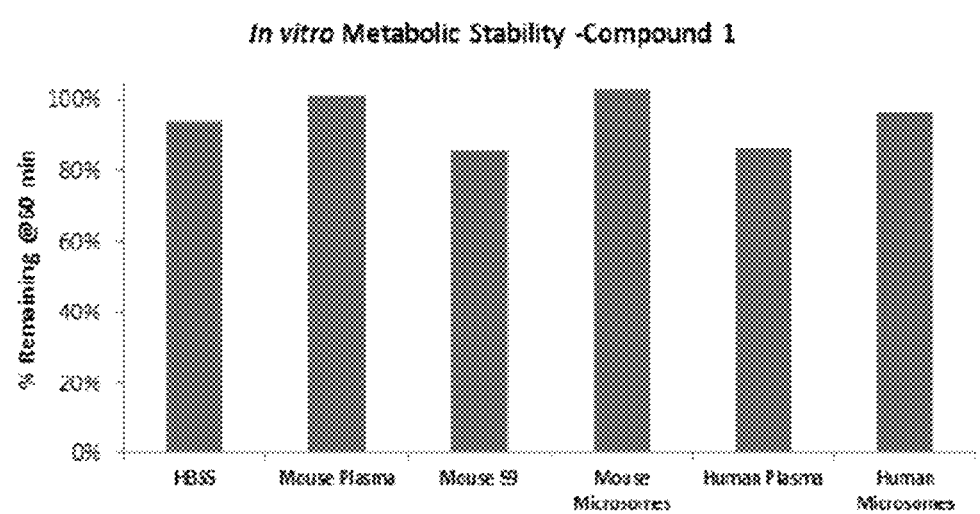
Figure 5:
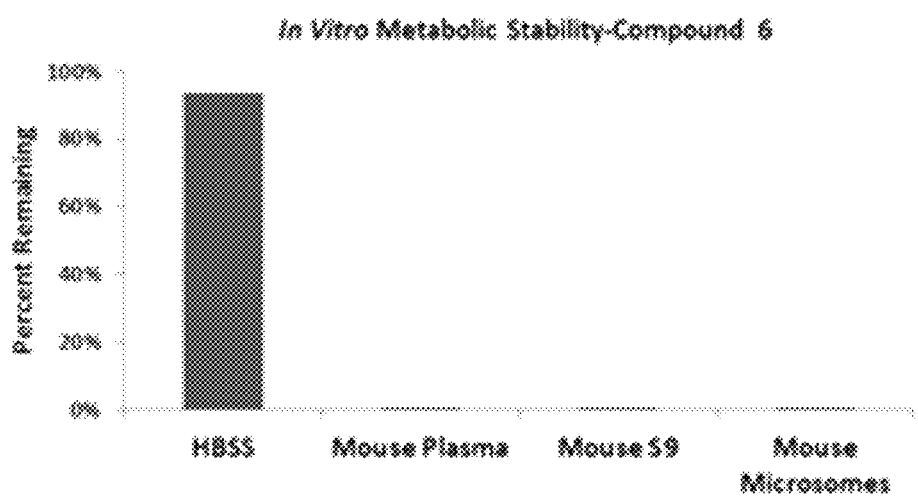
Figure 6:
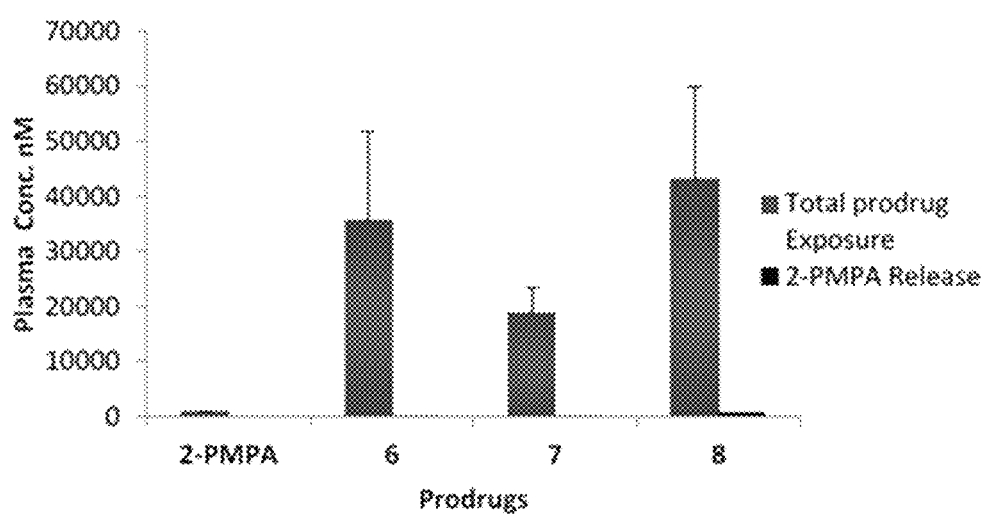
Figure 7:
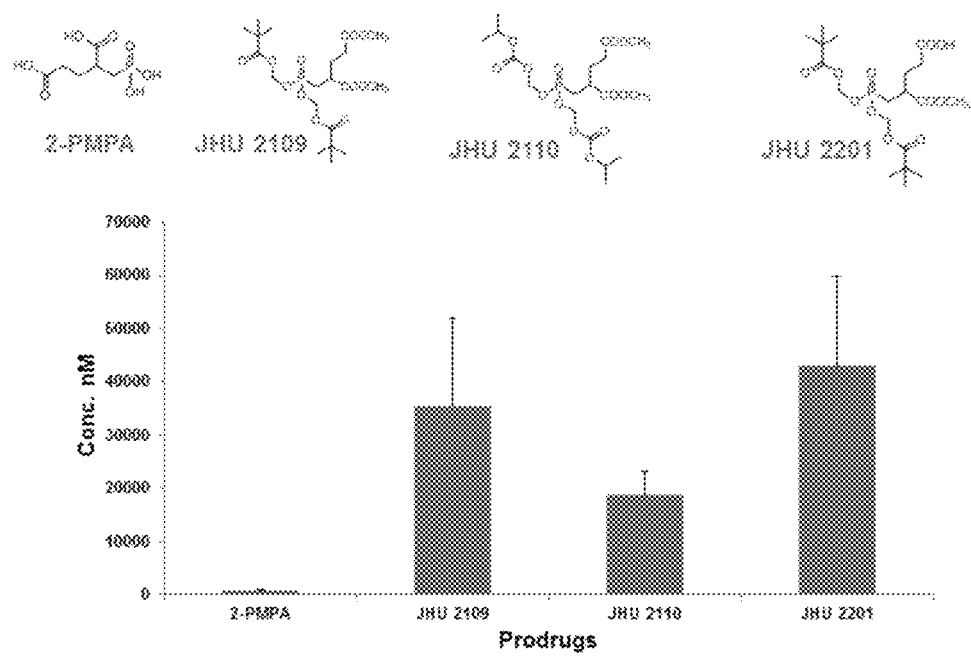
Figure 8:
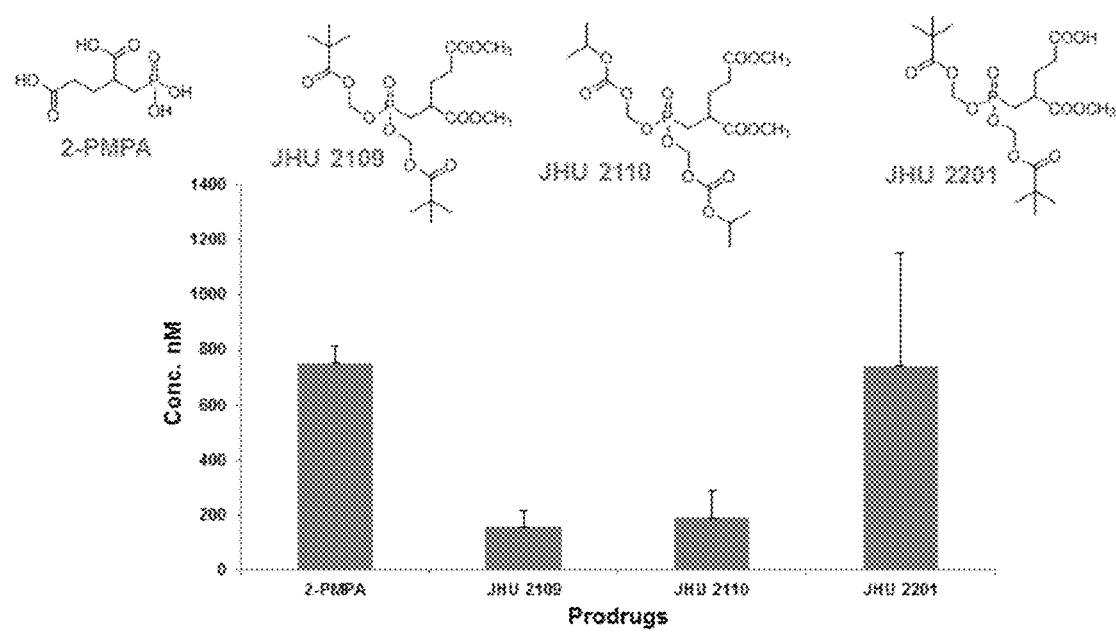
Figure 9A:
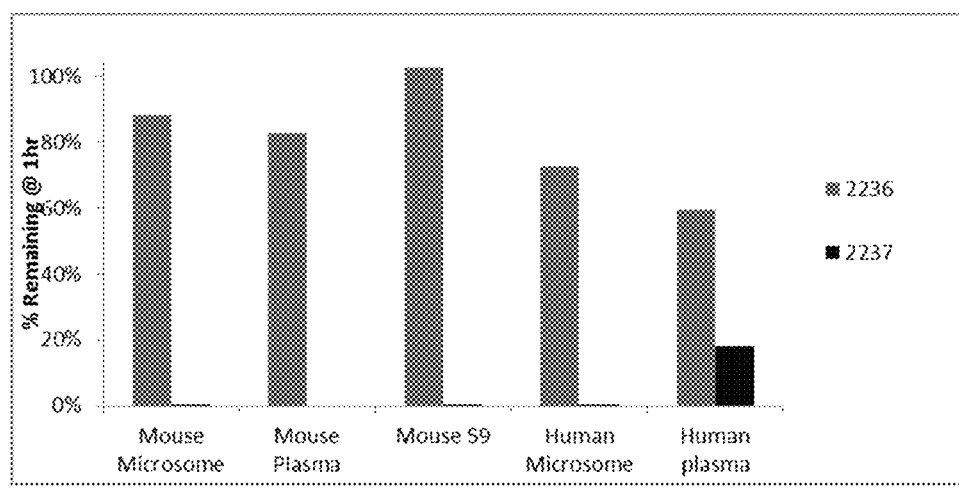
Figure 9B:
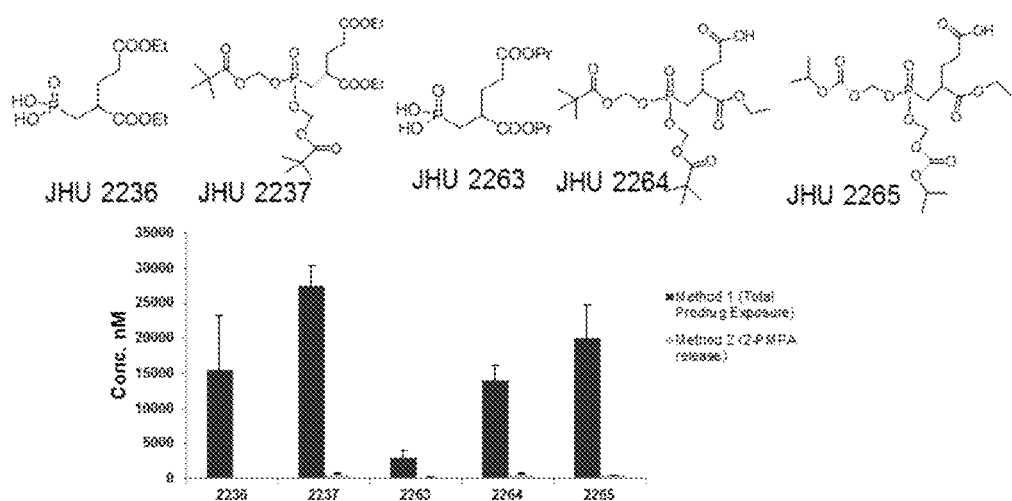
Figure 10A:
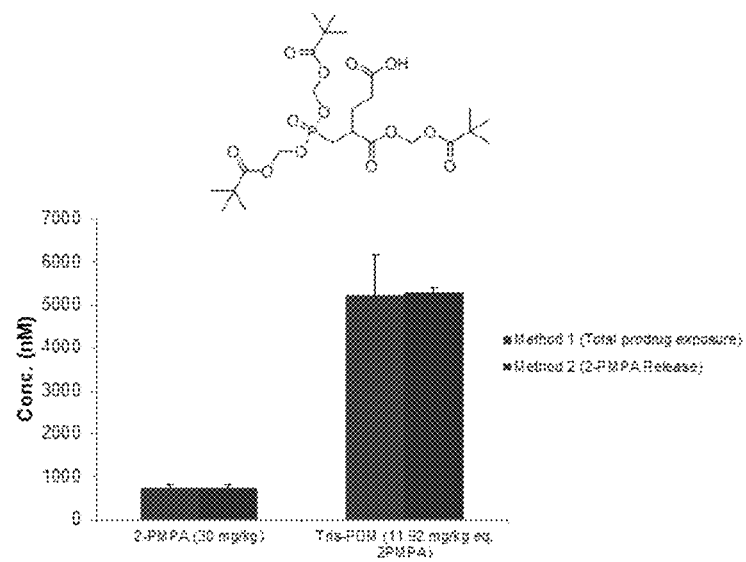
Figure 10B:
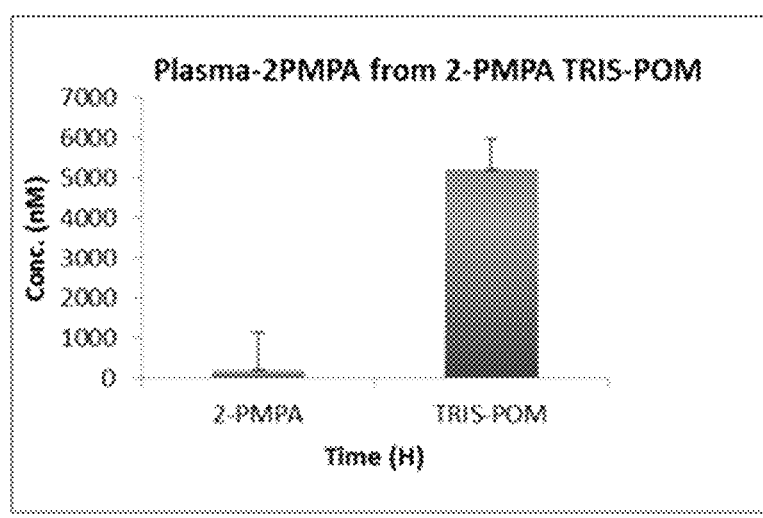
Figure 11A:
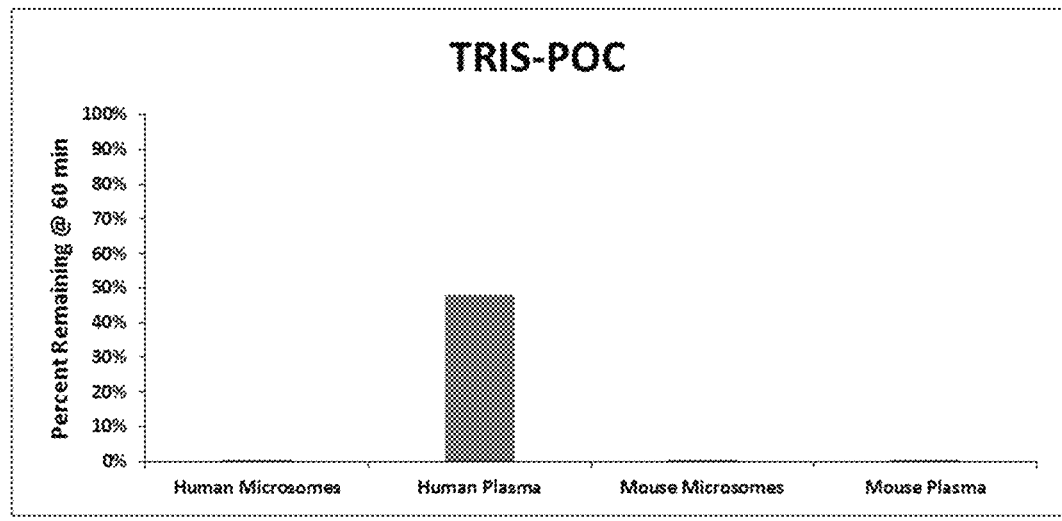
Figure 11B:
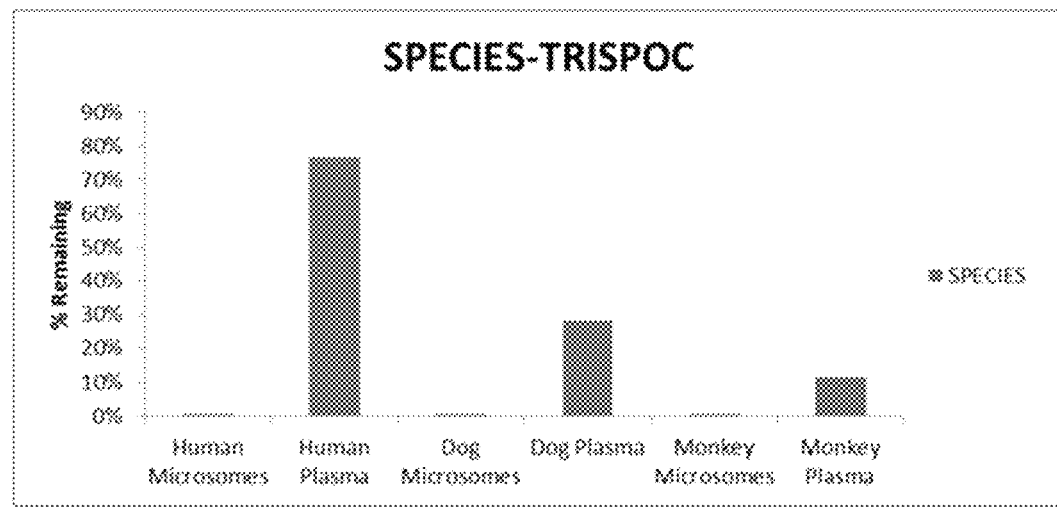
Figure 12:
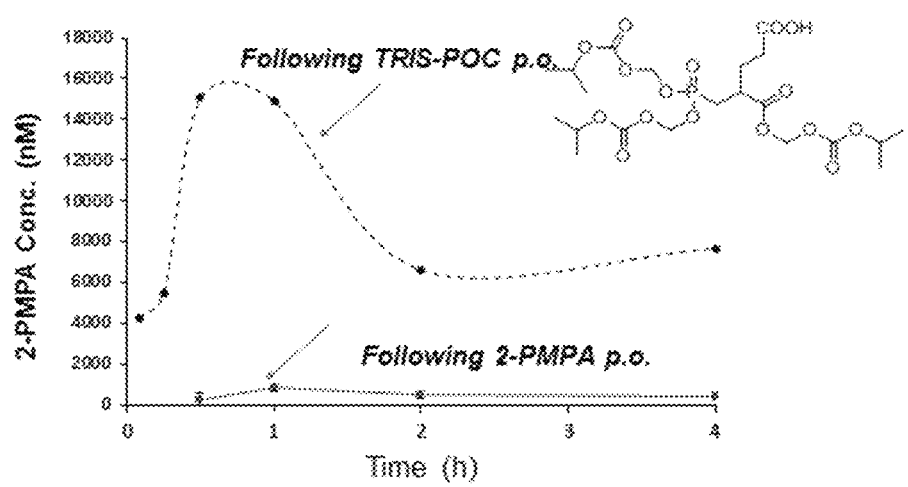
Figure 13:
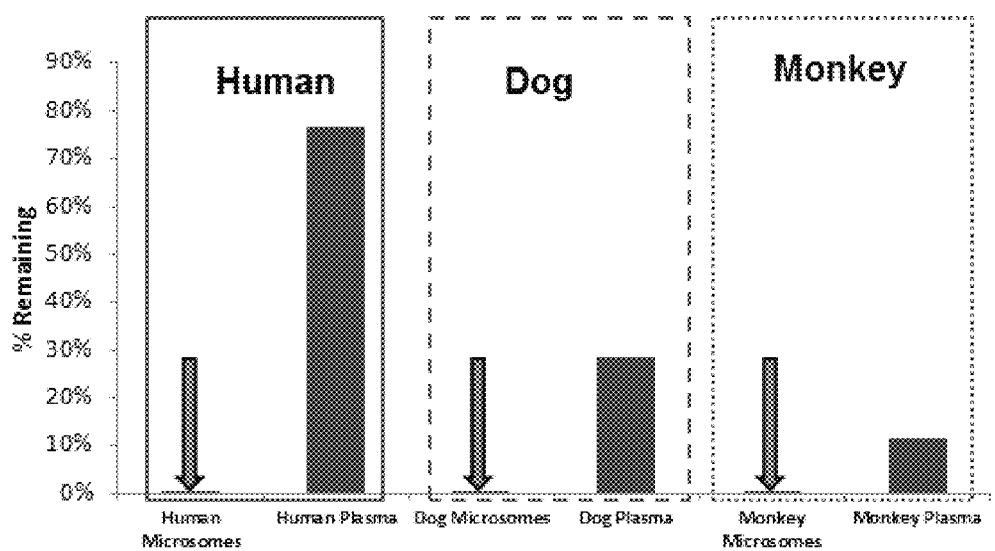
Figure 14:
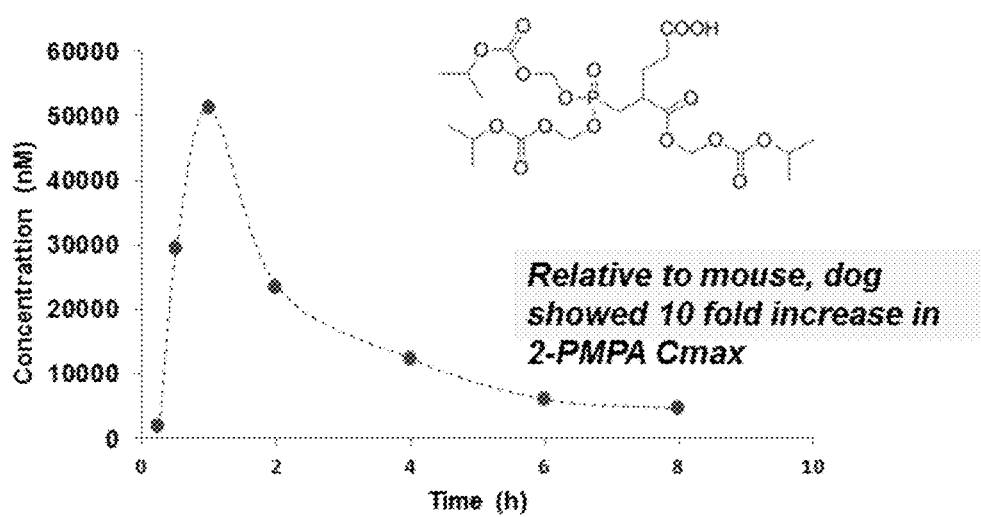
Figure 15:
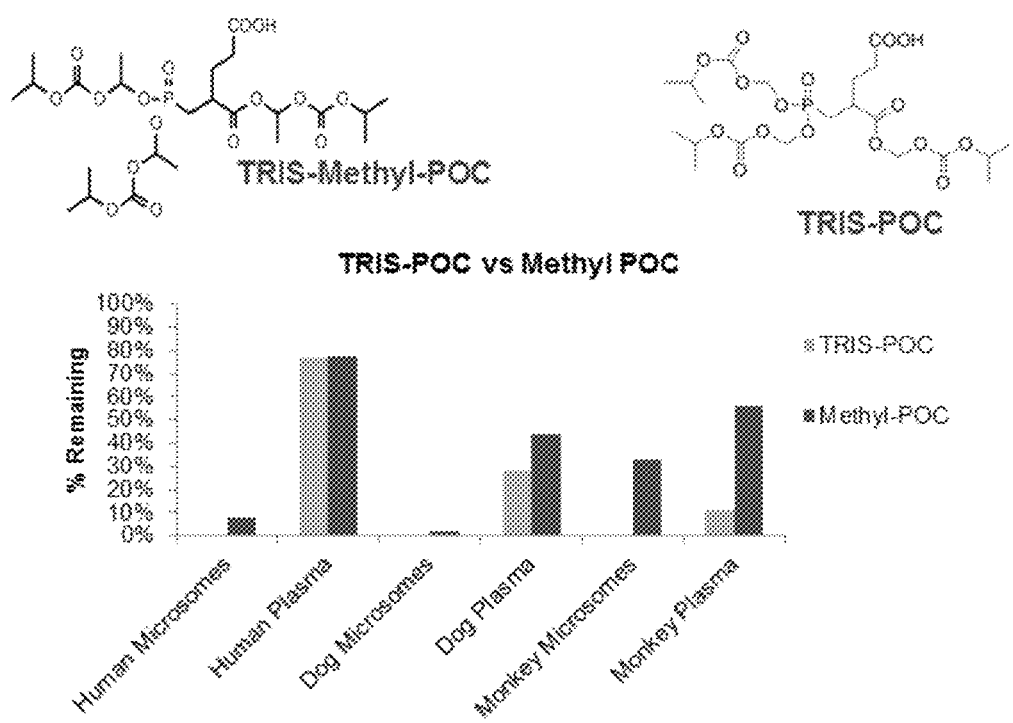
Figure 16:
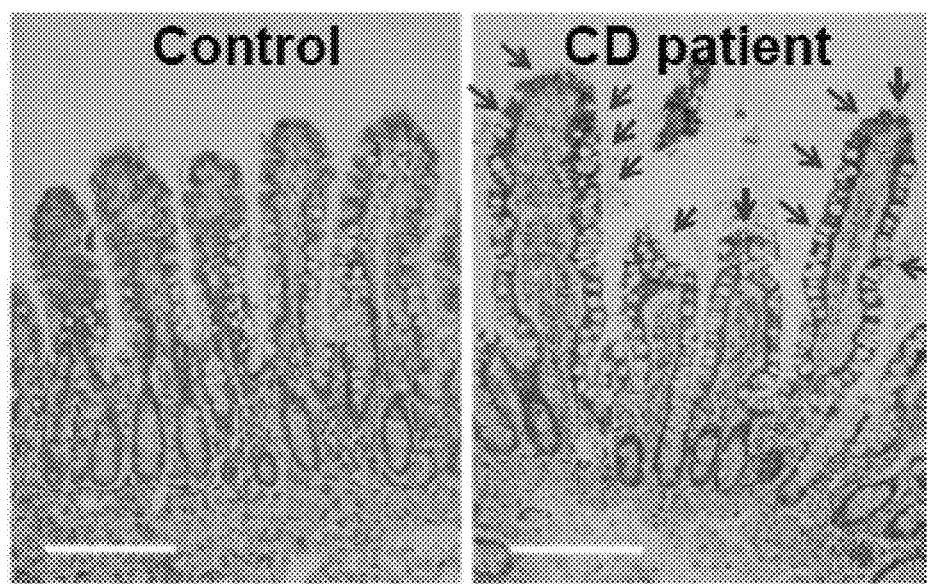
Figure 17:
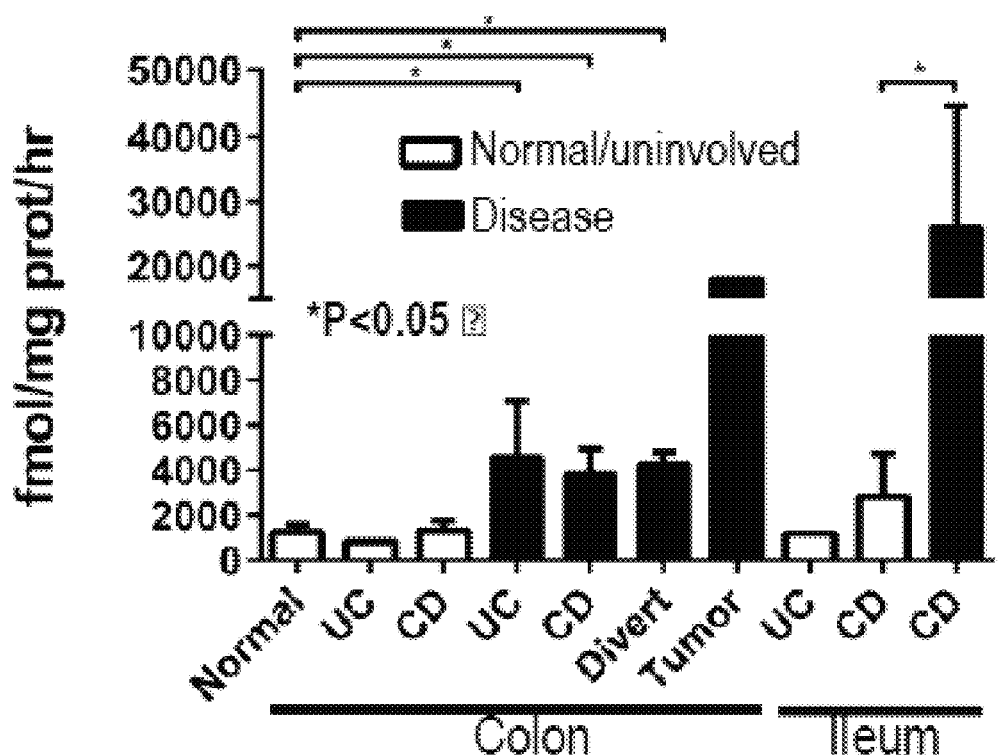
Figure 18:
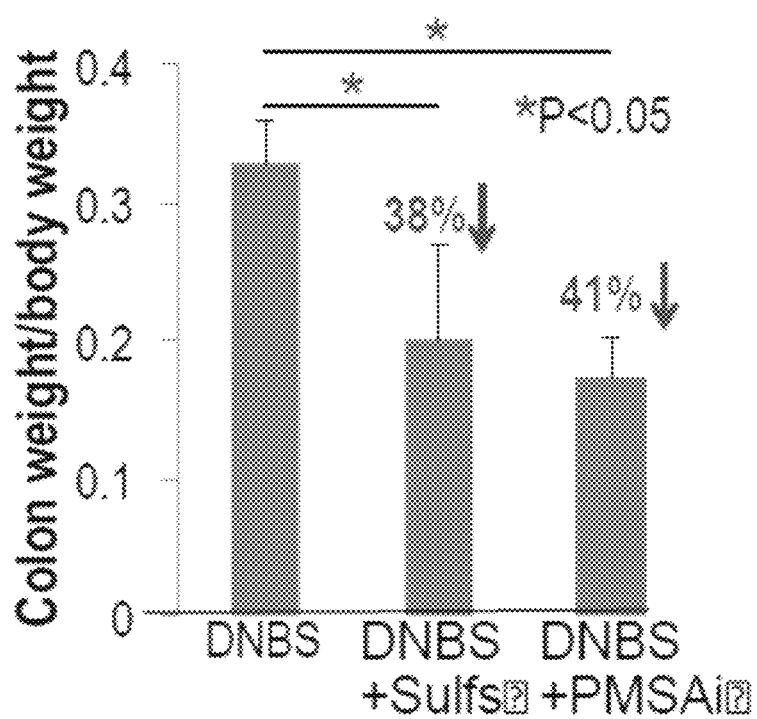
Figure 19:
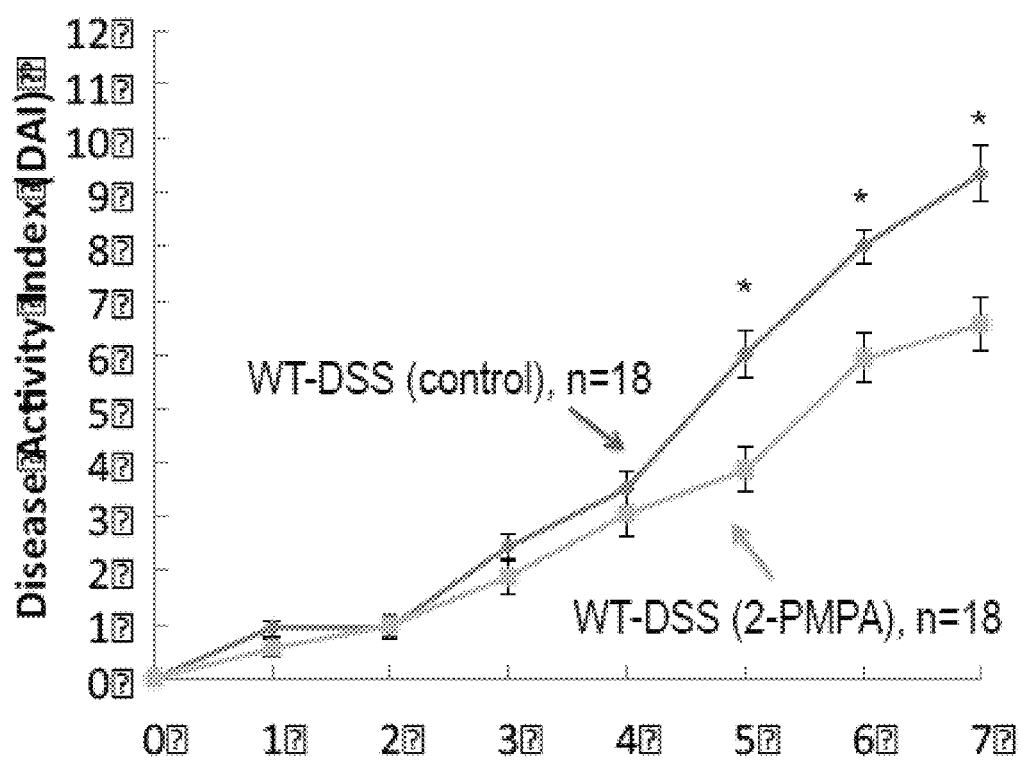
Figure 20:
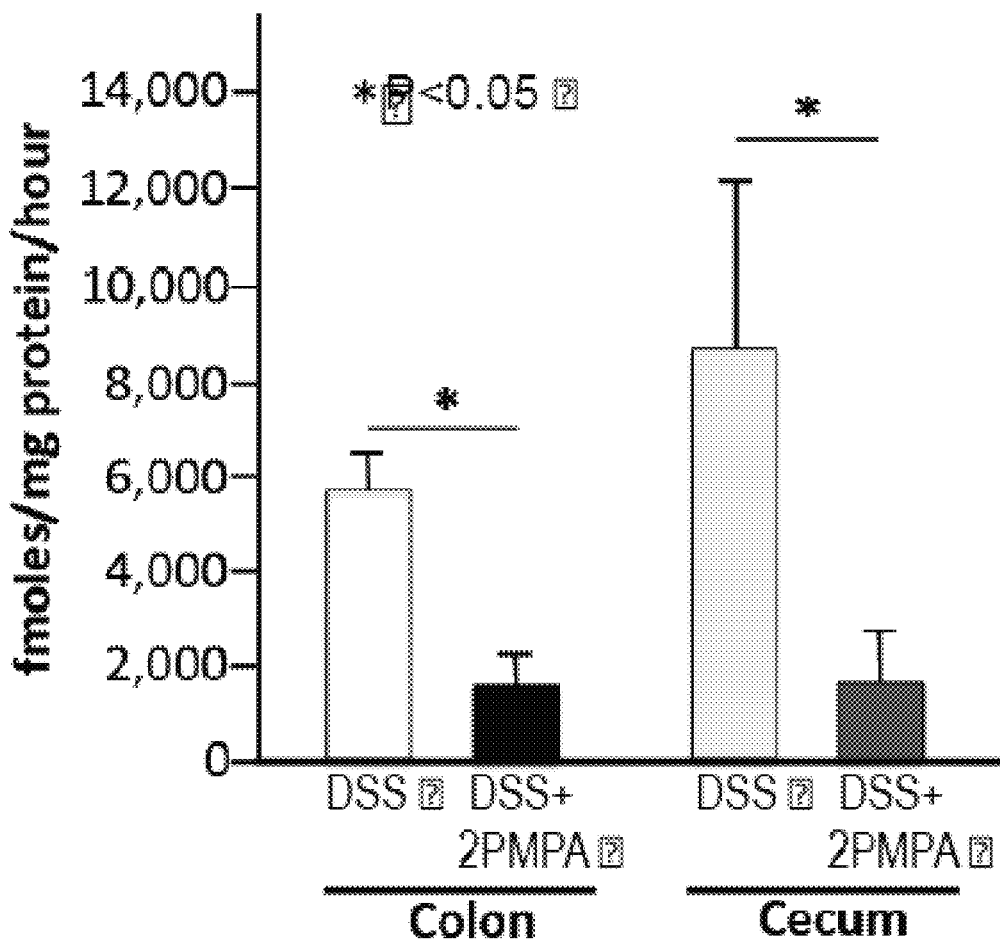
Figure 22:
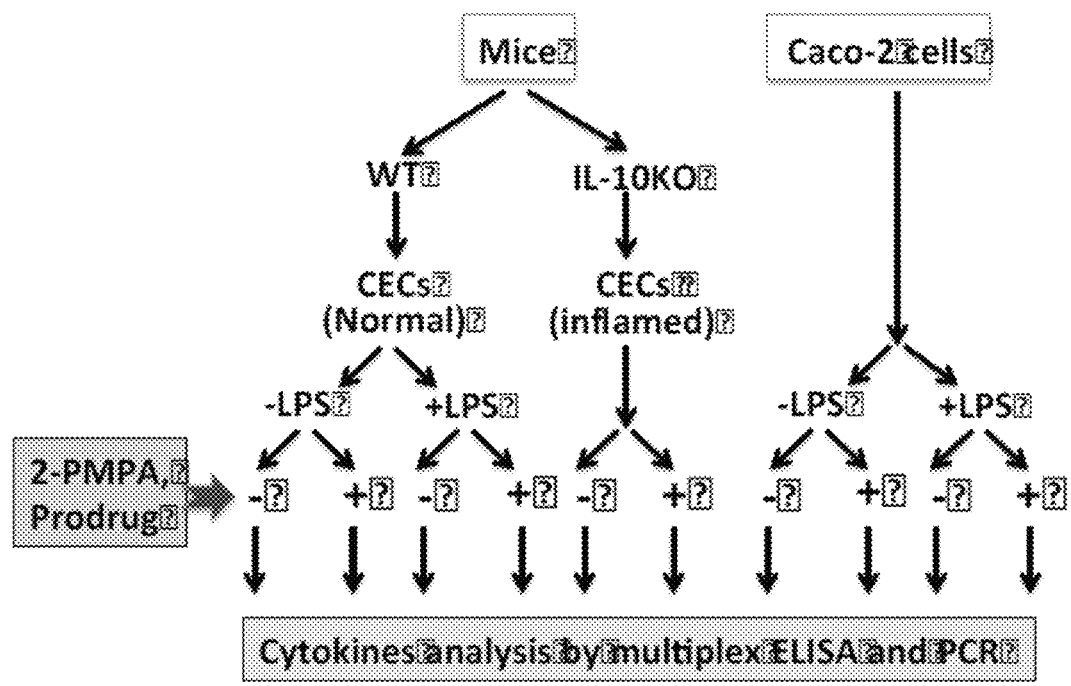
Figure 23A:
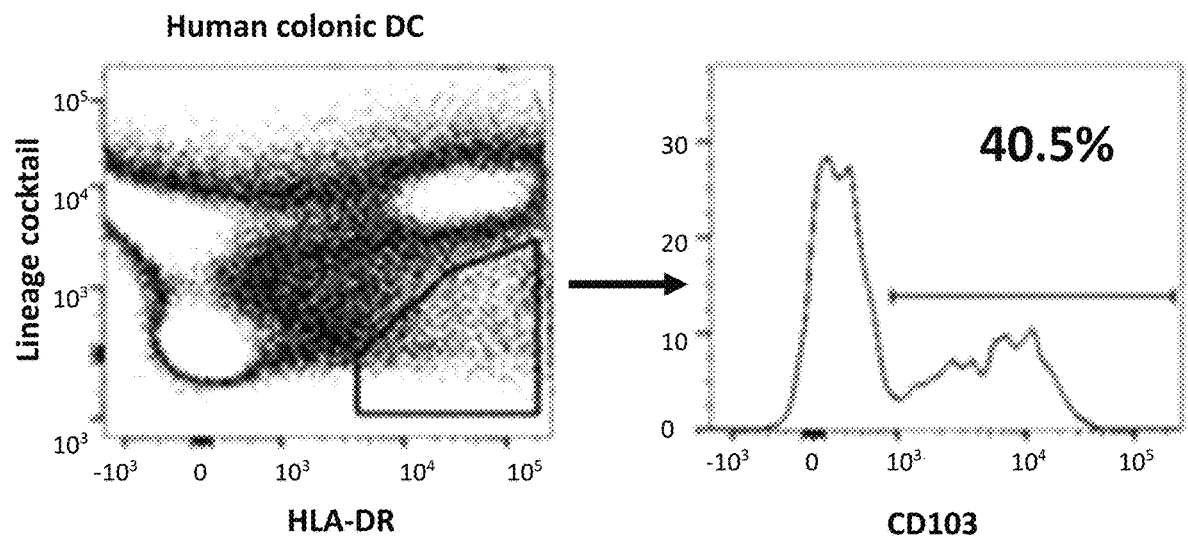
Figure 23B:
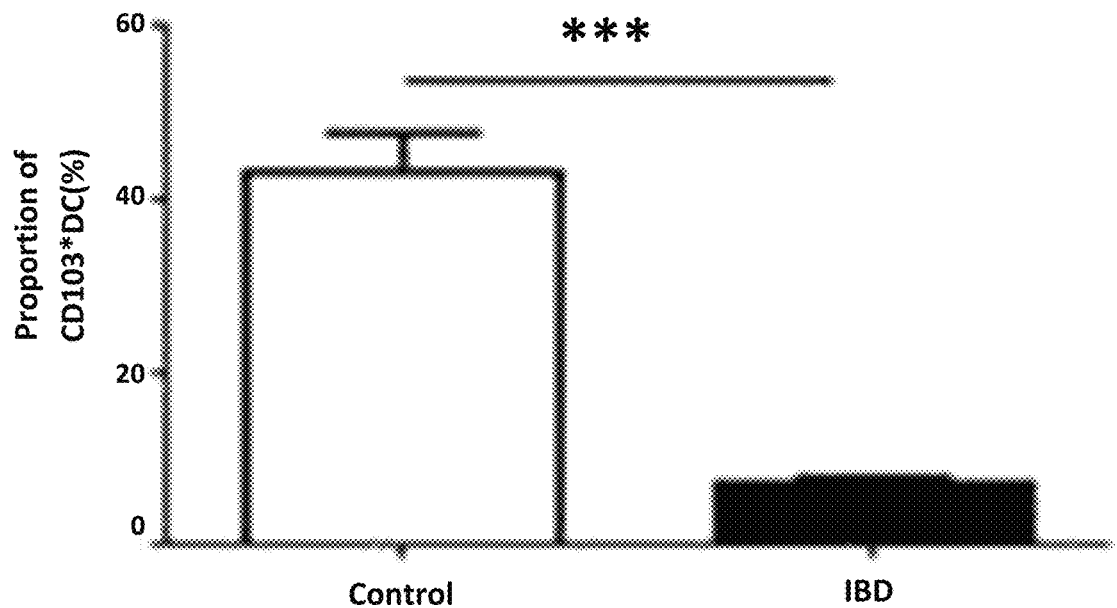
Figure 24B:
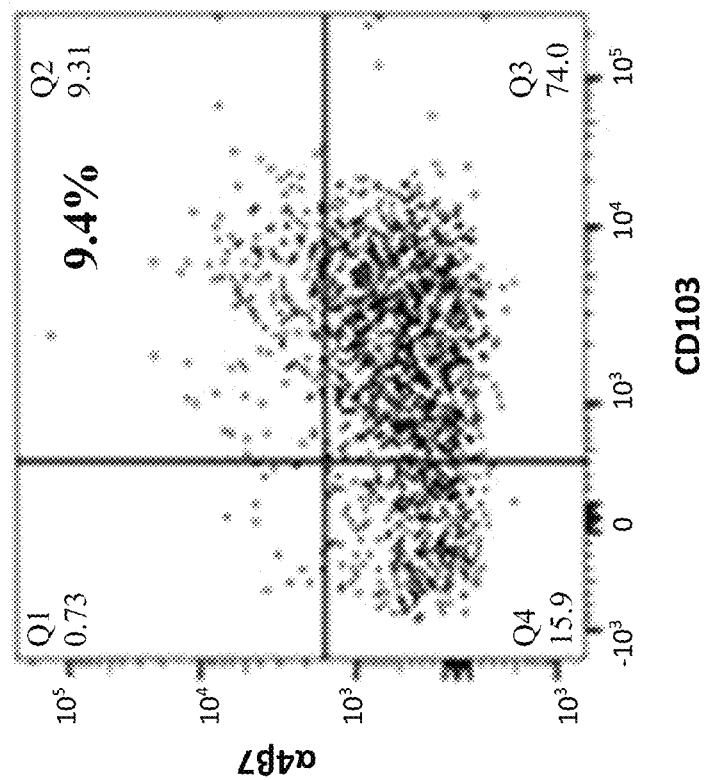
Figure 24A:
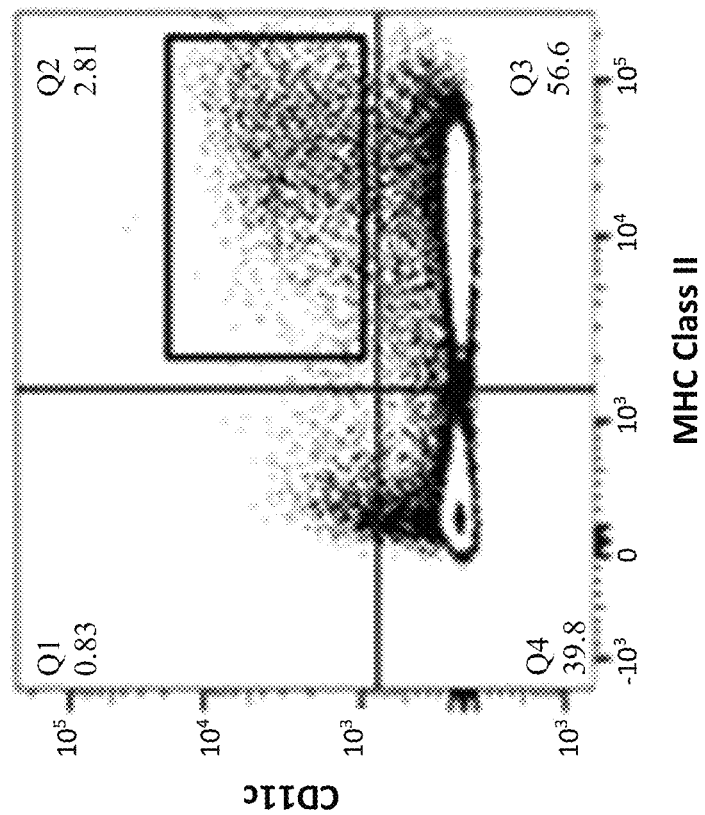
Figure 24D:
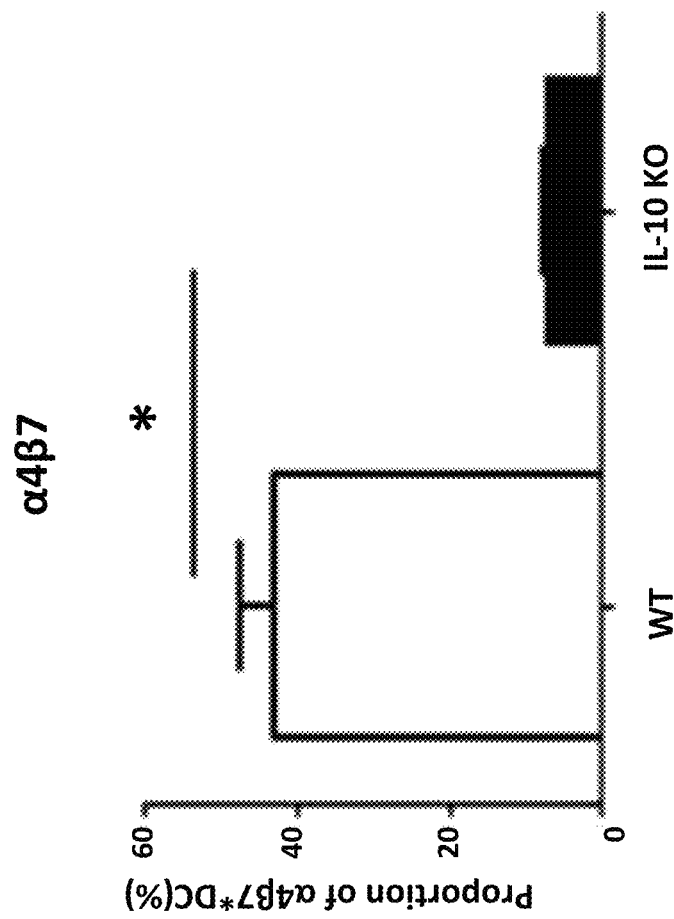
Figure 24C:
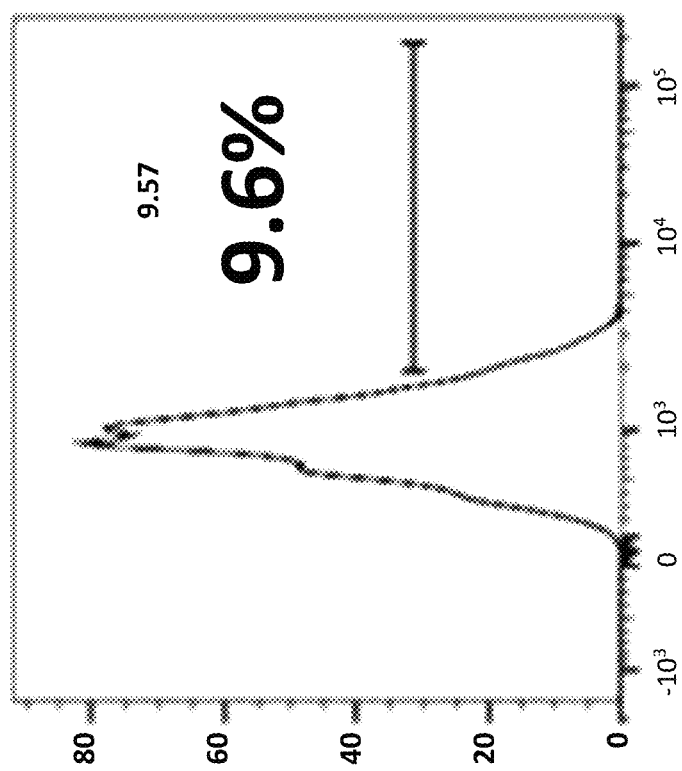
Figure 25:
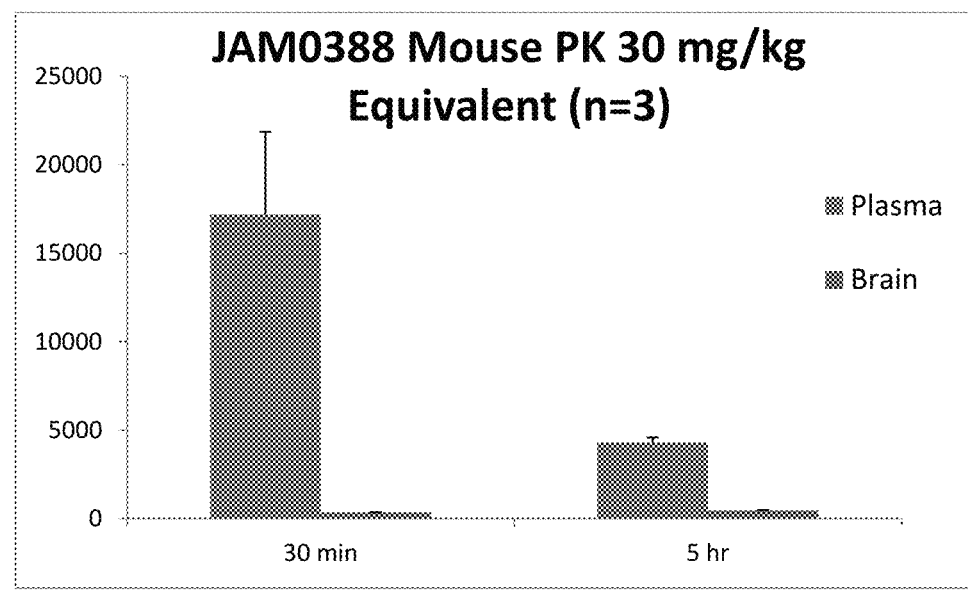
Figure 25:
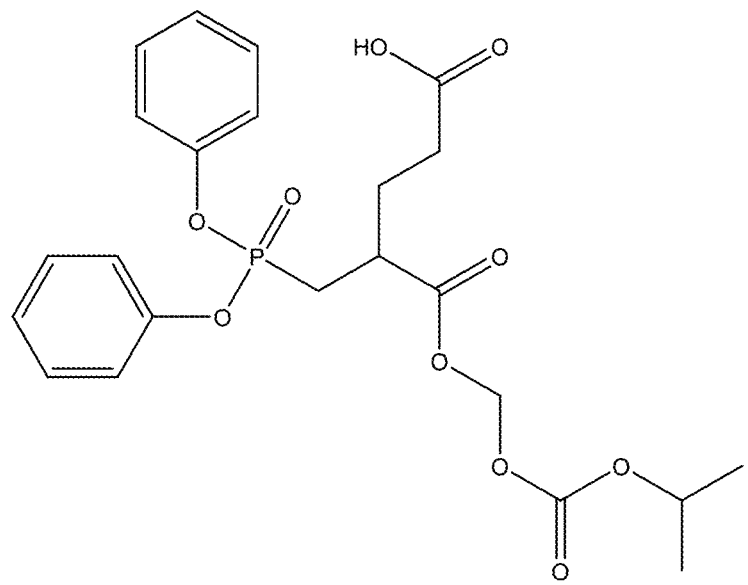
Figure 26:
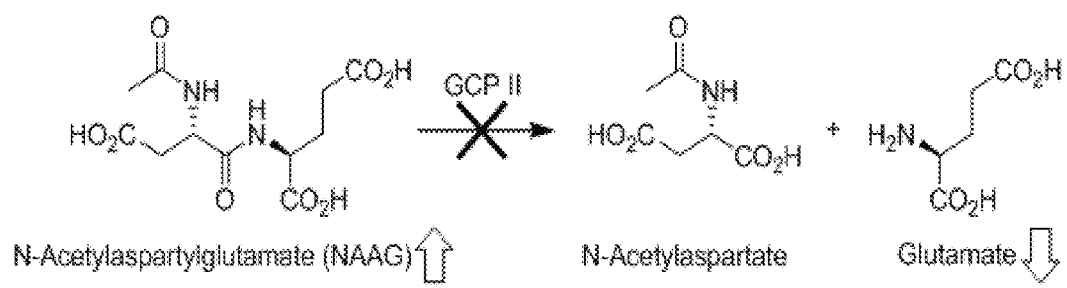
Figure 27:
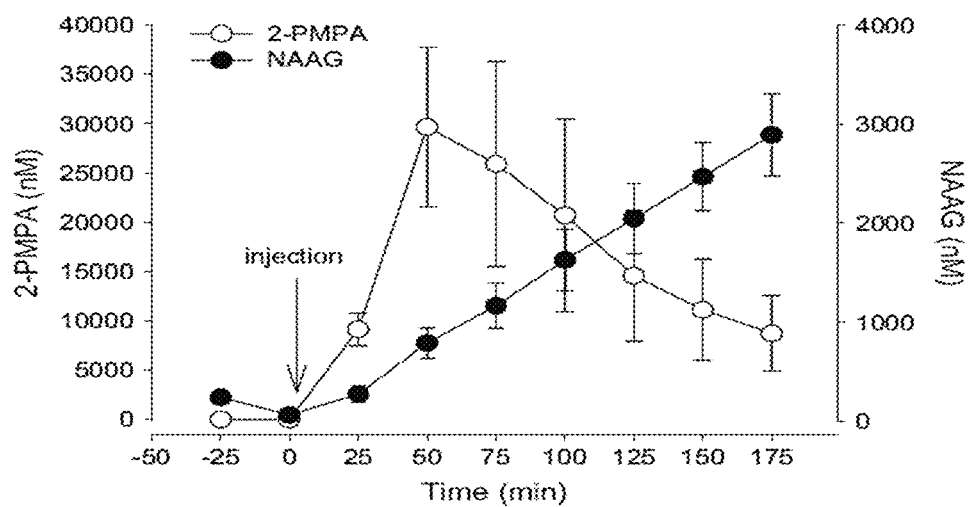
Figure 28A:
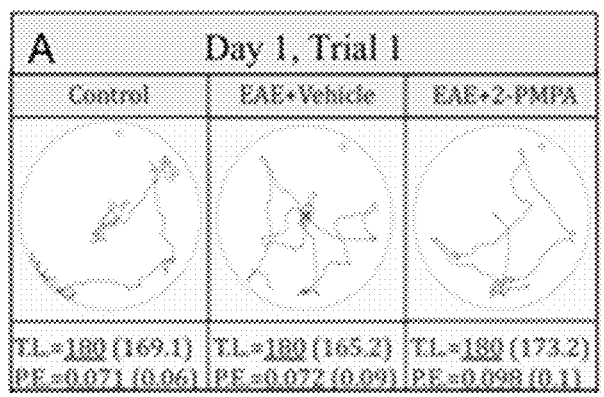
Figure 28B:
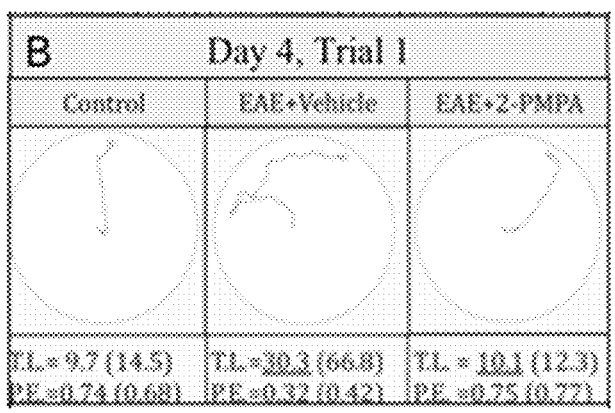
Figure 28C:
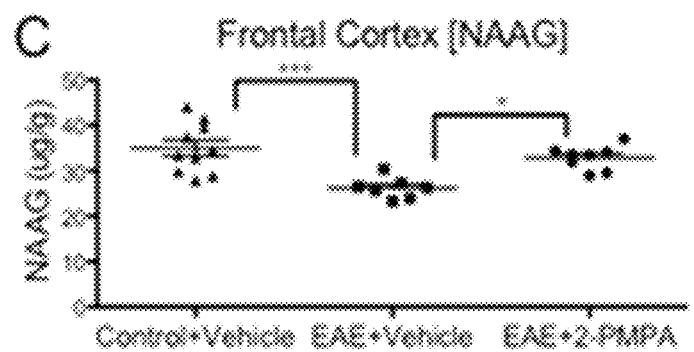
Figure 29:
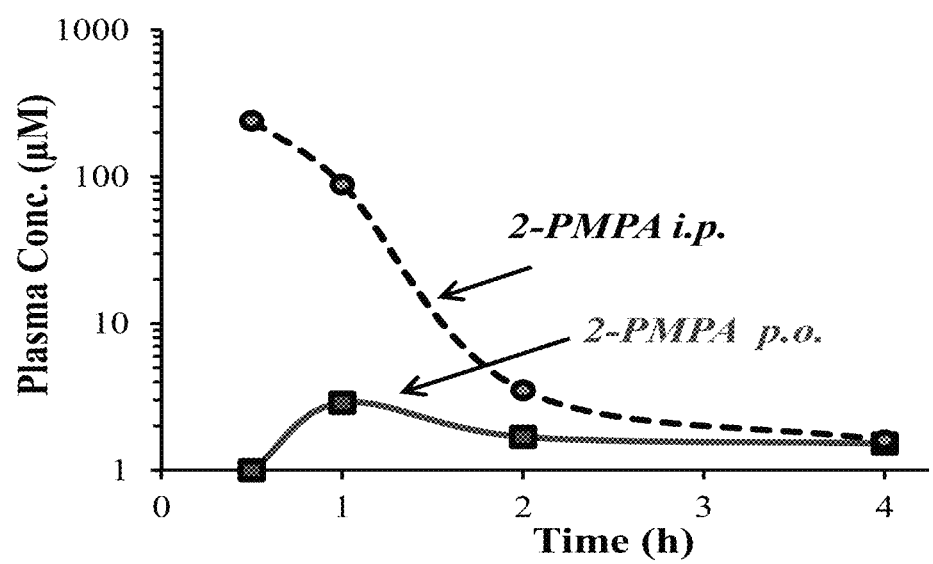

Having thus described the presently disclosed subject matter in general terms, reference will now be made to the accompanying Figures, which are not necessarily drawn to scale, and wherein:

FIG. 1 shows an example of the synthesis of Tris-POC (JAM0186);

FIG. 2 shows in vivo bioanalysis via method 1 (2-PMPA+ metabolites) and method 2 (2-PMPA selective);

FIG. 3 shows an embodiment of a representative screening paradigm;

FIG. 4 shows an in vitro metabolic stability screen of compound 1 in human and mouse plasma and liver subcellular fractions;

FIG. 5 shows an in vitro metabolic stability screen of compound 6 in mouse plasma and liver subcellular fractions;

FIG. 6 shows in vivo single time point pharmacokinetic studies of compounds 6, 7, and 8 in mice at 30 mg/kg equivalent 2-PMPA showing 30-50 fold enhancement in permeability;

FIG. 7 shows in vivo pharmacokinetic studies of compounds JHU 2109, JHU 2110, and JHU 2201 in mice (method 1), showing a greater then 50-fold increase of POM and POC prodrugs/metabolites following oral dosing;

FIG. 8 shows in vivo pharmacokinetic studies of compounds JHU 2109, JHU 2110, and JHU 2201 (method 2), indicating that POM and POC ester prodrugs do not release 2-PMPA because the methyl ester is too stable;

FIG. 9A and FIG. 9B show: (FIG. 9A) in vitro metabolic stability screens of compounds JHU 2236 and JHU 2237 in mouse plasma and liver subcellular fractions (method 1); (FIG. 9B) in vivo pharmacokinetic studies of compounds JHU 2236, JHU 2237, JHU 2263, JHU 2264, and JHU 2265 (methods 1 (total prodrug exposure) and 2 (2-PMPA release)), indicating that increasing ester chain length on carboxylates did not increase 2-PMPA release and no or minimal 2-PMPA release was observed with ethyl and propyl ester;

FIG. 10A and FIG. 10B show: (FIG. 10A) an in vivo single time point pharmacokinetic study of Tris-POM (compound JAM0168) in mice, indicating POM esters on carboxylate increases 2-PMPA approximately 18-fold following oral dosing; and (FIG. 10B) an in vivo single time point pharmacokinetic study of Tris-POM (compound JAM0168) in mice (11.69 mg/kg (equiv 2-PMPA); 30 min; N=3);

FIG. 11A and FIG. 11B show an in vitro metabolic stability screen of Tris-POC (compound JAM0186) in: (FIG. 11A) human and mouse plasma and liver subcellular fractions; and (FIG. 11B) human, dog, and monkey plasma and liver subcellular fractions;

FIG. 12 shows a single dose pharmacokinetic study in mice showing plasma 2-PMPA concentrations following 30 mg/kg per oral administration of Tris-POC (JAM0186; black circles) or 2-PMPA (red squares) (30 mg/kg (equiv 2-PMPA); 30 min; N=3);

FIG. 13 shows an in vitro metabolic stability screen of Tris-POC (JAM0186) in human, dog, and monkey plasma and liver subcellular fractions;

FIG. 14 shows a single dose in vivo full time course pharmacokinetic study of Tris-POC (JAM0186) in dogs (10 mg/kg (equiv 2-PMPA); N=1) showing a high Cmax;

FIG. 15 shows an in vitro metabolic stability screen of Tris-POC (JAM0186) and Tris-methyl-POC in human, dog, and monkey plasma and liver subcellular fractions;

FIG. 16 shows a marked increase of PSMA expression in the villous epithelium from ileal sample of CD patient (Zhang et al., 2012). Immunohistochemical localization of PSMA (indicated by arrows) in diseased ileal mucosa from the proximal margin of resected ileum from an ileal CD subject right panel) and a control non-IBD subject. Magnification is 100×. Bar is 200 mm;

FIG. 17 shows a marked elevation of PSMA functional enzymatic activity in the inflamed (diseased) intestinal mucosa of patients with IBD. PSMA activity was measured from mucosa specimens (n=32) from diseased (inflamed with active disease) and normal/uninvolved (macroscopically normal) mucosa from IBD patients or from non-IBD controls (healthy controls or patients with diverticulitis]. Note: PSMA is also highly upregulated in colon cancer;

FIG. 18 shows that PSMA inhibitor (PSMAi) ameliorates DNBS-induced colitis as effective as sulfasalazine (Sulfs), an IBD drug being currently used in the clinic. Mice receiving DNBS to induce colitis were treated simultaneously with either Sulfs, or PSMAi (100 mg/kg). Colon weight/body weight ratio, which positively correlated with the disease activity, was used as a measure for clinical activity;

FIG. 19 shows that PSMAi (2-PMPA) also ameliorates disease activity in DSS-induced murine model of colitis. C57/B6 mice (approximately 8 weeks old) that were induced to develop colitis with DSS (2.5%, 7 days in drinking water) were treated simultaneously with the vehicle or 2-PMPA (100 mg/kg), respectively. Disease activity index (DAI), which positively correlated with the disease severity, was used as a measure for clinical activity. * P<0.05;

FIG. 20 shows that PSMAi (2-PMPA) effectively suppresses PSMA activity in the colonic or cecal mucosa of DSS-induced murine model of colitis. PSMA activity was measured using extract from mucosa;

FIG. 21A, FIG. 21B, FIG. 21C and FIG. 21D show that PSMAi (2-PMPA) treatment leads to not only improvement of disease but even retraction of prolapse in IL-10 knockout (IL-10KO) mice that spontaneously develop colitis: (FIG. 21A) improvement of prolapse and colonic macroscopic disease (inflammation, hypertrophy, stool inconsistency); (FIG. 21B) body weight after 2-PMPA; (FIG. 21C) colon weight changes; and (FIG. 21D) prolapse retraction after treatment. IL-10 KO mice (C57/B6; 3 month old) were treated with 2-PMPA (100 mg/kg) for 2 weeks.* P<0.05;

FIG. 22 shows a flow-chart of an experimental design to address whether the PSMA inhibitor directly targets on colonic epithelial cells (CECs); CACO-2 cell lines or CECs isolated from WT and IL-10KO mice will be used;

FIG. 23A and FIG. 23B show the expression of CD103 on human intestinal DC: (FIG. 23A) FACS dot plot demonstrating identification of human colonic CD103+DC from biopsies and surgical resection tissue obtained from healthy controls or patients with active CD/UC (inflamed areas), via gating on viable cells according to forward and side scatter (not shown), HLA-DR versus lineage cocktail (CD3/CD14/CD16/CD19/CD34), and subsequent CD103 histogram; and (FIG. 23B) summary graph representing all experiments (control: n=14; IBD: n=8). T-test was applied ***p<0.001;

FIG. 24A, FIG. 24B, FIG. 24C and FIG. 24D show the expression of $\alpha_4\beta_7$ on murine intestinal DC: (FIG. 24A) FACS dot plot demonstrating identification of murine colonic CD103+DC as CD11c+MHC Class 11+ following gating on CD45+ live cells; (FIG. 24B) FACS dot plot demonstrating M407 co-expression with CD103 (markers were co-expressed in all experiments). Histogram was gated on CD45+ live cells, and subsequently MHC Class II+CD11c+ cells; (FIG. 24C) FACS histogram demonstrating example of $\alpha_4\beta_7$ expression on murine colonic DC. Histogram was gated on CD45+ live cells, and subsequently MHC Class II+CD11c+ cells; and (FIG. 24D) summary graph representing all experiments (n=3 for both). T-test was applied: *p<0.05;

FIG. 25 shows PK results with compound JAM0388 after dosing animals at 30 mg/kg equivalent of 2-PMPA by oral gavage and collecting brain and plasma samples at 30 min and 5 h. Brain and plasma samples were quantified for 2-PMPA using our previously published method (Rais et al, J Pharm Biomed Anal. 2014 January; 88:162-9). JAM0338 demonstrated excellent release of 2-PMPA in plasma and levels were quantifiable even at 5 h, showing sustained release of 2-PMPA from the prodrug. Brain levels were low at both time points;

FIG. 26 is a schematic illustration demonstrating that GCPII cleaves NAAG to NAA and glutamate in the brain;

FIG. 27 demonstrates that GCPII inhibition increases NAAG in the brain by >30 fold measured by microdialysis;

FIG. 28A, FIG. 28B and FIG. 28C demonstrate that 2-PMPA elevates NAAG and improves cognitive function in EAE mice. FIG. 28A demonstrates that mice show equal cognitive ability in Barnes maze paths on Day 1. FIG. 28B shows that on Day 4), EAE mice treated with vehicle show deficit on learning, while EAE mice treated with 2-PMPA have equal cognitive function to healthy control mice. FIG. 28C demonstrates that [NAAG] is elevated in EAE mice treated with 2PMPA; and FIG. 29 shows plasma concentration time profiles of 2-PMPA following i.p. (black line) and oral (red line) administration at 100 mg/kg in mice.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Prodrugs of 2-PMPA

2-PMPA is a highly polar compound with multiple carboxylates and a zinc binding phosphonate group and it has negligible oral availability. The usual way of solving this problem is by converting polar groups into less polar functional derivatives. However, typical prodrug approaches including simple alkyl esters of the acids such as methyl, ethyl, and propyl were attempted and were not successful, due to excess stability of these moieties on the carboxylates. Pivaloyloxymethyl (POM) and propyloxycarbonyloxymethyl (POC) on phosphonate groups demonstrated the right combination of lability in vitro and provided the highest levels of prodrug derived species when dosed orally. Even a compound with a free γ carboxylate demonstrated good bioavailability. However, none of these compounds released 2-PMPA in vivo to any appreciable extent. The presently disclosed subject matter shows that POM and POC on the bis phosphonate and the alpha carboxylate were ideal for enhancing the permeability (approximately 20 fold), as well as release of the parent compound upon oral dosing.

Structures of representative structures of 2-PMPA prodrugs are provided in Table 1. More particularly, the presently disclosed subject matter includes the capping of the acidic functional groups of 2-PMPA. In some embodiments, the carboxylic acid groups of 2-PMPA were protected with alkyl esters. See for example, compounds 1, 2, and 3 of Table 1. These carboxylic esters, however, unexpectedly were too stable in vivo to be effective prodrugs. Protecting the phosphonate of 2-PMPA with for example bis-POM (compound 4) or bis-POC (compound 5) while leaving the carboxylates free, however, was not a feasible solution because of the chemical instability of such derivatives.

A combination of both approaches, i.e., protecting the carboxylic acid groups with an alkyl ester and protecting the phosphonate with POM or POC, e.g., compounds 6 and 7, provided compounds that exhibited good permeability. These compounds, however, were only converted to the corresponding carboxylate ester, compound 1, which is stable in plasma and did not exhibit the ability to release 2-PMPA.

Compounds including POM and POC on the bis-phosphonate of 2-PMPA and an alkyl ester on the α-carboxylate, with a free γ-carboxylate, e.g., compounds 8 and 9, exhibited good oral availability, but were only converted to monoester 10.

The stability of the simple carboxylic ester, however, can be overcome by introducing another POC or POM moiety on the α-carboxylate (compounds 11 and 12, respectively). Such compounds exhibited sufficient chemical stability, yet exhibited the potential to release 2-PMPA.

TABLE 1

Structures of Representative 2-PMPA Prodrugs and Metabolic Products

| IOCB No./<br>Compound No. | Structure | MW |
|---|---|---|
| 2-PMPA | | 226.12 |
| 1<br>TT-140113<br>JHU 2106 | | 254.17 |
| 2<br>MK-797<br>JHU 2236 | | 282.23 |
| 3<br>MK-801<br>JHU 2263 | | 310.28 |

TABLE 1-continued

Structures of Representative 2-PMPA Prodrugs and Metabolic Products

| IOCB No./ Compound No. | Structure | MW |
|---|---|---|
| 4 | | 458.35 |
| 5 | | 454.41 |
| 6<br>TT-010213<br>JHU 2110 | | 486.41 |
| 7<br>MK-793<br>JHU 2234 | | 472.38 |
| 8<br>TT-150313<br>JHU 2201 | | 468.43 |

TABLE 1-continued

Structures of Representative 2-PMPA Prodrugs and Metabolic Products

| IOCB No./Compound No. | Structure | MW |
|---|---|---|
| 9 | 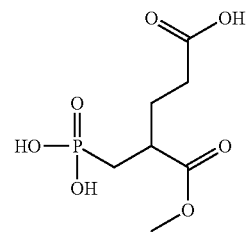 | 240.15 |
| 10 JAM0186 2-PMPATRIS-POC | | 574.47 |
| 11 | 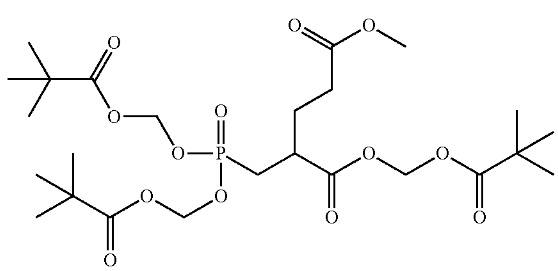 [SMILES: COC(=O)CCC(CP(=O)(OCOC(=O)C(C)(C)C)OCOC(=O)C(C)(C)C)C(=O)OCOC(=O)C(C)(C)C] | 582.57 |
| 12 TT-041212 JHU 2107 | | 791.13 |

TABLE 1-continued
Structures of Representative 2-PMPA Prodrugs and Metabolic Products
| IOCB No./ Compound No. | Structure | MW |
|---|---|---|
| 13<br>TT-250113<br>JHU 2108 | 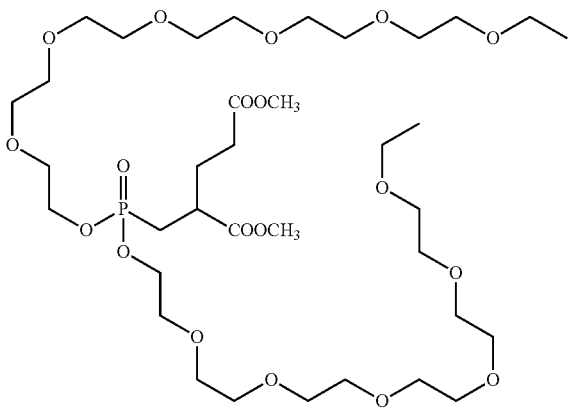 [SMILES: CCOCCOCCOCCOCCOCCOCCOP(=O)(CC(CCC(=O)OC)C(=O)OC)OCCOCCOCCOCCOCCOCCOCC] | 838.90 |
| 14<br>TT-201212A<br>JHU 2109 | 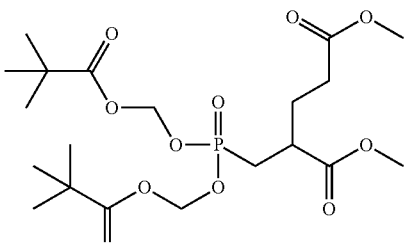 | 482.46 |
| 15<br>TT-010213<br>JHU 2110 | 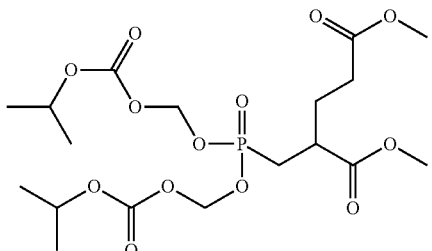 | 486.40 |
| 16<br>TT-100113<br>JHU 2111 | 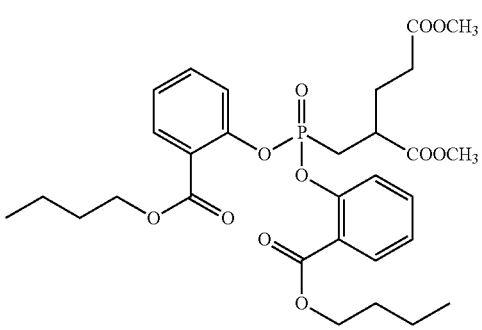 [SMILES: CCCCOC(=O)c1ccccc1OP(=O)(CC(CCC(=O)OC)C(=O)OC)Oc1ccccc1C(=O)OCCCC] | 606.58 |

TABLE 1-continued

Structures of Representative 2-PMPA Prodrugs and Metabolic Products

| IOCB No./ Compound No. | Structure | MW |
| --- | --- | --- |
| 17 TT-280113 JHU 2112 | 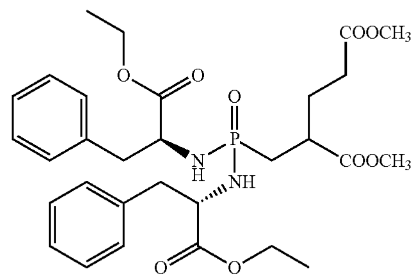 [SMILES: CCOC(=O)[C@H](Cc1ccccc1)NP(=O)(CC(CCC(=O)OC)C(=O)OC)N[C@@H](Cc1ccccc1)C(=O)OCC] | 604.60 |
| 18 MK798 JHU 2237 | 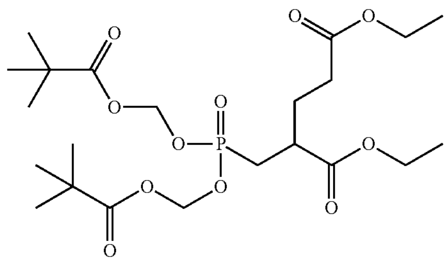 [SMILES: CCOC(=O)CCC(CP(=O)(OCOC(=O)C(C)(C)C)OCOC(=O)C(C)(C)C)C(=O)OCC] | 510.51 |
| 19 MK804 JHU 2264 | 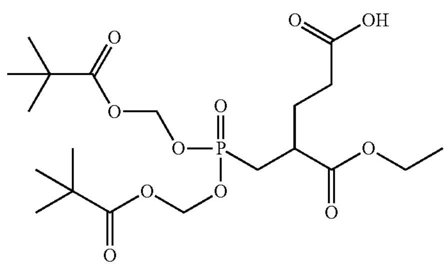 [SMILES: CCOC(=O)C(CCC(=O)O)CP(=O)(OCOC(=O)C(C)(C)C)OCOC(=O)C(C)(C)C] | 482.46 |
| 20 MK806 JHU 2265 | 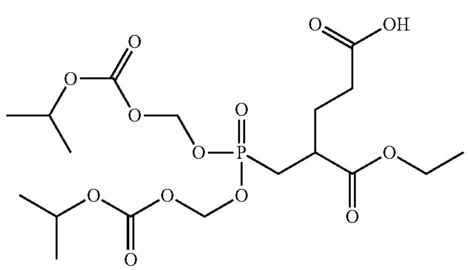 [SMILES: CCOC(=O)C(CCC(=O)O)CP(=O)(OCOC(=O)OC(C)C)OCOC(=O)OC(C)C] | 486.40 |
| 21 MK-795 JHU 2235 | 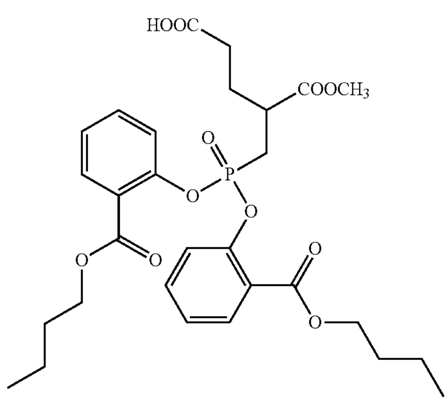 [SMILES: CCCCOC(=O)c1ccccc1OP(=O)(CC(CCC(=O)O)C(=O)OC)Oc1ccccc1C(=O)OCCCC] | 592.57 |

TABLE 1-continued

Structures of Representative 2-PMPA Prodrugs and Metabolic Products

| IOCB No./ Compound No. | Structure | MW |
|---|---|---|
| 22 MK-799 JHU 2238 | 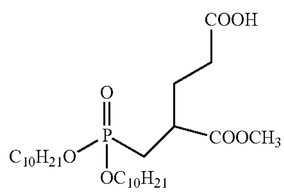 | 520.68 |
| 23 JAM0168 2-PMPA TRIS POM | 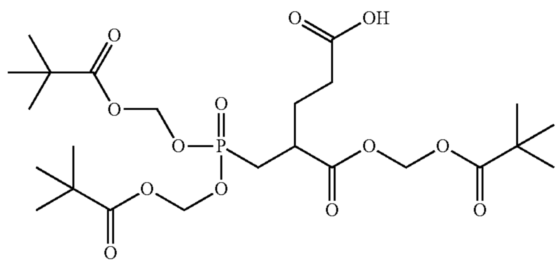 [SMILES: CC(C)(C)C(=O)OCOC(=O)C(CCC(=O)O)CP(=O)(OCOC(=O)C(C)(C)C)OCOC(=O)C(C)(C)C] | 568.55 |
| 24 JAM0195 JHU 2609 | 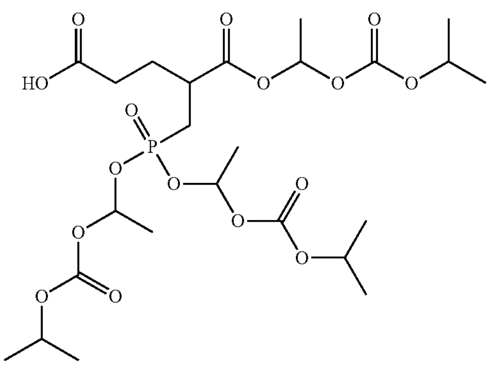 [SMILES: CC(C)OC(=O)OC(C)OC(=O)C(CCC(=O)O)CP(=O)(OC(C)OC(=O)OC(C)C)OC(C)OC(=O)OC(C)C] | 616.55 |
| 25 JAM0191 JHU 2608 | 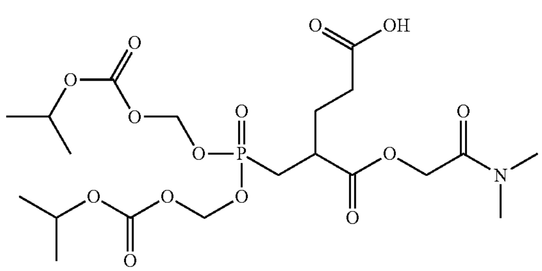 [SMILES: CC(C)OC(=O)OCOP(=O)(CC(CCC(=O)O)C(=O)OCC(=O)N(C)C)OCOC(=O)OC(C)C] | 543.46 |
| 26 JAM0196 JHU 2610 | 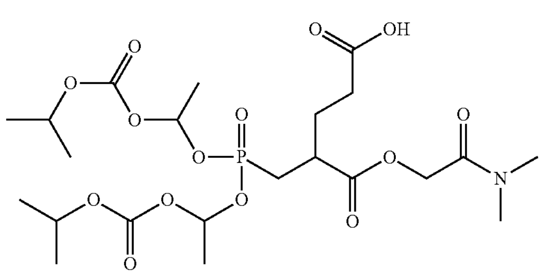 [SMILES: CC(C)OC(=O)OC(C)OP(=O)(CC(CCC(=O)O)C(=O)OCC(=O)N(C)C)OC(C)OC(=O)OC(C)C] | 571.51 |

TABLE 1-continued
Structures of Representative 2-PMPA Prodrugs and Metabolic Products
| IOCB No./ Compound No. | Structure | MW |
|---|---|---|
| 27 LTP023 | 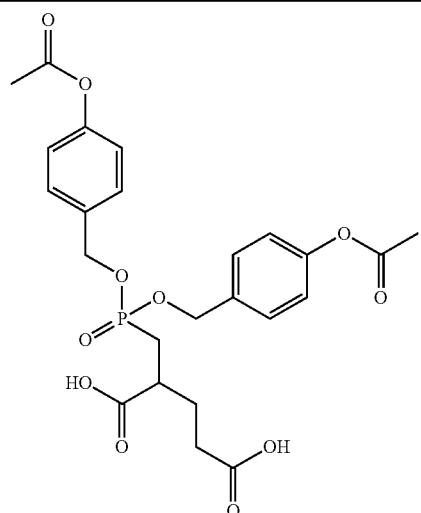 | 522.44 |
| 28 LTP120 | 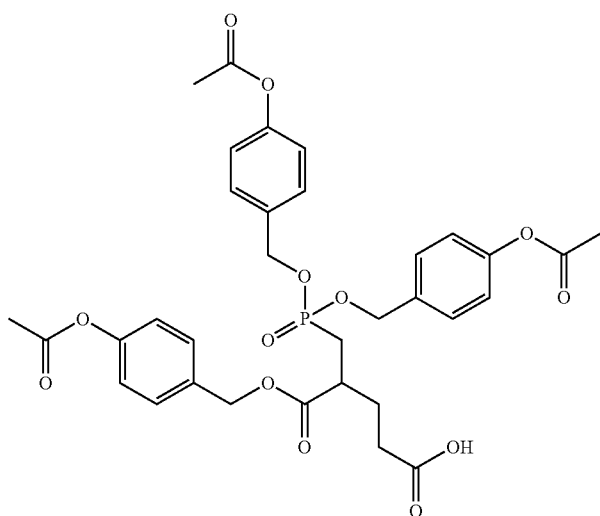 [SMILES: CC(=O)Oc1ccc(COC(=O)C(CCC(=O)O)CP(=O)(OCc2ccc(OC(C)=O)cc2)OCc2ccc(OC(C)=O)cc2)cc1] | 670.60 |
| 29 LTP124 | 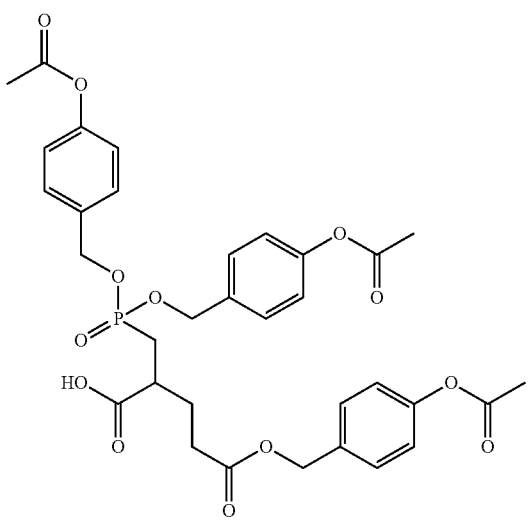 [SMILES: CC(=O)Oc1ccc(COC(=O)CCC(CP(=O)(OCc2ccc(OC(C)=O)cc2)OCc2ccc(OC(C)=O)cc2)C(=O)O)cc1] | 670.60 |

TABLE 1-continued

Structures of Representative 2-PMPA Prodrugs and Metabolic Products

| IOCB No./Compound No. | Structure | MW |
|---|---|---|
| 30 JAM0388H | 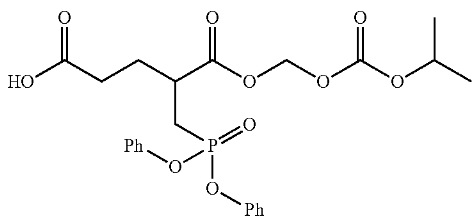 [SMILES: CC(C)OC(=O)OCOC(=O)C(CCC(=O)O)CP(=O)(Oc1ccccc1)Oc1ccccc1] | 494.43 |
| 31 JAM0341H | 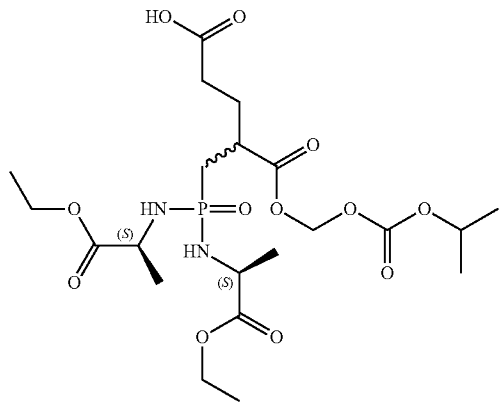 | 540.50 |
| 32 TT-120814 | 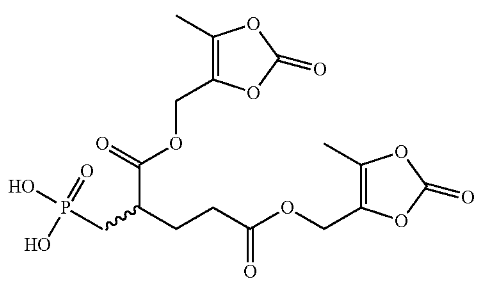 [SMILES: Cc1oc(=O)oc1COC(=O)CCC(CP(=O)(O)O)C(=O)OCc1oc(=O)oc1C] | 450.29 |
| 33 TT-200714 | 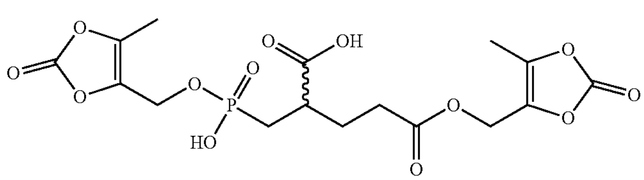 [SMILES: Cc1oc(=O)oc1COC(=O)CCC(CP(=O)(O)OCc1oc(=O)oc1C)C(=O)O] | 450.29 |
| 34 TT-270514 | 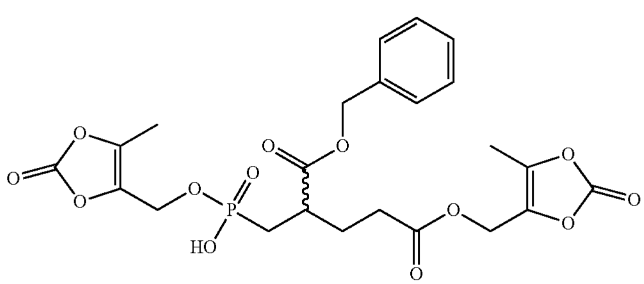 [SMILES: Cc1oc(=O)oc1COC(=O)CCC(CP(=O)(O)OCc1oc(=O)oc1C)C(=O)OCc1ccccc1] | 540.41 |

TABLE 1-continued

Structures of Representative 2-PMPA Prodrugs and Metabolic Products

| IOCB No./Compound No. | Structure | MW |
|---|---|---|
| 35 TT-011214 | 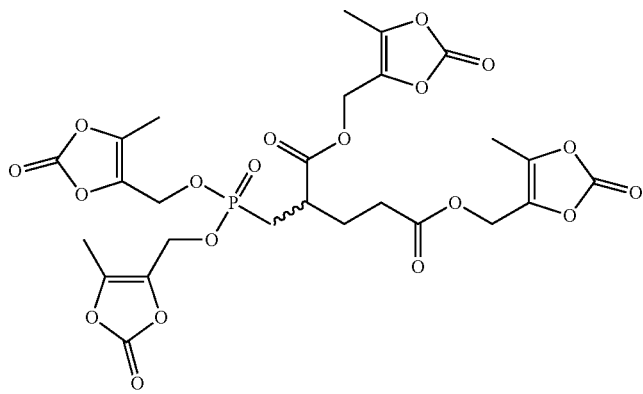 [SMILES: Cc1oc(=O)oc1COC(=O)CCC(CP(=O)(OCc1oc(=O)oc1C)OCc1oc(=O)oc1C)C(=O)OCc1oc(=O)oc1C] | 674.45 |
| 36 TT-110814A | 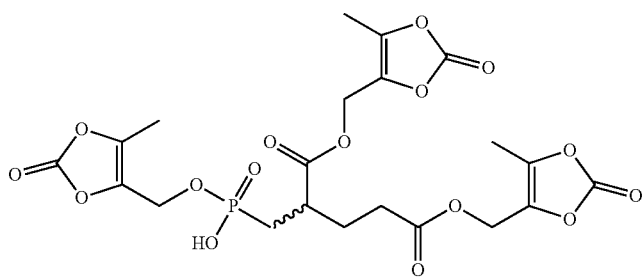 [SMILES: Cc1oc(=O)oc1COC(=O)CCC(CP(=O)(O)OCc1oc(=O)oc1C)C(=O)OCc1oc(=O)oc1C] | 562.37 |

In yet other embodiments, fine tuning of the hydrolysis rate can be evaluated by a combination of POC and methyl-substituted POC, as illustrated by the following compounds:

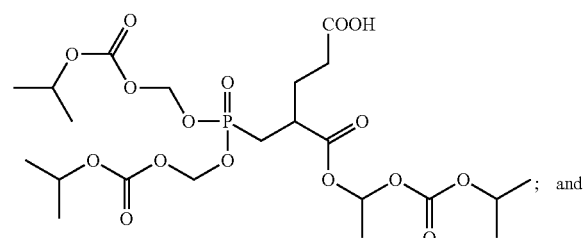

; and

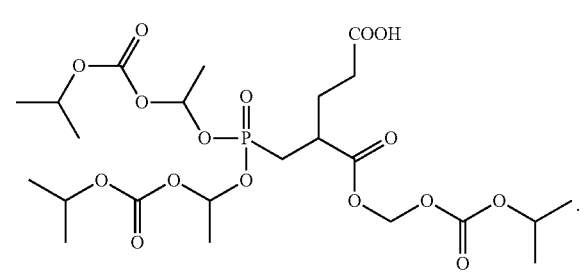

.

Further directions in 2-PMPA prodrugs include the following approach, including more easily hydrolysable phenyl esters; anhydrides, and dioxolone esters employing paraoxonase for bioconversion:

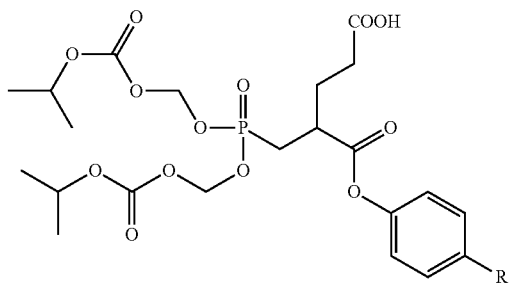

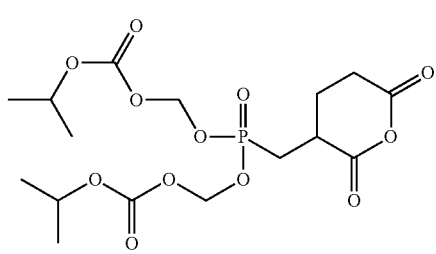

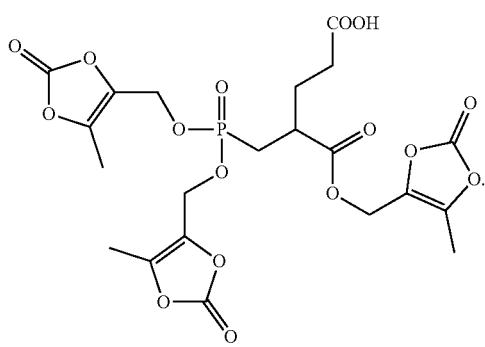

Additionally, the following dioxolone esters and anhydride prodrugs of 2-PMPA are contemplated:

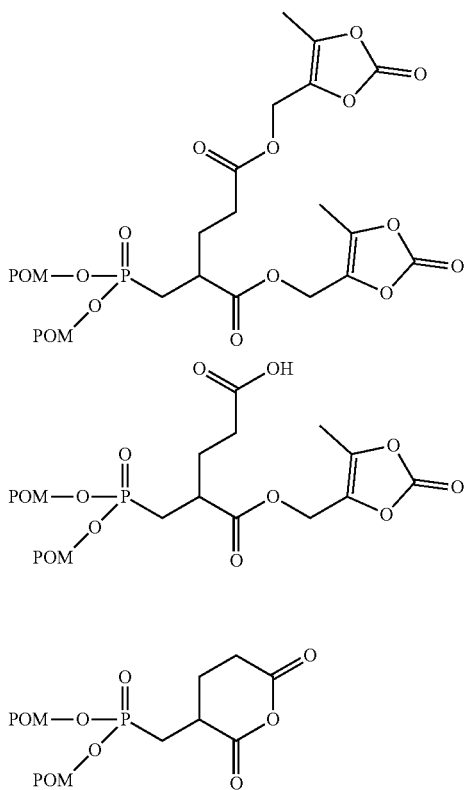

Further examples of alternative carboxy-esters prodrugs of 2-PMPA also include:

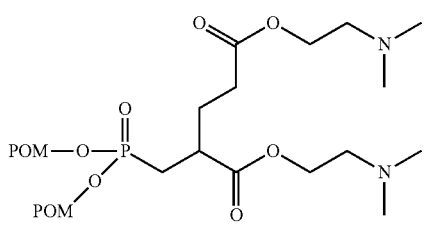

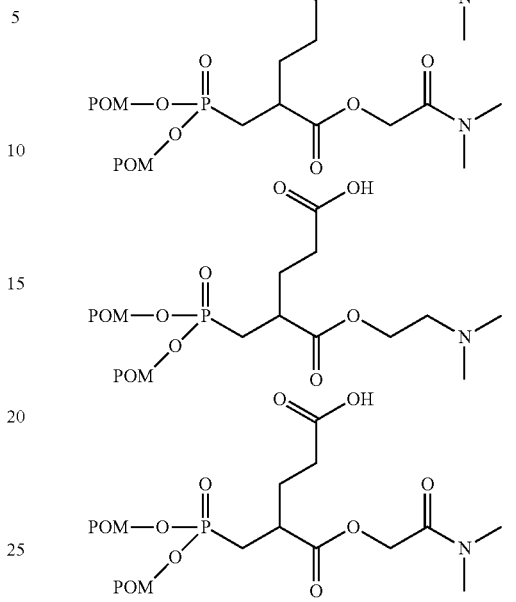

Accordingly, in some embodiments, the presently disclosed subject matter provides a compound of formula (I) or formula (II):

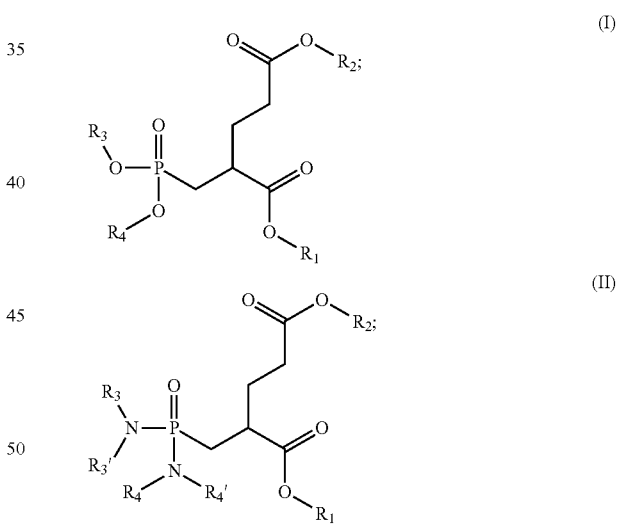

wherein:

each $R_1$, $R_2$, $R_3$, and $R_4$ is independently selected from the group consisting of H, alkyl, Ar, —$(CR_5R_6)_n$—Ar, —$(CR_5R_6)_n$—O—C(=O)—$R_7$, —$(CR_5R_6)_n$—C(=O)—O—$R_7$, —$(CR_5R_6)_n$—O—C(=O)—O—$R_7$, —$(CR_5R_6)_n$—O—$R_7$, —$(CR_5R_6)_n$—O—$[(CR_5R_6)_n$—O$]_m$—$R_7$, —$(CR_5R_6)_n$—Ar—O—C(=O)—$R_7$, —Ar—C(=O)—O—$(CR_5R_6)_n$—$R_7$, —$(CR_5R_6)_n$—$NR_8R_9$, and —$(CR_5R_6)_n$—C(=O)—$NR_8R_9$;

wherein:

n is an integer from 1 to 20;

m is an integer from 1 to 20;

each $R_3'$ and $R_4'$ are independently H or alkyl;

each $R_5$ and $R_6$ is independently selected from the group consisting of H, alkyl, and alkylaryl;

each $R_7$ is independently straightchain or branched alkyl;

Ar is aryl, substituted aryl, heteroaryl or substituted heteroaryl; and $R_8$ and $R_9$ are each independently H or alkyl; and pharmaceutically acceptable salts thereof.

In particular embodiments, the compound of formula (I) is selected from the group consisting of:

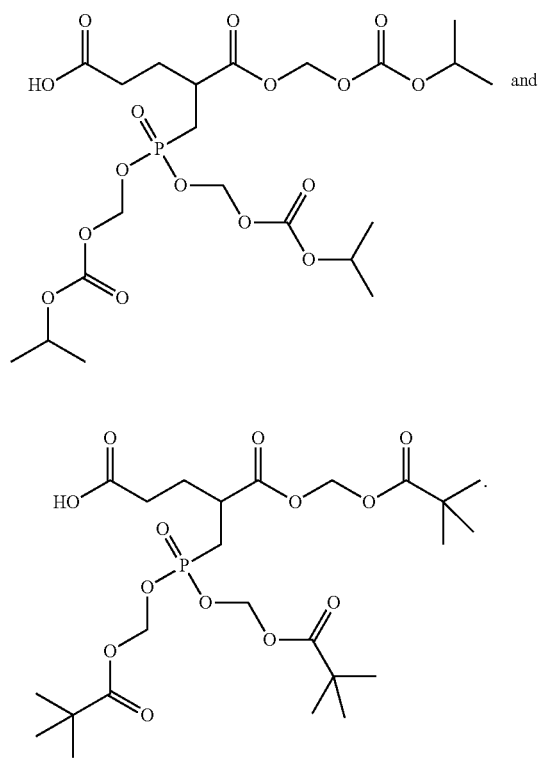

In particular embodiments, the compound of formula (I) is selected from the group consisting of:

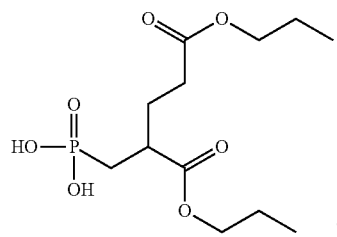

In particular embodiments, the compound of formula (I) is selected from the group consisting of:

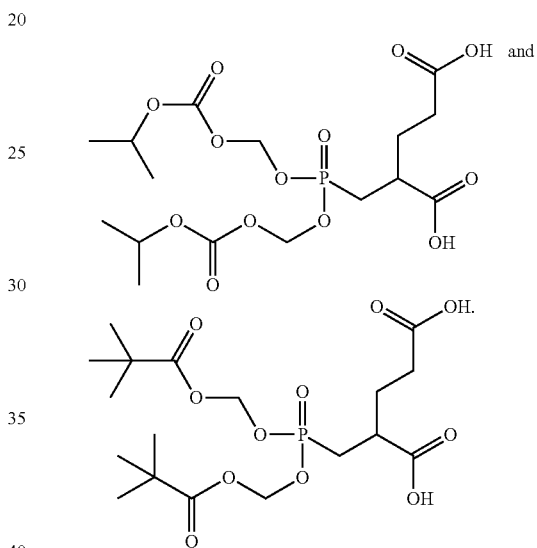

In particular embodiments, the compound of formula (I) is selected from the group consisting of:

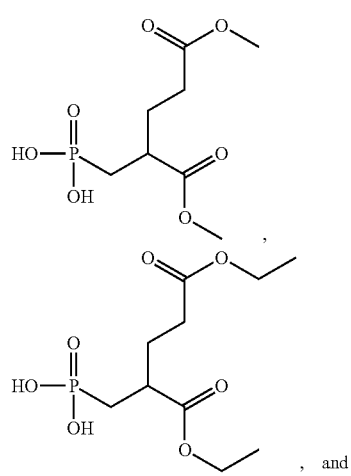

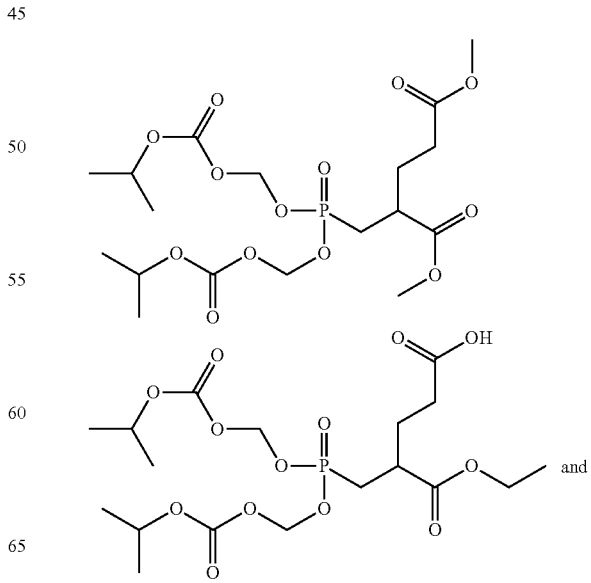

-continued

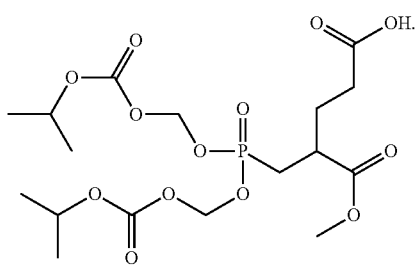

In particular embodiments, the compound of formula (I) is

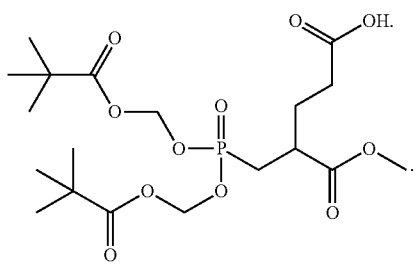 [SMILES: COC(=O)C(CCC(=O)O)CP(=O)(OCOC(=O)C(C)(C)C)OCOC(=O)C(C)(C)C ; "."]

In particular embodiments, the compound of formula (I) is

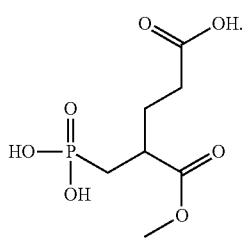

In particular embodiments, the compound of formula (I) is

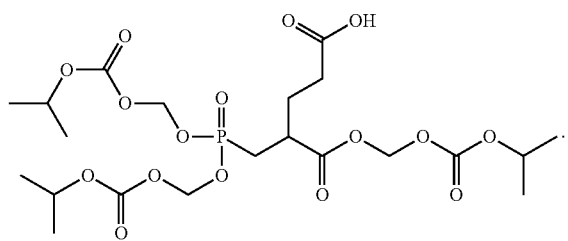 [SMILES: CC(C)OC(=O)OCOC(=O)C(CCC(=O)O)CP(=O)(OCOC(=O)OC(C)C)OCOC(=O)OC(C)C ; "."]

In particular embodiments, the compound of formula (I) is

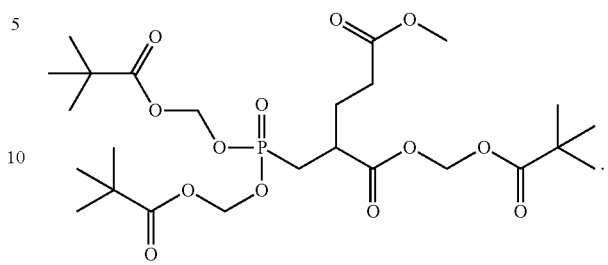

In particular embodiments, the compound of formula (I) is

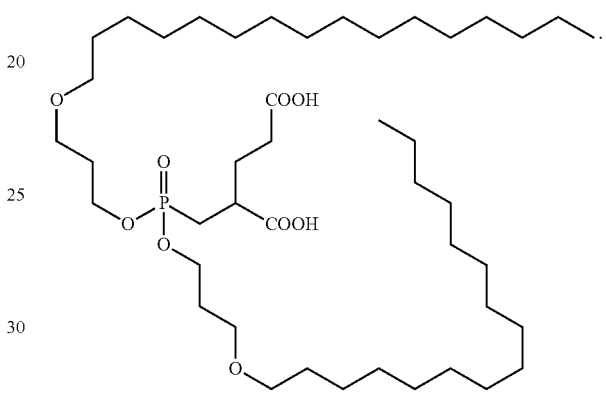

In particular embodiments, the compound of formula (I) is

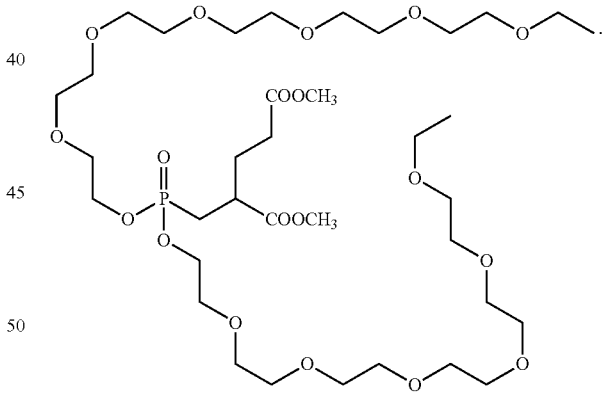

In particular embodiments, the compound of formula (I) is selected from the group consisting of:

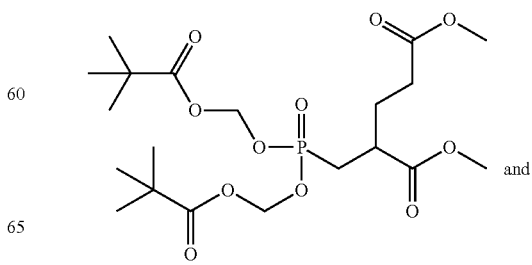

and

-continued

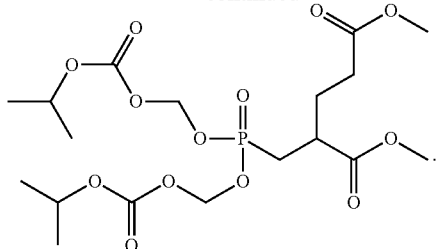

In particular embodiments, the compound of formula (I) is

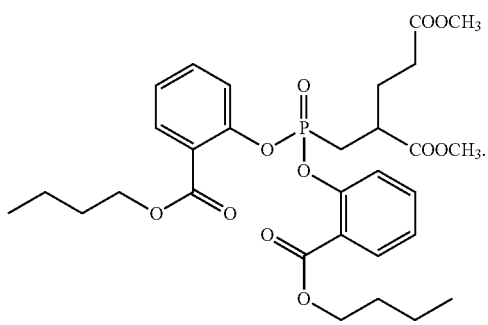 [SMILES: CCCCOC(=O)c1ccccc1OP(=O)(CC(CCC(=O)OC)C(=O)OC)Oc1ccccc1C(=O)OCCCC]

In particular embodiments, the compound of formula (I) is

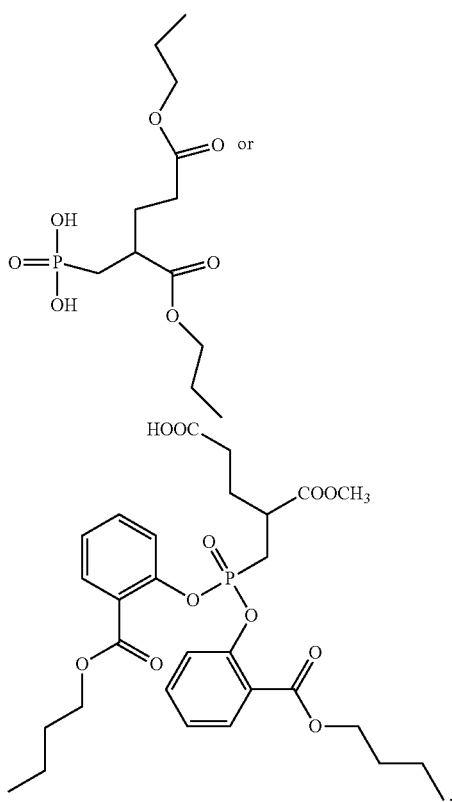

In particular embodiments, the compound of formula (I) is selected from the group consisting of:

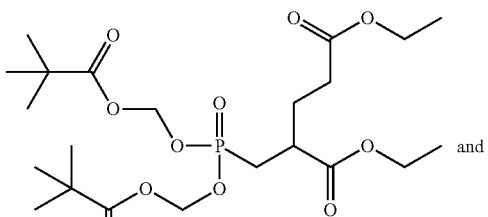

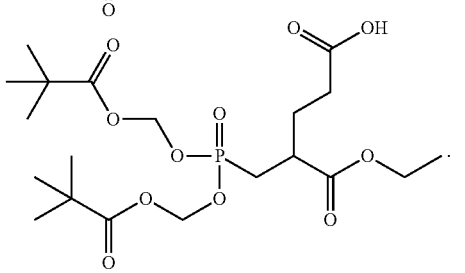

In particular embodiments, the compound of formula (I) is

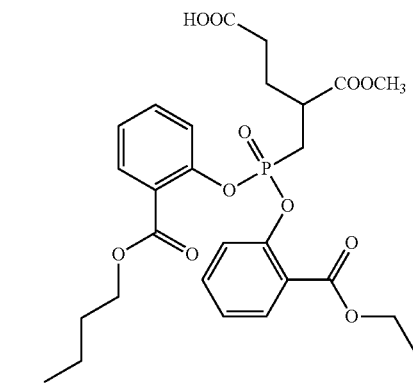

In particular embodiments, the compound of formula (I) is

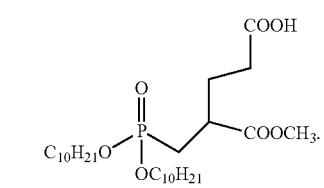

In particular embodiments, the compound of formula (I) is

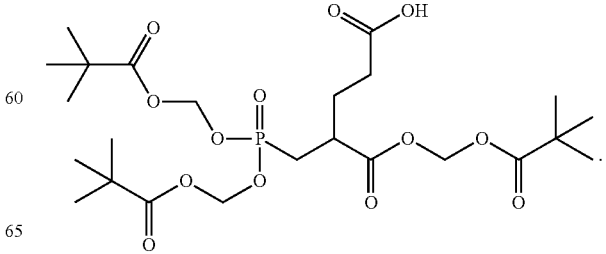

In particular embodiments, the compound of formula (I) is
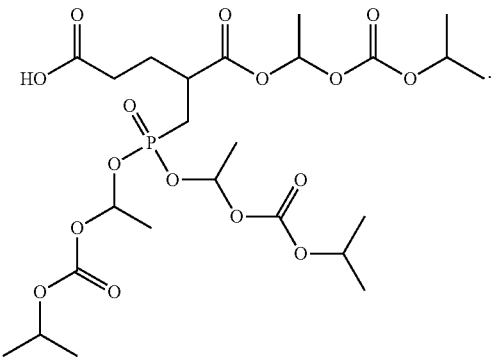 [SMILES: CC(C)OC(=O)OC(C)OC(=O)C(CCC(=O)O)CP(=O)(OC(C)OC(=O)OC(C)C)OC(C)OC(=O)OC(C)C]
In particular embodiments, the compound of formula (I) is selected from the group consisting of.
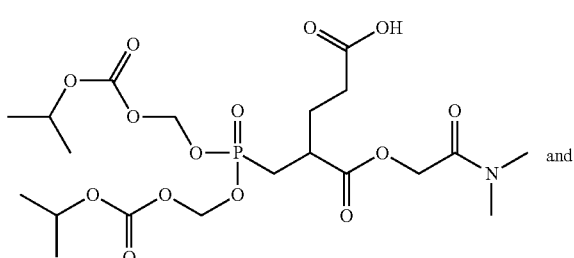
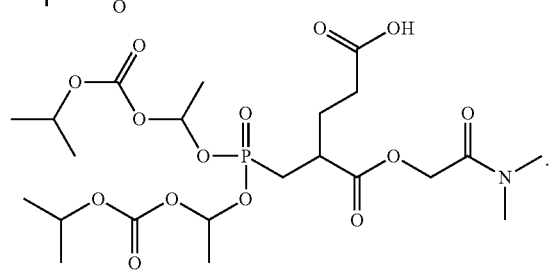
In particular embodiments, the compound of formula (I) is selected from the group consisting of:
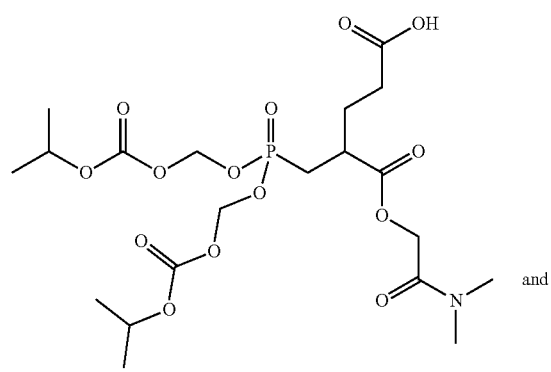
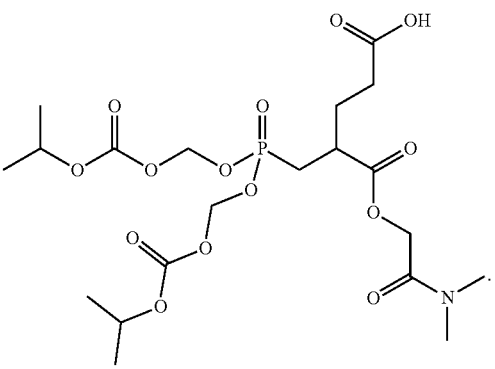
In particular embodiments, the compound of formula (I) is selected from the group consisting of:
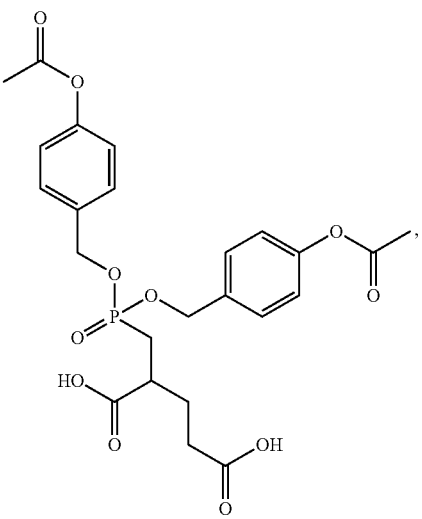
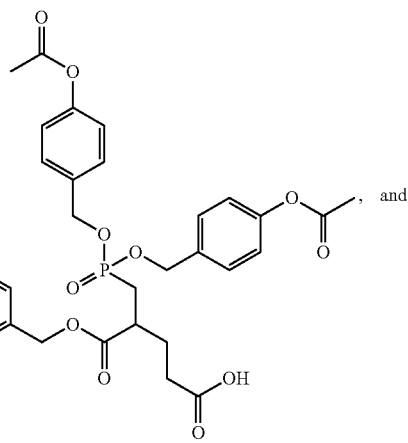

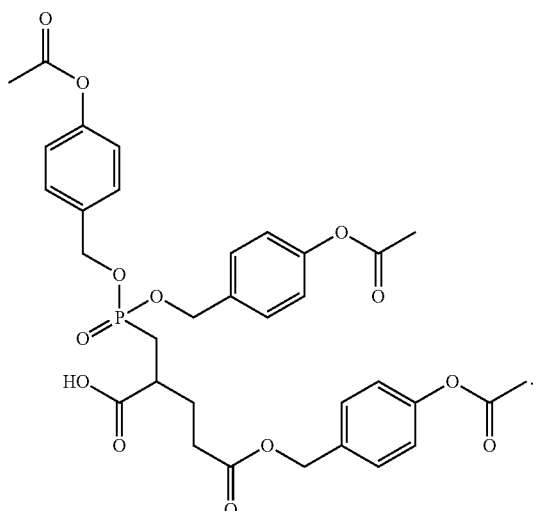
In particular embodiments, the compound of formula (I) is
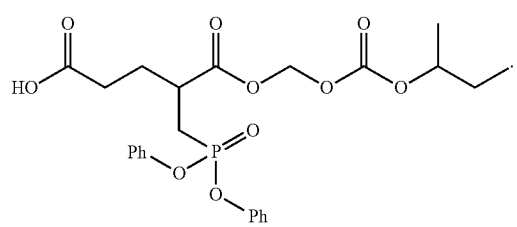
In particular embodiments, the compound of formula (I) is selected from the group consisting of:
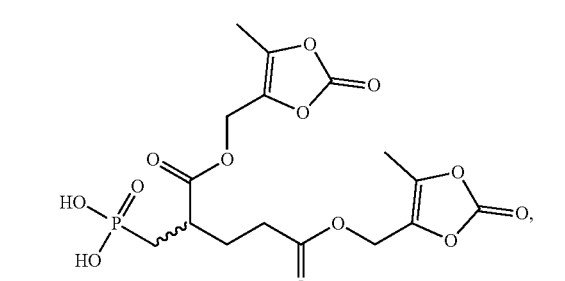
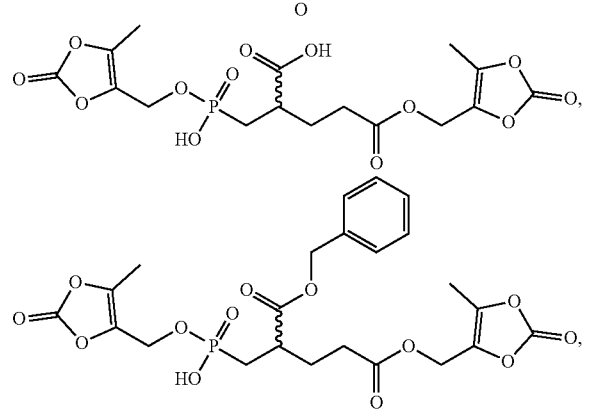
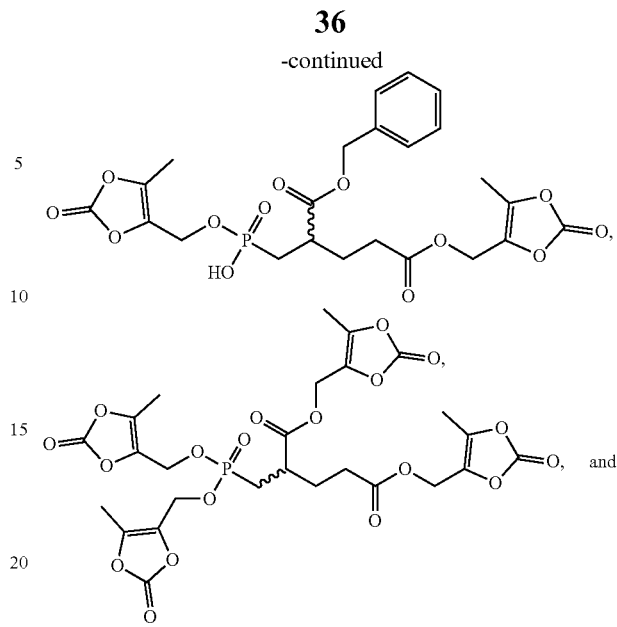
In particular embodiments, the compound of formula (II) is
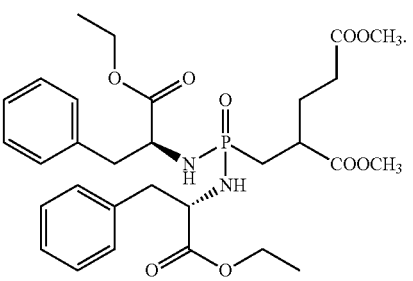 [SMILES: CCOC(=O)[C@H](Cc1ccccc1)NP(=O)(CC(CCC(=O)OC)C(=O)OC)N[C@@H](Cc1ccccc1)C(=O)OCC]
In particular embodiments, the compound of formula (II) is
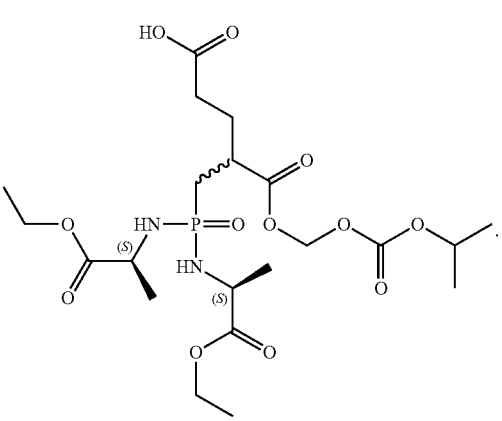

II. Pharmaceutical Compositions and Administration

In another aspect, the present disclosure provides a pharmaceutical composition including a compound of formula (I), or a compound of formula (II), alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

III. Methods for Treating a Disease or Disorder

The presently disclosed compounds, which are orally bioavailable prodrugs of 2-PMPA, allow a clinically acceptable dosing paradigm for diseases or conditions wherein excess PSMA/GCPII activity is implicated. These diseases or conditions include, but are not limited to, neurodegenerative disease such as amyotrophic lateral sclerosis (ALS), Parkinson's disease (PD), Alzheimer's disease (AD), Huntington's disease, dementia with Lewy Bodies (DLB), schizophrenia, pain, epilepsy, stroke, and traumatic brain injury (TBI), as well as multiple sclerosis (MS), cancer, angiogenesis and inflammatory bowel disease. As used herein, a "neurodegenerative disease" is a disease or condition that results in the progressive loss of the structure and/or function of neurons in a subject.

As used herein, the terms "PSMA" or "PSMA polypeptide" refer to a naturally occurring or endogenous PSMA and to proteins having an amino acid sequence which is the same as that of a naturally occurring or endogenous PSMA (e.g., recombinant proteins). Accordingly, as defined herein, the term includes mature PSMA, glycosylated or unglycosylated PSMA proteins, polymorphic or allelic variants, and other isoforms of PSMA (e.g., produced by alternative splicing or other cellular processes).

As used herein, an "inhibitor" of PSMA is a molecule that decreases or inhibits the activity of PSMA when administered. The inhibitor may interact with PSMA directly or may interact with another molecule that results in a decrease in the activity of PSMA.

The presently disclosed subject matter shows that there is a marked elevation or excess of PSMA activity in subjects with certain diseases or conditions. As used herein, the term "excess PSMA activity" means an increase of PSMA activity in a subject with a disease or condition as compared to the PSMA activity in a subject without a similar disease or condition, such as an increase of approximately 100%, 200%, 300%, 400%, 500%, 600%, 700%, 800%, 900%, 1000%, or more.

In some embodiments, the presently disclosed subject matter provides methods for inhibiting the excess PSMA activity found in a subject with a disease or condition. As used herein, the term "inhibit" means to decrease or diminish the excess PSMA activity found in a subject. The term "inhibit" also may mean to decrease, suppress, attenuate, diminish, arrest, or stabilize the development or progression of a disease or condition. Inhibition may occur, for e.g., by at least 10%, 20%, 30%, 40%, 50%, 60%, 70%, 80%, 90%, 95%, 98%, 99%, or even 100% compared to an untreated control subject or a subject without the disease or disorder.

In general, the presently disclosed methods result in a decrease in the severity of a disease or condition in a subject. The term "decrease" is meant to inhibit, suppress, attenuate, diminish, arrest, or stabilize a symptom of a disease or condition.

As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

Accordingly, in some embodiments, the presently disclosed subject matter provides a method for treating a disease or a condition, the method comprising administering to a subject in need of treatment thereof, a compound of formula (I), a compound of formula (II), or a pharmaceutical composition thereof, in an amount effective for treating the disease or condition.

In particular embodiments, the disease or condition is selected from the group consisting of a neurodegenerative disease, multiple sclerosis (MS), cancer, angiogenesis, and inflammatory bowel disease.

In certain embodiments, the neurodegenerative disease is selected from the group consisting of amyotrophic lateral sclerosis (ALS), Parkinson's disease (PD), Alzheimer's disease (AD), Huntington's disease, dementia with Lewy Bodies (DLB), schizophrenia, pain, epilepsy, stroke, and traumatic brain injury (TBI).

In some embodiments, the disease or condition results in excess PSMA activity. In such aspects, the method further comprises inhibiting the excess PSMA activity when the compound of formula (I), the compound of formula (II), or a pharmaceutical composition thereof, is administered.

IV. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —$C(\!=\!O)O$— is equivalent to —$OC(\!=\!O)$—; —$OC(\!=\!O)$NR— is equivalent to —$NRC(\!=\!O)O$—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{2}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$CH_2CH_2CH_2CH_2$—, —$CH_2$CH=CHCH$_2$—, —$CH_2$CsCCH$_2$—, —$CH_2CH_2$CH($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'- and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

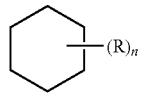

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

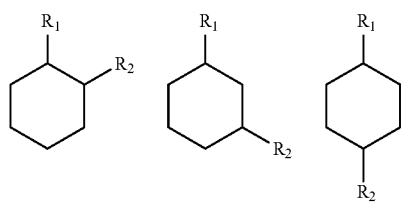

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from/zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'"taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to —SH.

The term ureido refers to a urea group of the formula —NH—CO—$NH_2$.

Unless otherwise explicitly defined, a "substituent group," as used herein, includes a functional group selected from one or more of the following moieties, which are defined herein:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

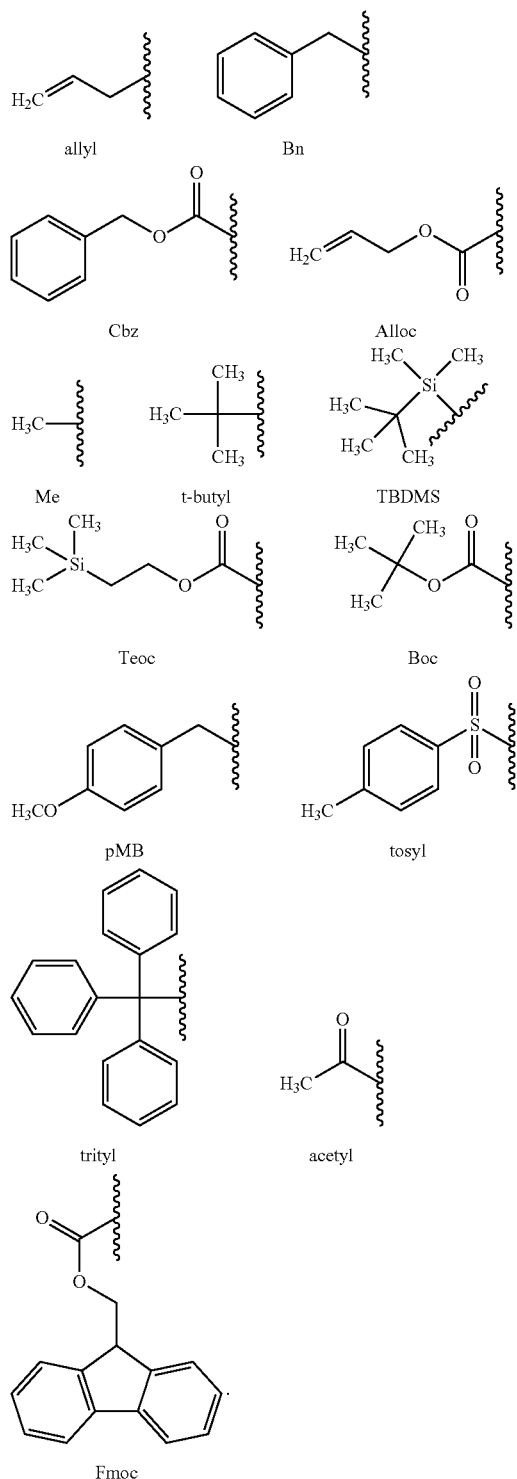

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

In Vitro Stability Studies: The stock solution for most prodrugs was prepared as a 10 mM solution in DMSO except JHU 2107, which was solubilized in THF (tetrahydrofuran) to carry out the in vitro studies.

The chemical stability of prodrugs was evaluated using simulated gastric fluid (pH 1.2) and Hanks' Balanced Salt Solution (HBSS) buffer (pH 7.4). Briefly, prodrugs were spiked (10 μM) in respective solutions and incubated at 37° C. for 1 h. At predetermined time points (0, 30 and 60 min), aliquots of 100 μL were removed and diluted with 100 μL of water. Prodrug disappearance was monitored using the developed liquid chromatography and tandem mass spectrometry (LC/MS/MS) method described below.

For metabolic stability, plasma (mouse, dog, monkey and human) and liver microsomes (mouse, dog, monkey and human) were used. For stability, prodrugs (10 μM) were spiked in each matrix and incubated in an orbital shaker at 37° C. At predetermined times (0, 30 and 60 min), 100 μL aliquots of the mixture in triplicate were removed and the reaction quenched by addition of three times the volume of ice cold acetonitrile spiked with the internal standard (losartan 5 μM). The samples were vortexed for 30 s and centrifuged 12000 g for 10 min. 50 μL supernatant diluted with 50 μL water was transferred to a 250 μL polypropylene vial sealed with a Teflon cap. Prodrug disappearance was monitored over time using a liquid chromatography and tandem mass spectrometry (LC/MS/MS) method as described below.

For LC/MS/MS, prodrugs were separated with Thermo Scientific Accela UPLC system coupled to Accela open autosampler on an Agilent C18 (100×2.1 mm id) UPLC column. The autosampler was temperature controlled and operating at 10° C. The mobile phase used for the chromatographic separation was composed of acetonitrile/water containing 0.1% formic acid and was run at a flow rate of 0.5 mL/minute for 4.5 minutes using gradient elution. The column effluent was monitored using TSQ Vantage triple-quadrupole mass spectrometric detector, equipped with an electrospray probe set in the positive ionization mode. Samples were introduced into the ionization source through a heated nebulized probe (350° C.).

For quantification of compound remaining, disappearance of prodrugs was measured from ratio of peak areas of analyte to IS. Percentage remaining was calculated in the following manner:

$$\frac{\text{Avg. Response} * @ 60 \min}{\text{Avg. Response} @ 0 \min} \times 100$$

where response=[(Area of analyte)/(Area of internal standard)]

*Average response is average of two samples at each time point.

In Vivo Pharmacokinetics of 2-PMPA Prodrugs in Rodent (Mice) and Non-Rodent (Dogs) Species: Prodrugs were dosed peroral (30 mg/kg equiv. 2-PMPA) in mice at a dosing volume of 1 mL/kg. Blood was obtained via cardiac puncture and tissue dissected at 0 min, 15 min, 30 min, 1 h, 2 h, and 4 h post dose (n=3 per time point). Single time point studies were conducted at 30 min (N=3) following dosing. Plasma was harvested from blood by centrifugation. Mean concentration-time data was used for pharmacokinetic (PK) analysis. Non-compartmental-analysis module in WinNonlin® (version 5.3) was used to assess pharmacokinetic parameters. Peak plasma concentrations ($C_{max}$) and time to $C_{max}$ ($T_{max}$) were the observed values. Area under the curve (AUC) was calculated by log-linear (p.o.) trapezoidal rule to the end of sample collection (AUClast) and extrapolated to infinity ($AUC_{0-\infty}$) by dividing the last quantifiable concentration by the terminal disposition rate constant ($k_e$). Terminal half-life ($t_{1/2}$) was estimated from first order kinetics: $t_{1/2}=0.693/k_e$. The goal was to find prodrugs yielding oral bioavailability % F≥30%.

For pharmacokinetics in beagle dogs, animals were dosed with 2-PMPA prodrug (10 mg/kg equivalent 2-PMPA) p.o. (by mouth). Blood samples were collected from the jugular vein (~1 mL) via direct venipuncture, placed into potassium oxalate with sodium fluoride tubes, and maintained on wet ice until processed. Blood samples were centrifuged at a temperature of 4° C., at 3000×g, for 5 minutes. Blood samples were maintained chilled throughout processing. Plasma was collected in tubes and flash frozen. Samples were stored in a freezer set to maintain −60° C. to −80° C. until further analysis.

Bioanalysis of 2-PMPA Prodrugs in Plasma and Tissue: 2-PMPA concentrations in plasma and tissue samples were determined using two different methods (FIG. 2). Method 1 showed the total amount of the prodrug in the sample following oral dosing (a measure of the disappearance of the prodrug) and method 2 evaluated the specific release of 2-PMPA in plasma and tissues from the prodrug. In vitro screening showed metabolic instability of almost all the prodrugs tested.

Method 1 involved use of a strong derivatizing reagent, n-butanol with 3N HCl, which converted the prodrug and its metabolites including 2-PMPA into a 2-PMPA butyl ester to obtain the total exposures from the prodrug. Briefly, prior to extraction, frozen samples were thawed on ice. For plasma extraction, 50 μL of the calibration standards or samples were transferred into silanized microcentrifuge tubes. Sample preparation involved a single liquid extraction by addition of 300 μL of methanol as extraction solution with internal standard (i.e., 5 μM of 2-PMSA in methanol), followed by vortexing for 30 s and then centrifugation at 12000 g for 10 min. Supernatant was transferred (~250 μL) and evaporated to dryness at 40° C. under a gentle stream of nitrogen. The residue was reconstituted with 100 μL of derivatizing agent, n-butanol with 3N HCl, and samples were vortexed. The samples were heated at ~60° C. in a shaking water bath for 30 min. At the end of 30 min, the derivatized samples were allowed to cool at room temperature and dried again for removal of derivatizing reagent, under a gentle stream of nitrogen. The residue was reconstituted in 100 μL of 30% acetonitrile in water v/v. The samples were vortexed and centrifuged again. ~80 μL supernatant was transferred to a 250 μL polypropylene vial sealed with a Teflon cap and a volume of 10 μL was injected onto the ultra-performance liquid chromatography (UPLC) instrument for quantitative analysis. Chromatographic analysis was performed using an Accela™ ultra high-performance system consisting of an analytical pump, and an autosampler coupled with TSQ Vantage mass spectrometer (Thermo Fisher Scientific Inc., Waltham MA). Separation of the analyte from potentially interfering material was achieved at ambient temperature using Agilent Eclipse Plus column (100×2.1 mm i.d.) packed with a 1.8 μm C18 stationary phase. The mobile phase used was composed of 0.1% formic acid in acetonitrile and 0.1% formic acid in $H_2O$ with gradient elution, starting with 20% (organic) linearly increasing to 65% up to 2.5 min, maintaining at 65% (2.5-3.5 min) and reequilibrating to 30% by 5 min. The total run time for each analyte was 5.0 min. The $[M+H]^+$ ion transitions of derivatized 2-PMPA at m/z 325.522>121.296, 195.345 and that of the internal standard at m/z 339.537>191.354, 149.308, were monitored.

Method 2 was a gentle method to evaluate specific release of 2-PMPA in plasma and tissues from prodrug. Briefly, 2-PMPA was extracted from plasma by protein precipitation with 5×methanol containing 2-(phosphonomethyl) succinic acid (2-PMSA; 1 μM) as an internal standard. For brain tissue extraction, the samples were weighed in a 1.7 mL silanized tubes to which 4 times the volume of methanol (dilution 1:5) was added. The tissues were stored in −20° C. for 1 h and then homogenized. The calibration curve for the tissues was developed using naïve mouse brains from untreated animals as a matrix. For sciatic nerve, the nerves were weighed and homogenized in 50 μL methanol and the calibration curve was developed using naïve sciatic nerves from untreated animals as a matrix. The samples were vortexed and centrifuged. For tissue extraction, either 50 μL (brain) or 25 μL (sciatic nerve) of the calibration standards or samples were transferred into silanized microcentrifuge tubes. Sample preparation involved a single liquid extraction by addition of 150 μL of methanol as extraction solution with internal standard (i.e., 5 μM of 2-PMSA in methanol). Supernatant was dried under a gentle stream of nitrogen at 45° C. and the residue reconstituted with 75 μL of acetonitrile and vortexed. 25 μL of derivatizing agent N-tert-Butyldimethysilyl-N-methyltrifluoro-acetamide (MTB-STFA) was added to microcentrifuge tubes, vortexed, and heated at ~60° C. for 40 min. At the end of 40 min, the derivatized samples ~75 μL were transferred to a 250 μL polypropylene vials and were analyzed via LC/MS/MS. Chromatographic analysis was performed using an Accela™ ultra high-performance system consisting of an analytical pump, and an autosampler coupled with TSQ Vantage mass spectrometer (Thermo Fisher Scientific Inc., Waltham MA). Separation of the analyte from potentially interfering material was achieved at ambient temperature using Waters X-terra®, RP18, 3.5 μm, and (2.1×50 mm). The mobile phase used was composed of 0.1% formic acid in acetonitrile and 0.1% formic acid in $H_2O$ with gradient elution, starting with 90% (organic) linearly increasing to 99% up to 2.5 min, maintaining at 99% (2.5-4.0 min) and reequilibrating to 90% by 5 min. The total run time for each analyte was 5.0 min. Chromatographic analysis will be performed on Accela UPLC. The $[M+H]^+$ ion transitions of derivatized 2-PMPA at m/z 683.0>551.4 and that of the internal standard at m/z 669.0>537.2 were monitored with the total run time of 5 min.

$$\frac{\text{Avg. Response} * @ 60 \min}{\text{Avg. Response} @ 0 \min} \times 100$$

Where, Response=[(Area of analyte)/(Area of internal standard)]

*Average response is average of two samples at each time point.

Example 2

Compound Preparation

General Procedures: The $^1H$ NMR spectra were measured at 400.13. $^1H$ NMR spectra are standardized to the internal signal of TMS (δ 0.0, $CDCl_3$). The chemical shifts are given in δ-scale, the coupling constants J are given in Hz. The IR spectra were measured in CHCl3 on FT-IR spectrometer Bruker Equinox 55. Low and high resolution CI mass spectra were measured using an orthogonal acceleration time-of-flight (OA-TOF) mass spectrometer (GCT premier, Waters) at an ionising voltage of 70 eV, the m/z values are given with their relative intensities (%). The spectra were recorded in positive mode and the source temperature was 150° C. Methane was present as a reagent gas in the CI source. For exact measurement the spectra were internally calibrated using Heptacosa or 2,4,6-tris(trifluoromethyl)-1,3,5-triazine (Metri). The ESI mass spectra were recorded with a ZQ micromass mass spectrometer (Waters) equipped with an ESCi multi-mode ion source and controlled by MassLynx software. THF was freshly distilled from sodium/benzophenone under nitrogen. The flash chromatography was performed on Silica gel 60 (0.040-0.063 mm, Fluka).

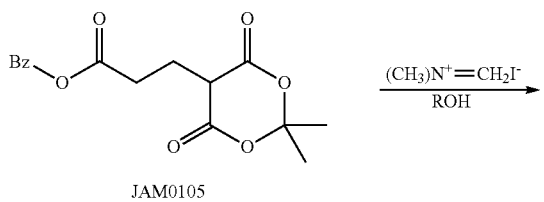 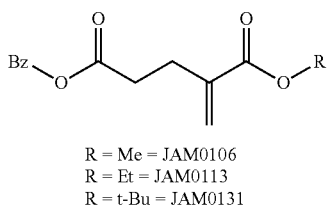

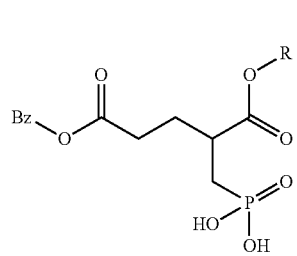

R = Me = TT-140113

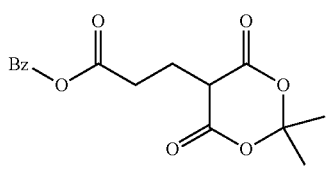

R = Me = JAM0109
R = Et = JAM0114
R = t-Bu = JAM0141

JAM0105

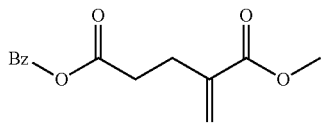

This compound was prepared from known literature. $^1$H NMR and $^{13}$C NMR spectra were in agreement with the published data.

JAM0106

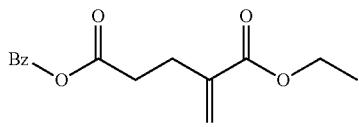

The same method of preparation as for previous compound JAM0131. Compound JAM0105 (6.62 g, 21.62 mmol), N,N-Dimethylmethyleneiminium iodide (10 g, 54.05 mmol, 2.5 equiv.) Absolute methanol (265 mL). Reaction mixture was stirred at 65° C. h. The organic solvent was evaporated in vacuo. The residue was filtered through pad of silica gel (hexane-ethyl acetate 5:1) to afford the desired product (5.02 g, 94%) as an oil. 1H NMR and 13C NMR spectra were in agreement with the published data.

JAM0113

The same method of preparation as for previous compound JAM0106. Compound JAM0105 (6.62 g, 21.62 mmol), N,N-Dimethylmethyleneiminium iodide (10 g, 54.05 mmol, 2.5 equiv.) Absolute ethanol (265 mL). Reaction mixture was stirred at 78° C. overnight. The organic solvent was evaporated in vacuo. The residue was filtered through pad of silica gel (hexane-ethyl acetate 10:1 to 5:1) to afford the desired product (5.25 g, 93%) as an oil. 1H NMR and 13C NMR spectra were in agreement with the published data.

JAM0131

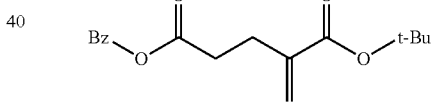

A dry Schlenk flask was charged with the previous compound JAM0105 (6.62 g, 21.62 mmol), N,N-Dimethylmethyleneiminium iodide (10 g, 54.05 mmol, 2.5 equiv.) and then it was flushed with argon. Absolute t-BuOH (265 mL) was added to the flask and the mixture was stirred at 65° C. for 48 h. The organic solvent was evaporated in vacuo. The residue was filtered through pad of silica gel (hexane-ethyl acetate 5:1) to afford the desired product (5 g, 80%) as an oil.

ESI MS: 313 (M+Na$^+$).

HR ESI MS: calcd for $C_{17}H_{22}O_4Na$ 313.14103; found 313.14106.

JAM0109

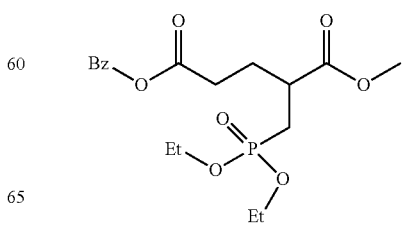

The same method of preparation as for previous compound JAM0149. Diethyl phosphite (2.6 mL, 20.14 mmol), A solution of trimethylaluminium (2 M in hexanes, 10 mL, 20.14 mmol, 1.0 equiv.) JAM0106 (5 g, 20.14 mmol, 1.0 equiv.) dichloromethane (70 mL). Filtration through pad of silica gel (hexane-ethyl acetate 1:1 to 3:1) Product (7.3 g, 94%) as an oil.

ESI MS: 323 (M+Na$^+$). HR ESI MS: calcd for $C_{17}H_{35}NO_2SNa$ 340.22807; found 340.22805.

JAM0114

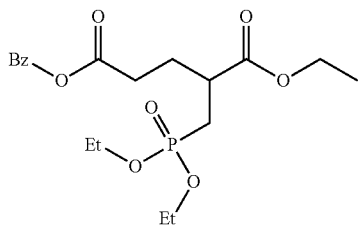

The same method of preparation as for previous compound JAM0149. Diethyl phosphite (2.58 mL, 20 mmol), A solution of trimethylaluminium (2 M in hexanes, 10 mL, 20 mmol, 1.0 equiv.) JAM0113 (5.25 g, 20 mmol, 1.0 equiv.) dichloromethane (70 mL). Filtration through pad of silica gel (hexane-ethyl acetate 1:1 to 3:1) Product (7.5 g, 94%) as an oil.

ESI MS: 323 (M+Na$^+$).

HR ESI MS: calcd for $C_{17}H_{35}NO_2SNa$ 340.22807; found 340.22805.

JAM0149

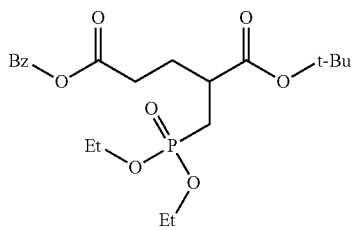

Diethyl phosphite (8.5 mL, 66.1 mmol, 1 equiv.) was dissolved in absolute dichloromethane (57 mL) under argon and cooled to 0° C. A solution of trimethyl aluminium (2 M in hexanes, 33 mL, 66.1 mmol, 1 equiv.) was added dropwise and the solution was stirred at 0° C. for 30 min. Solution of the compound JAM0131 (19.2 g, 66.1 mmol, 1 equiv) in dichloromethane (171 mL) was added and the cooling bath was removed. The reaction mixture was then stirred at room temperature overnight. The reaction was quenched with 2 N hydrochloric acid (40 mL). Then it was extracted with diethyl ether (3×40 mL), the combined organic layers were washed with water (40 mL), brine (40 mL), and dried over anhydrous MgSO4. The evaporation of the solvents afforded an oil, which was filtered through pad of silica gel (hexane-ethyl acetate 3:1 to 1:1) to afford the desired product (28.3 g, 94%) as an oil.

ESI MS: 323 (M+Na$^+$).

HR ESI MS: calcd for $C_{17}H_{35}NO_2SNa$ 340.22807; found 340.22805.

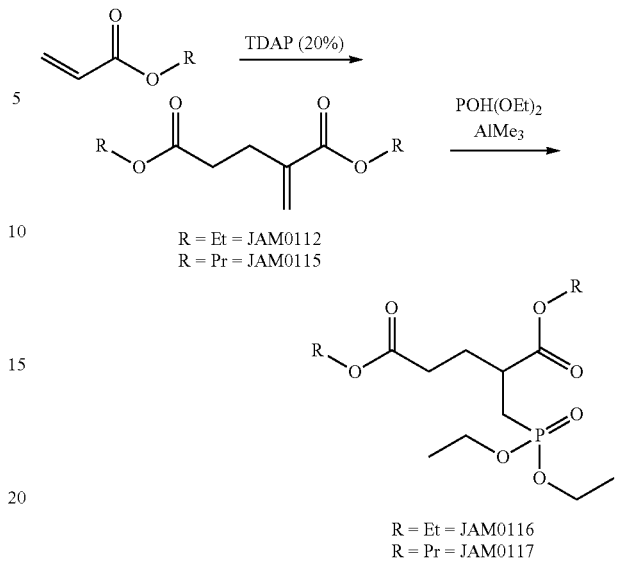

JAM0112

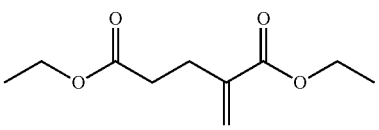

A Schlank flask was charged with Ethyl acrylate (15 mL, 0.14 mol) under argon, then TDAP (5 mL, 28 mmol, 20 mol %) was slowly added and the reactin mixture was stirred at 60° C. for 2 h. Product was destillated of on Kugelrohr apparatus (100° C. at 0.1 mbar). 1H NMR and 13C NMR spectra were in agreement with the published data.

JAM0115

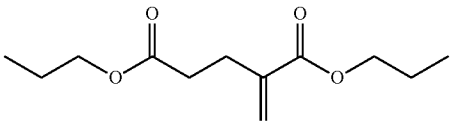 [SMILES: C=C(CCC(=O)OCCC)C(=O)OCCC]

A Schlank flask was charged with ethyl acrylate (15 mL, 0.12 mol) under argon, then TDAP (4.4 mL, 24 mmol, 20 mol %) was slowly added and the reactin mixture was stirred at 60° C. for 2 h. Product was destillated of on Kugelrohr apparatus (125° C. at 0.1 mbar).

JAM0116

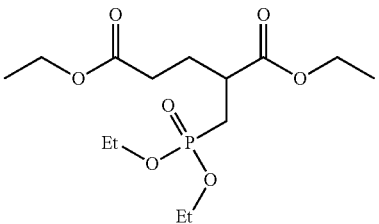 [SMILES: CCOC(=O)CCC(CP(=O)(OCC)OCC)C(=O)OCC]

The same method of preparation as for previous compound JAM0149. Diethyl phosphite (4.5 mL, 35 mmol), A solution of trimethylaluminium (2 M in hexanes, 17.5 mL, 35 mmol, 1.0 equiv.) JAM0112 (7.0 g, 35 mmol, 1.0 equiv.) dichloromethane (120 mL). Filtration through pad of silica gel (hexane-ethyl acetate 1:1 to 3:1) Product JAM0116 (11 g, 94%) as an oil.

1H NMR and 13C NMR spectra were in agreement with the published data.

JAM0117

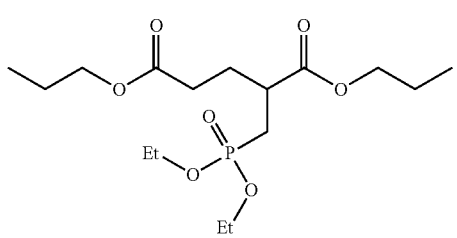 [SMILES: CCCOC(=O)CCC(CP(=O)(OCC)OCC)C(=O)OCCC]

The same method of preparation as for previous compound JAM0149. Diethyl phosphite (2.7 mL, 21 mmol), A solution of trimethylaluminium (2 M in hexanes, 10.5 mL, 21 mmol, 1.0 equiv.) JAM0115 (4.8 g, 21 mmol, 1.0 equiv.) dichloromethane (70 mL). Filtration through pad of silica gel (hexane-ethyl acetate 1:1 to 3:1) Product JAM0117 (7.2 g, 94%) as an oil. $^1$H NMR (400 MHz, CDCl$_3$): 0.92 (3H, t, J=7.4), 0.94 (3H, t, J=7.4), 1.28-1.32 (6H, m), 1.59-1.70 (4H, m), 1.79-1.89 (1H, m), 1.92-2.05 (2H, m), 2.19-2.40 (3H, m), 2.74-2.84 (1H, m), 4.00-4.12 (8H, m).

$^{31}$P NMR (162 MHz, CDCl$_3$): 28.55

ESI MS: 389 (M+Na$^+$).

HR ESI MS: calcd for C$_{16}$H$_{31}$O$_2$NaP 389.16996; found 389.16869.

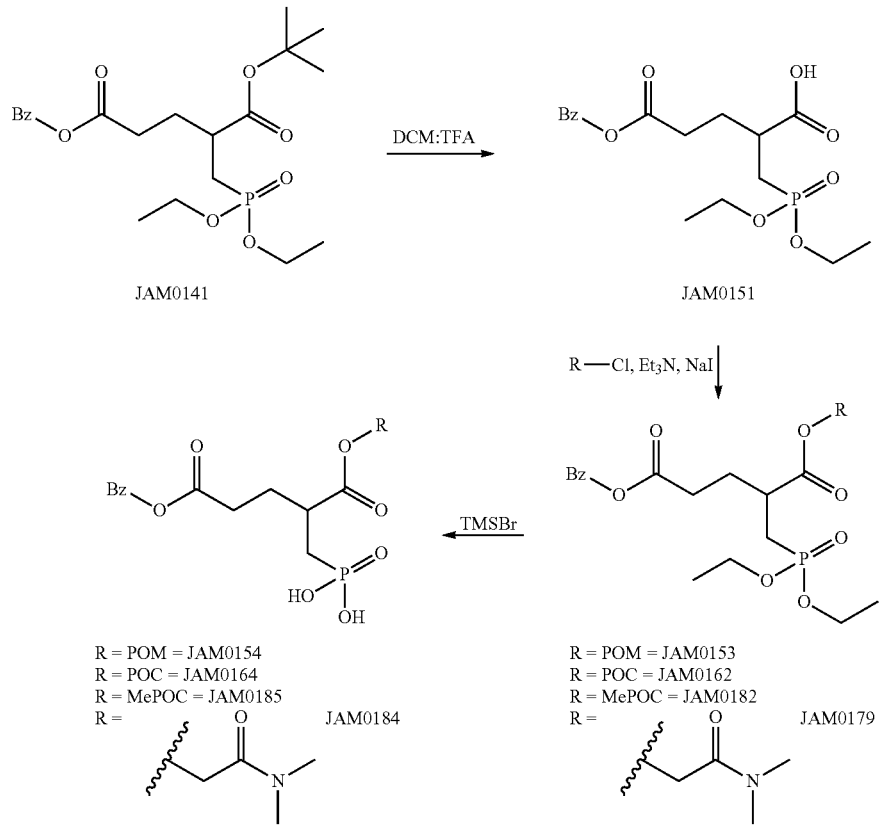

JAM0151

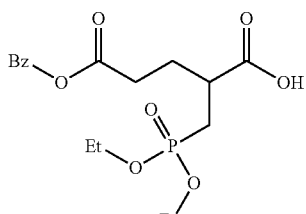

Phosphonate JAM0149 (25.4 g, 60 mmol), was dissolved in dichloromethane (100 mL) and trifluoroacetic acid (100 mL) was slowly added. The reaction mixture was stirred at room temperature overnight. Then the solvents were removed in vacuo. The residue was filtered through a short pad of silica gel (chloroform-methanol 10:1) to furnish the desired product (19.7 g, 88%) as an oil.

ESI MS: 395 (M+Na$^+$).

HR ESI MS: calcd for C$_{17}$H$_{35}$O$_7$NaP 395.12301; found 395.12337.

JAM0153

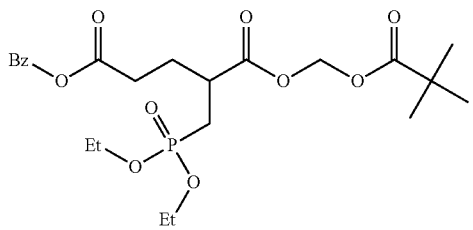

Dry flask was charged with phosphonate JAM0151 (1.95 g, 5.24 mmol), NaI (1.57 g, 7.86 mmol, 2 equiv.), triethylamine (1.1 mL, 7.86 mmol, 1.5 equiv.). Dry DMF was added and reaction mixture was stirred at room temperature for 15 min. and then Chloromethyl pivalate (1.5 mL, 10.47 mmol, 2 equiv.) was slowly added. Reaction mixture was stirred at room temperature overnight. The solvent was removed under reduced pressure and the residue was chromatographed on silica gel (ethyl acetate-hexane 40:1) to afford the desired product (1.38 g, 54%) as an oil.

ESI MS: 323 (M+Na$^+$).

HR ESI MS: calcd for $C_{17}H_{35}NO_2SNa$ 340.22807; found 340.22805.

JAM0162

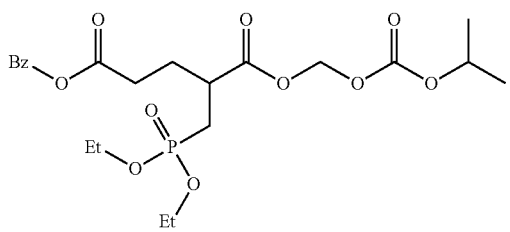

The same method of preparation as for previous compound JAM0153. Phosphonate JAM0151 (2.15 g, 5.77 mmol), NaI (1.73 g, 11.55 mmol, 2 equiv.), triethylamine (1.21 mL, 8.66 mmol, 1.5 equiv.), Chloromethyl isopropyl carbonate (1.55 mL, 11.55 mmol, 2 equiv.), DMF (30 mL).

Chromatography on silica gel (hexane-ethyl acetate 2:1). Product (1.97 g, 70%) as an oil.

ESI MS: 323 (M+Na$^+$).

HR ESI MS: calcd for $C_{17}H_{35}NO_2SNa$ 340.22807; found 340.22805.

JAM0182

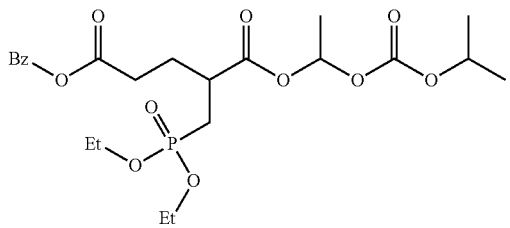

The same method of preparation as for previous compound JAM0153. Phosphonate JAM0151 (2 g, 5.37 mmol), NaI (1.61 g, 10.74 mmol, 2 equiv.), triethylamine (1.5 mL, 10.74 mmol, 2 equiv.), 1-Chloroethyl isopropyl carbonate (1.64 mL, 10.74 mmol, 2 equiv.), DMF (30 mL). Chromatography on silica gel (hexane-ethyl acetate 1:1). Product (1.1 g, 21%) as an oil.

ESI MS: 323 (M+Na$^+$).

HR ESI MS: calcd for $C_{17}H_{35}NO_2SNa$ 340.22807; found 340.22805.

JAM0179

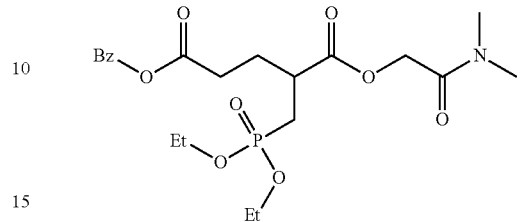

The same method of preparation as for previous compound JAM0153. Phosphonate JAM0151 (1.0 g, 2.68 mmol), NaI (805 mg, 5.37 mmol, 2 equiv.), triethylamine (750 µL, 5.37 mmol, 2 equiv.), 2-Chloro-N,N-dimethylacetamide (552 µL, 5.37 mmol, 2 equiv.), DMF (14 mL). Chromatography on silica gel (chloroform-methanol 20:1). Product (1 g, 85%) as an oil.

ESI MS: 323 (M+Na$^+$).

HR ESI MS: calcd for $C_{17}H_{35}NO_2SNa$ 340.22807; found 340.22805.

JAM0154

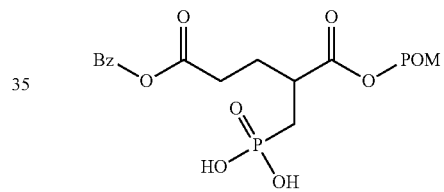

The compound JAM0153 (3.3 g, 6.78 mmol) was dissolved in absolute dichloromethane (40 mL) under argon and cooled to 0° C. A bromotrimethylsilane (3.6 mL, 27.13 mmol, 4 equiv.) was added dropwise and the solution was stirred at 0° C. overnight. The volatiles were removed in vacuo and the residue was diluted with mixture of methanol and toluene (3×30 mL, 1:1) and evaporated to obtain desired product (2.77 mg, 95%) as an oil and directly used in next reaction without characterization.

JAM0164

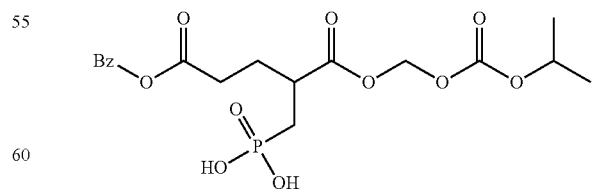

The same method of preparation as for previous compound JAM0154. Phosphonate JAM0162 (1.6 g, 3.28 mmol), TMSBr (1.54 mL, 11.68 mmol, 4 equiv.), DCM (20 mL). Product (1.39 g, 98%) obtained as an oil.

JAM0185

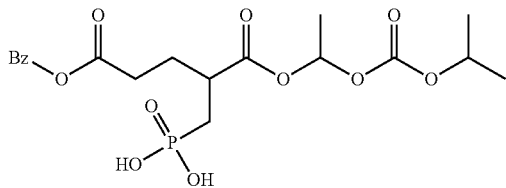

The same method of preparation as for previous compound JAM0154. Phosphonate JAM0182 (770 mg, 1.53 mmol), TMSBr (809 μL, 6.13 mmol, 4 equiv.), DCM (10 mL). Product (669 mg, 98%) obtained as an oil.

JAM0184

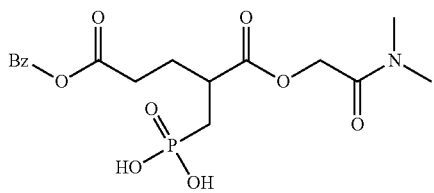

The same method of preparation as for previous compound JAM0154. Phosphonate JAM0179 (1.05 g, 2.30 mmol), TMSBr (1.21 mL, 9.18 mmol, 4 equiv.), DCM (13 mL). Product (904 mg, 98%) obtained as an oil.

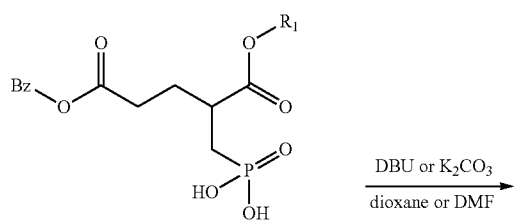

R₁ = POM = JAM0154
R₁ = POC = JAM0164
R₁ = MePOC = JAM0185
R₁ = 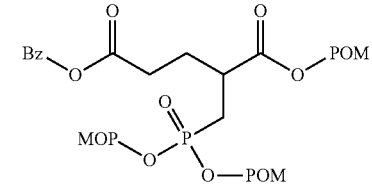 JAM0184

—continued

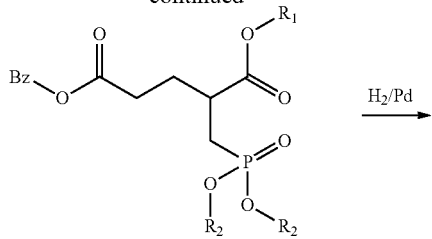

R₁ = R₂ = POM = JAM0167
R₁ = R₂ = POC = JAM0166
R₁ = R₂ = MePOC = JAM0189
R₂ = POC, R₁ = 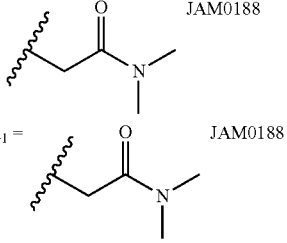 JAM0188

R₂ = MePOC, R₁ = 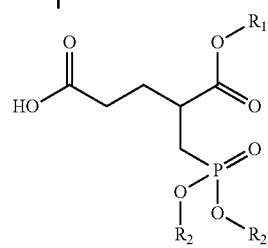 JAM0188

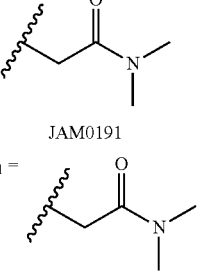

R₁ = R₂ = POM = JAM0168
R₁ = R₂ = POC = JAM0186
R₁ = R₂ = MePOC = JAM0195
R₂ = POC, R₁ =

JAM0191

R₂ = MePOC, R₁ =

JAM0196

JAM0167

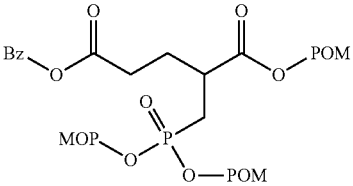

Dry Schlank flask was charged with previous compound JAM0154 (600 mg, 1.39 mmol) and dissolved in dry dioxane (7 mL). DBU (0.42 mL, 2.80 mmol, 2 equiv), Chloromethyl pivalate (0.8 mL, 5.58 mmol, 4 equiv.) was added and the reaction mixture was stirred at 100° C. for 6 h. The volatiles were removed in vacuo and the residue was chromatographed on silica gel (toluene-aceton 10:1 to afford impure desired product (48 mg, 5.2%) as an oil. The product was further purified using preparative scale HPLC (gradient 10:50, $R_t$=12.5 min.).

ESI MS: 323 (M+Na$^+$).

HR ESI MS: calcd for $C_{17}H_{35}NO_2SNa$ 340.22807; found 340.22805.

JAM0166

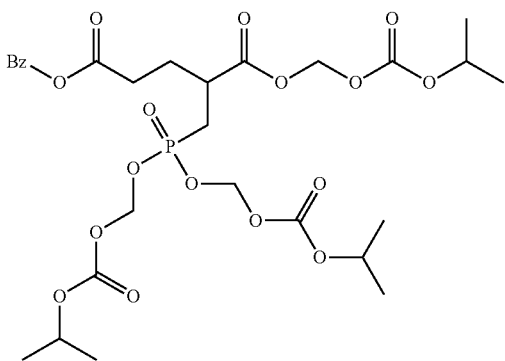

The same method of preparation as for previous compound JAM0167. Phosphonate JAM0164 (1.14 g, 2.64 mmol), DBU (0.79 mL, 5.28 mmol, 2 equiv), Chloromethyl isopropyl carbonate (3.5 mL, 26.40 mmol, 10 equiv.), dioxane (14 mL). Chromatography on silica gel (toluene-aceton 5:1). Product (mg, <10%) as an oil. The product was further purified using preparative scale HPLC (gradient 10:50, $R_t$=12.5 min.).

ESI MS: 323 (M+Na$^+$).

HR ESI MS: calcd for $C_{17}H_{35}NO_2SNa$ 340.22807; found 340.22805.

JAM0189

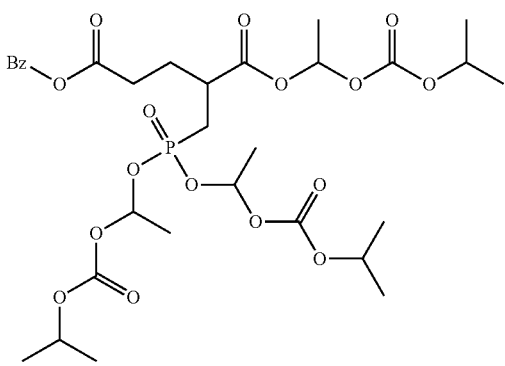

Dry Schlank flask was charged with previous compound JAM0185 (574 mg, 1.29 mmol), K$_2$CO$_3$ (550 mg, 3.98 mmol, 3.1 equiv.) and dissolved in dry DMF (12 mL). 1-Chloroethyl isopropyl carbonate (2 mL, 12.86 mmol, 10 equiv.) was added and the reaction mixture was stirred at 60° C. for 6 h. The volatiles were removed in vacuo and the residue was chromatographed on silica gel (toluene-aceton 7:1) to afford impure desired product (88 mg, 10%) as an oil. The product was further purified using preparative scale HPLC (gradient 10:50, $R_t$=12.5 min.).

ESI MS: 323 (M+Na$^+$).

HR ESI MS: calcd for $C_{17}H_{35}NO_2SNa$ 340.22807; found 340.22805.

JAM0188

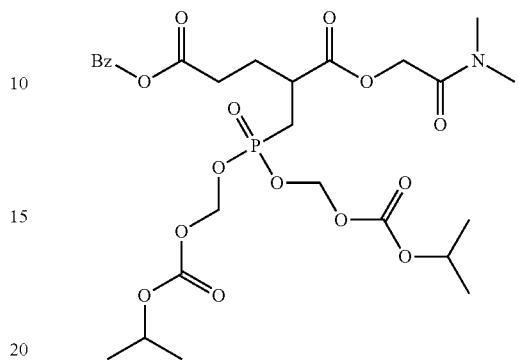

The same method of preparation as for previous compound JAM0167. Phosphonate JAM0184 (555 mg, 1.38 mmol), DBU (433 µL, 2.9 mmol, 2.1 equiv), Chloromethyl isopropyl carbonate (1.85 mL, 13.82 mmol, 10 equiv.), dioxane (7 mL). Chromatography on silica gel (chloroform-methanol 40:1). Product (96 mg, 11%) as an oil. The product was further purified using preparative scale HPLC (gradient 10:50, $R_t$=12.5 min.).

ESI MS: 656 (M+Na$^+$).

HR ESI MS: calcd for $C_{27}H_{40}O_{14}NNaP$ 656.20786; found 656.20772.

JAM0187

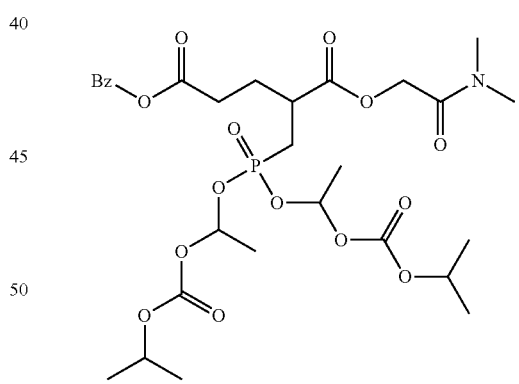

The same method of preparation as for previous compound JAM0189. Phosphonate JAM0184 (200 mg, 0.498 mmol), K$_2$CO$_3$ (344 mg, 2.49 mmol, 5 equiv.), 1-Chloroethyl isopropyl carbonate (304 µL, 1.99 mmol, 2 equiv.), DMF (6 mL). Chromatography on silica gel (chloroform-methanol 10:1). Product (92 mg, 28%) as an oil. The product was further purified using preparative scale HPLC (gradient 10:50, $R_t$=12.5 min.).

ESI MS: 323 (M+Na$^+$).

HR ESI MS: calcd for $C_{17}H_{35}NO_2SNa$ 340.22807; found 340.22805

JAM0168

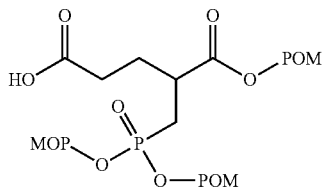

The previous compound JAM0167 (48 mg, 72.9 mmol) was dissolved in dry THF (3 mL). 10% Palladium on carbon (5 mg) was added and reaction mixture was bubbled with hydrogen for 10 min. Reaction mixture was stirred at room temperature overnight under hydrogen atmosphere. Palladium was filtered through cotton and the volatiles were removed in vacuo to afford desired product (40 mg, 98%) as an oil.

ESI MS: 323 (M+Na$^+$).

HR ESI MS: calcd for $C_{17}H_{35}NO_2SNa$ 340.22807; found 340.22805.

JAM0186

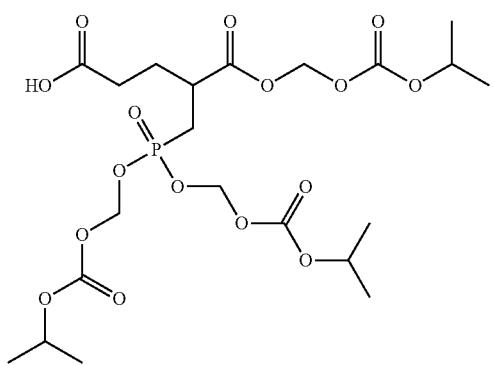 [SMILES: CC(C)OC(=O)OCOC(=O)C(CCC(=O)O)CP(=O)(OCOC(=O)OC(C)C)OCOC(=O)OC(C)C]

The same method of preparation as for previous compound JAM0168 (FIG. 1). Phosphonate (1.18 g, 1.77 mmol), 10% palladium on carbon (100 mg), THF (70 mL). Product (996 mg, 98%) as an oil.

ESI MS: 323 (M+Na$^+$).

HR ESI MS: calcd for $C_{17}H_{35}NO_2SNa$ 340.22807; found 340.22805.

JAM0195

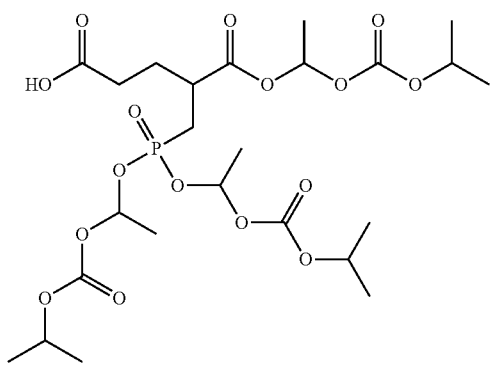 [SMILES: CC(C)OC(=O)OC(C)OC(=O)C(CCC(=O)O)CP(=O)(OC(C)OC(=O)OC(C)C)OC(C)OC(=O)OC(C)C]

The same method of preparation as for previous compound JAM0168. Phosphonate JAM0189 (1.0 g, 1.42 mmol), 10% palladium on carbon (100 mg), THF (45 mL). Product (587 mg, 98%) as an oil.

ESI MS: 323 (M+Na$^+$).

HR ESI MS: calcd for $C_{17}H_{35}NO_2SNa$ 340.22807; found 340.22805.

JAM0191

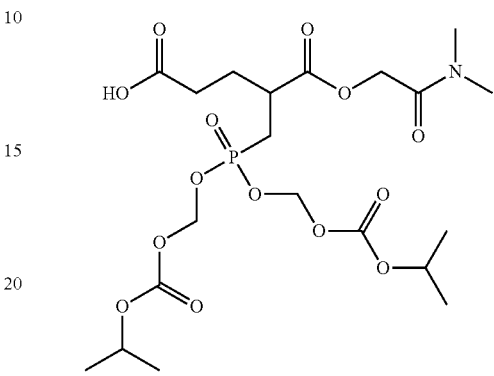

The same method of preparation as for previous compound JAM0168. Phosphonate JAM0188 (100 mg, 0.158 mmol), 10% palladium on carbon (10 mg), THF (5 mL). Product (84 mg, 98%) as an oil.

ESI MS: 566 (M+Na$^+$).

HR ESI MS: calcd for $C_{20}H_{34}O_{14}NNaP$ 566.16091; found 566.16087.

JAM0196

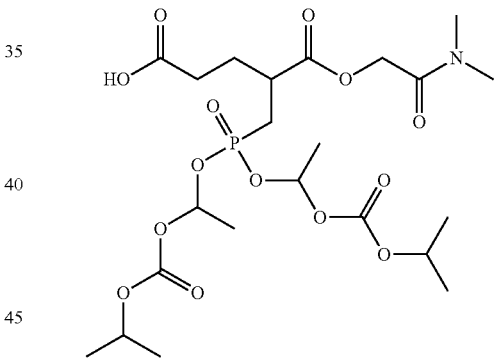

The same method of preparation as for previous compound JAM0168. Phosphonate JAM0187 (100 mg, 0.151 mmol), 10% palladium on carbon (10 mg), THF (5 mL). Product (84 mg, 98%) as an oil.

ESI MS: 594 (M+Na$^+$).

HR ESI MS: calcd for $C_{22}H_{38}O_{14}NaP$ 594.19221; found 594.19215

JAM0214

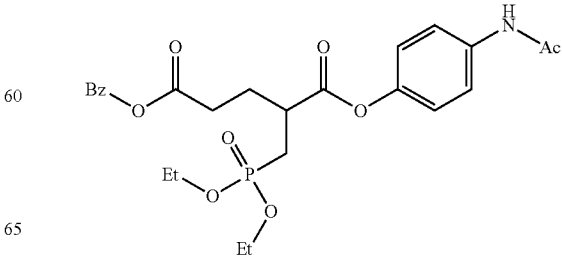

A flask was charged with phosphonate JAM0151 (2.0 g, 5.37 mmol), DCC (1.22 g, 5.91 mmol, 1.1 equiv.), DMAP (65.6 mg, 0.54 mmol, 10 mol %). Dry dichloromethane was added and the reaction mixture was stirred at room temperature for 15 min. Then 4-Acetamidophenol (974 mg, 6.44 mmol, 1.2 equiv.) was added in one portion. Reaction mixture was stirred at room temperature overnight. N,N-Dicyclohexylurea was filtered off and the organic solvent was evaporated in vacuo. The residue was chromatographed on silica gel (chloroform-methanol 20:1) to afford the desired product (1.55 g, 57%) as an oil.

ESI MS: 528 (M+Na$^+$).

HR ESI MS: calcd for $C_{25}H_{32}O_8NNaP$ 528.17577; found 528.17598.

JAM0216

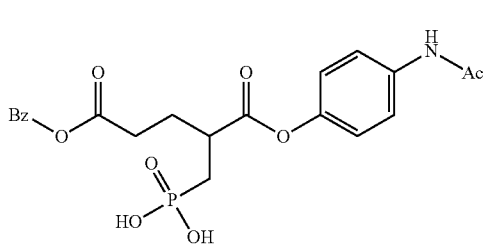

The same method of preparation as for previous compound JAM0154. Phosphonate JAM0214 (1.24 g, 2.48 mmol), TMSBr (1.31 mL, 9.92 mmol, 4 equiv.), DCM (16 mL). Product (1.1 g, 98%) obtained as an oil.

JAM0218

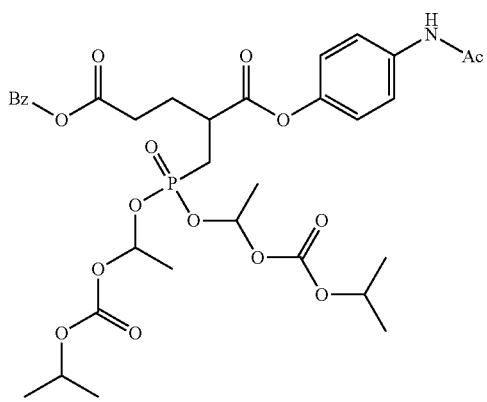

The same method of preparation as for previous compound JAM0189. Phosphonate JAM0216 (200 mg, 0.498 mmol), K$_2$CO$_3$ (344 mg, 2.49 mmol, 5 equiv.), 1-Chloroethyl isopropyl carbonate (304 µL, 1.99 mmol, 2 equiv.), DMF (6 mL). Chromatography on silica gel (chloroform-methanol 10:1). Product (90 mg, 25%) as an oil. The product was further purified using preparative scale HPLC (gradient 10:50, R$_t$=12.5 min.).

ESI MS: 323 (M+Na$^+$).

HR ESI MS: calcd for $C_{17}H_{35}NO_2SNa$ 340.22807; found 340.22805

JAM0219

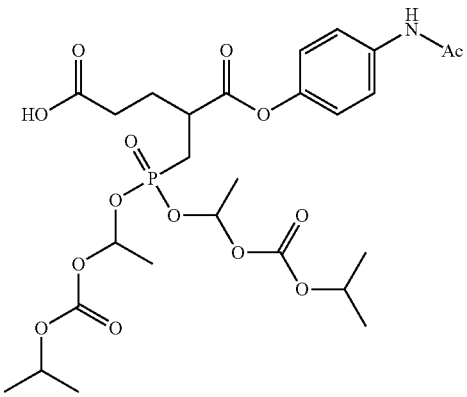 [SMILES: CC(=O)Nc1ccc(OC(=O)C(CCC(=O)O)CP(=O)(OC(C)OC(=O)OC(C)C)OC(C)OC(=O)OC(C)C)cc1]

The same method of preparation as for previous compound JAM0168. Phosphonate JAM0218 (100 mg, 0.158 mmol), 10% palladium on carbon (10 mg), THF (5 mL). Product JAM0218 (92 mg, 98%) as an oil.

ESI MS: 323 (M+Na$^+$).

HR ESI MS: calcd for $C_{17}H_{35}NO_2SNa$ 340.22807; found 340.22805

$^1$H NMR (400 MHz, CDCl$_3$): 0.93 (3H, t, J=7.2), 0.96 (3H, t, J=7.2), 1.63 (2H, q, J=7.2), 1.7 (2H, q, J=7.2), 2.50-2.54 (2H, m), 2.62-2.66 (2H, m), 4.02 (2H, t, J=6.7), 4.11 (2H, t, J=6.6), 5.58 (1H, d, J=1.2), 6.19 (1H, s).

$^{13}$C NMR (126 MHz, CDCl$_3$): 10.35, 10.43, 21.99, 22.00, 27.41, 33.17, 66.01, 66.30, 125.43, 139.25, 166.66, 172.71.

CI MS: 229 (M+H$^+$).

HR CI MS: calcd for $C_{12}H_{21}O_4$ 229.1440; found 229.1445.

5-benzyl 1-(((isopropoxycarbonyl)oxy)methyl) 2-((diphenoxyphosphoryl) methyl)pentanedioate JAM0338

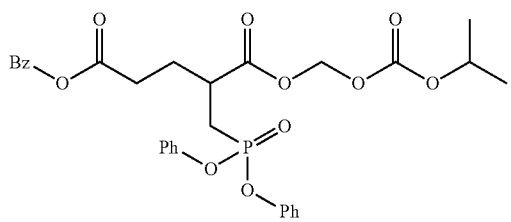

The compound JAM0162 (400 mg, 0.819 mmol) was dissolved in absolute dichloromethane (5 mL) under argon and cooled to 0° C. A bromotrimethylsilane (0.30 mL, 3.28 mmol, 4 equiv.) was added dropwise and the solution was stirred at 0° C. overnight. The volatiles were removed in vacuo and the residue was diluted with mixture of acetonitrile and water (5 mL, 4:1) and evaporated. The residue was dissolved in absolute dichloromethane and catalytic amount of DMF (8 μL) was added. To the reaction mixture was added oxalyl chloride (0.480 mL, 5.73 mmol, 7 equiv.) and the reaction mixture was stirred at room temperature for 2 h. The volatiles were removed in vacuo and the residue was dissolved under argon in absolute dichloromethane (5 mL) and cooled to −20° C. To this mixture was added mixture of phenol (162 mg, 1.72 mmol, 2.1 equiv.), diisopropylethylamine (0.5 mL) and pyridine (0.1 mL) in dichloromethane (3 mL). The reaction mixture was warmed slowly to room temperature and then stirred for 12 h. The volatiles were removed in vacuo and the residue was chromatographed on silica gel (hexane-ethyl acetate 2:1 to afford desired product (308 mg, 64%) as an oil.

$^1$H NMR (400 MHz, CDCl$_3$): 1.23 (3H, d, J=2.1), 1.25 (3H, d, J=2.1), 2.09-2.18 (2H, m), 2.18-2.28 (1H, m), 2.39-2.52 (2H, m), 2.56-2.67 (1H, m), 3.07-3.18 (1H, m), 4.85 (1H, hept, J=6.3), 5.11 (2H, s), 5.70 (1H, d, J=5.7), 5.77 (1H, d, J=5.7), 7.11-7.19 (6H, m), 7.27-7.38 (9H, m).

$^{13}$C NMR (101 MHz, CDCl$_3$): 21.67 (2C), 27.94 (d, J$_{C,P}$=143.9), 28.19 (d, J$_{C,P}$=12.4), 31.24, 39.18 (d, J$_{C,P}$=3.9), 66.63, 73.29, 82.28, 120.58 (2C, d, J$_{C,P}$=2.3), 120.62 (2C, d, J$_{C,P}$=2.3), 125.42 (d, J$_{C,P}$=1.1), 125.44 (d, J$_{C,P}$=1.1), 128.39, 128.41, 128.68, 129.33 (2C), 129.94 (2C), 135.82, 150.11 (d, J$_{C,P}$=3.4), 150.20 (d, J$_{C,P}$=3.6), 153.34, 172.13, 172.29 (d, J$_{C,P}$=9.3).

$^{31}$P NMR (101 MHz, CDCl$_3$): 23.82

ESI MS: 607 ([M+Na]$^+$).

HR ESI MS: calcd for C$_{30}$H$_{33}$O$_{10}$NaP 607.17035; found 607.17038.

4-((diphenoxyphosphoryl)methyl)-5-(((isopropoxycarbonyl)oxy)methoxy)-5-oxopentanoic acid JAM0338H

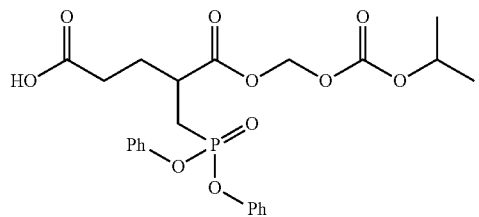

The same method of preparation as for previous compound JAM0278R. Phosphonate (300 mg, 0.51 mmol), 10% palladium on carbon (10 mg), THF (5 mL). Product (247 mg, 98%) as an oil. The product was further purified using preparative scale HPLC.

$^1$H NMR (400 MHz, CDCl$_3$): 1.26 (3H, d, J=3.9), 1.28 (3H, d, J=3.8), 2.04-2.20 (2H, m), 2.21-2.31 (1H, m), 2.37-2.51 (2H, m), 2.58-2.68 (1H, m), 3.09-3.19 (1H, m), 4.88 (1H, hept, J=6.3), 5.71 (1H, d, J=5.7), 5.80 (1H, d, J=5.7), 7.12-7.19 (6H, m), 7.28-7.33 (4H, m).

$^{13}$C NMR (101 MHz, CDCl$_3$): 21.68 (2C), 27.86 (d, J$_{C,P}$=144.1), 27.95 (d, J$_{C,P}$=12.3), 30.86, 39.02 (d, J$_{C,P}$=3.8), 73.38, 82.31, 120.58 (2C, d, J$_{C,P}$=1.9), 120.62 (2C, d, J$_{C,P}$=1.9), 125.54 (2C), 129.97 (4C), 150.03 (d, J$_{C,P}$=3.4), 150.12 (d, J$_{C,P}$=3.6), 153.38, 172.25 (d, J$_{C,P}$=9.5), 176.87.

$^{31}$P NMR (101 MHz, CDCl$_3$): 24.00

ESI MS: 517 ([M+Na]$^+$).

HR ESI MS: calcd for C$_{23}$H$_{28}$O$_{10}$P 495.14146; found 495.14111.

5-benzyl 1-(((isopropoxycarbonyl)oxy)methyl) 2-((bis(((S)-1-ethoxy-1-oxopropan-2-yl)amino)phosphoryl)methyl)pentanedioate JAM0341

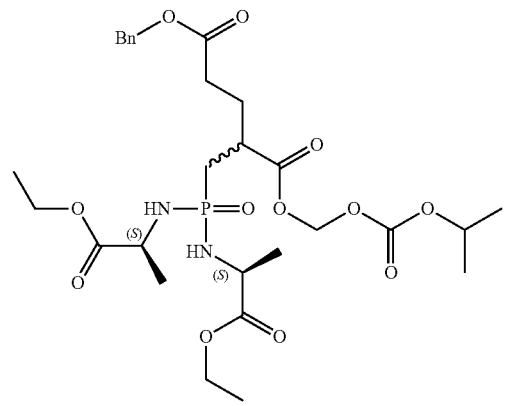

The compound JAM0162 (400 mg, 0.819 mmol) was dissolved in absolute dichloromethane (5 mL) under argon and cooled to 0° C. A bromotrimethylsilane (0.30 mL, 3.28 mmol, 4 equiv.) was added dropwise and the solution was stirred at 0° C. overnight. The volatiles were removed in vacuo and the residue was diluted with mixture of acetonitrile and water (5 mL, 4:1) and evaporated. The residue was dissolved in absolute dichloromethane and catalytic amount of DMF (8 μL) was added. To the reaction mixture was added oxalyl chloride (0.480 mL, 5.73 mmol, 7 equiv.) and the reaction mixture was stirred at room temperature for 2 h. The volatiles were removed in vacuo and the residue was dissolved under argon in absolute dichloromethane (5 mL) and cooled to −20° C. To this mixture was added mixture of L-alanine ethyl ester hydrochloride (264 mg, 1.72 mmol, 2.1 equiv.), diisopropylethylamine (1.0 mL) and pyridine (0.1 mL) in dichloromethane (3 mL). The reaction mixture was warmed slowly to room temperature and then stirred for 12 h. The volatiles were removed in vacuo and the residue was chromatographed on silica gel (chloroform-acetone 5:1 to afford desired product (238 mg, 46%) as an oil.

$^1$H NMR (400 MHz, CDCl$_3$): 1.15-1.20 (12H, m), 1.27-1.32 (6H, m), 1.67-1.80 (1H, m), 1.88-2.02 (1H, m), 2.08-2.21 (1H, m), 2.31-2.36 (2H, m), 2.83-2.98 (1H, m), 3.07-3.24 (2H, m), 3.85-3.98 (2H, m), 4.00-4.12 (4H, m), 4.80 (1H, hept, J=6.3), 5.02 (2H, s), 5.66 (1H, dd, J=43.8, 5.6), 5.70 (1H, dd, J=67.6, 5.7), 7.21-7.29 (5H, m).

$^{31}$P NMR (101 MHz, CDCl$_3$): 28.32 and 28.38 (mixture of diastereoizomers)

4-((bis(((S)-1-ethoxy-1-oxopropan-2-yl)amino)phosphoryl)methyl)-5-(((isopropoxycarbonyl)oxy)methoxy)-5-oxopentanoic acid JAM0341H

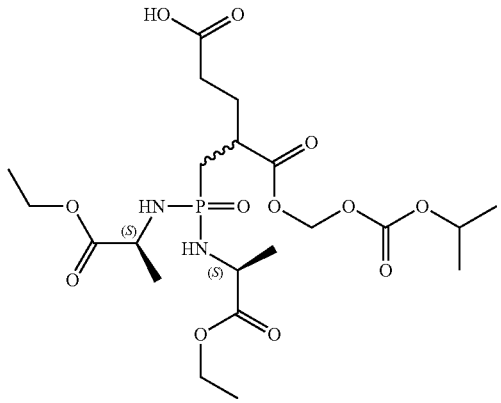

The same method of preparation as for previous compound JAM0278R. Phosphonate (100 mg, 0.16 mmol), 10% palladium on carbon (5 mg), THF (4 mL). Product (84 mg, 98%) as an oil. The product was further purified using preparative scale HPLC.

$^1$H NMR (400 MHz, CDCl$_3$): 1.23-1.30 (12H, m), 1.34-1.38 (6H, m), 1.86-2.02 (3H, m), 2.16-2.27 (1H, m), 2.28-2.41 (2H, m), 2.93-3.04 (1H, m), 3.41-3.60 (2H, m), 3.89-4.02 (2H, m), 4.09-4.21 (4H, m), 4.89 (1H, hept, J=6.2), 5.74 (1H, dd, J=41.2, 5.7), 5.76 (1H, dd, J=53.7, 5.7).

$^{31}$P NMR (101 MHz, CDCl$_3$): 31.00 (both diastereoizomers)

ESI MS: 563 ([M+Na]$^+$).

HR ESI MS: calcd for C$_{21}$H$_{37}$O$_{12}$N$_2$NaP 563.19763; found 563.19765.

Allyl-3-(2,2-dimethyl-4,6-dioxo-1,3-dioxan-5-yl)propanoate LTP089

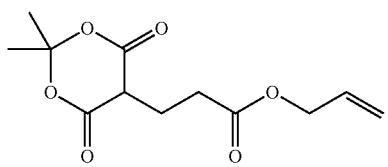 [SMILES: C=CCOC(=O)CCC1C(=O)OC(C)(C)OC1=O]

Meldrum's acid (5.0 g, 34.69 mmol, 1 eq.), a freshly grinded K$_2$CO$_3$ (4.8 g, 34.69 mmol, 1 eq.) and BnEt$_3$NCl (7.9 g, 34.69 mmol, 1 eq.) were suspended in dry AcN (50 mL). The reaction mixture was stirred for 1 hour at room temperature under inert atmosphere. Allyl acrylate (5.8 g, 6.2 mL, 52.04 mmol, 1.5 eq.) was added and the mixture was heated to 65° C. for 22 hours. AcN was evaporated. The residue was dissolved in EtOAc (200 mL), extracted with 10% KHSO$_4$ (3×150 mL), dried over MgSO$_4$ and the solvent was removed by vacuo. The crude product was suspended in hexane (50 mL) and sonicated. Desired product (7.3 g, 82%) was obtained after filtration as a colorless solid compound.

$^1$H NMR (400 MHz, CDCl$_3$): 1.76 (3H, s), 1.81 (3H, s), 2.39 (2H, dt, J=7.2, 5.6), 2.67 (2H, t, J=7.2), 3.91 (1H, t, J=5.6), 4.57 (2H, dt, J=5.8, 1.4), 5.23 (1H, dq, J=10.4, 1.3), 5.30 (1H, dq, J=17.2, 1.5), 5.90 (1H, ddt, J=17.2, 10.4, 5.8).

$^{13}$C NMR (101 MHz, CDCl$_3$): 21.30, 26.54, 28.66, 30.33, 44.84, 65.43, 105.23, 118.60, 132.05, 165.23 (2C), 172.61.

t-Butyl-3-(2,2-dimethyl-4,6-dioxo-1,3-dioxan-5-yl)propanoate LTP096

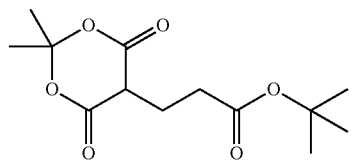 [SMILES: CC(C)(C)OC(=O)CCC1C(=O)OC(C)(C)OC1=O]

Meldrum's acid (10.0 g, 69.38 mmol, 1 eq.), a freshly grinded K$_2$CO$_3$ (9.6 g, 69.38 mmol, 1 eq.) and BnEt$_3$NCl (15.8 g, 69.38 mmol, 1 eq.) were suspended in dry AcN (100 mL). The reaction mixture was stirred for 1 hour at room temperature under inert atmosphere. t-Butyl acrylate (13.3 g, 15.1 mL, 104.07 mmol, 1.5 eq.) was added and the mixture was heated to 65° C. for 22 hours. AcN was evaporated. The residue was dissolved in EtOAc (300 mL), extracted with 10% KHSO$_4$ (3×200 mL), dried over MgSO$_4$ and the solvent was removed by vacuo. The crude product was suspended in hexane (100 mL) and sonicated. Desired product (11.4 g, 60%) was obtained after filtration as a colorless solid compound.

$^1$H NMR (400 MHz, CDCl$_3$): 1.42 (9H, s), 1.75 (3H, s), 1.80 (3H, s), 2.28-2.38 (2H, m), 2.52 (2H, td, J=7.3, 0.6), 3.91 (1H, t, J=5.6).

$^{13}$C NMR (101 MHz, CDCl$_3$): 21.47, 26.57, 28.20 (3C), 28.67, 31.52, 44.93, 80.98, 105.12, 165.35 (2C), 172.25.

Diallyl-2-methylenepentanedioate LTP013

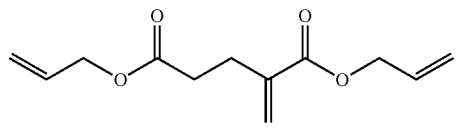 [SMILES: C=CCOC(=O)CCC(=C)C(=O)OCC=C]

A dry Schlenk flask was charged with allyl acrylate (1.00 g, 8.92 mmol, 2 eq.). Tributylphosphine (217 mg, 267 µL, 0.24 eq.) was added by drop wise. The reaction mixture was stirred for 2 h at rt under inert (exothermic at the beginning of reaction).

The crude product was purified by column chromatography (hexane-ethyl acetate 15:1) and the desired product was obtained as a colourless oil (785 mg) in 79% yield.

$^1$H NMR (400 MHz, CDCl$_3$): 2.54-2.59 (2H, m), 2.67 (2H, t, J=7.4), 4.57 (2H, dt, J=5.8, 1.4), 4.66 (2H, dt, J=5.8, 1.4), 5.15-5.38 (4H, m), 5.62 (1H, d, J=1.2), 5.84-6.01 (2H, m), 6.23 (1H, d, J=1.2).

$^{13}$C NMR (101 MHz, CDCl$_3$): 27.45, 33.19, 65.31, 65.54, 118.31, 118.43, 126.30, 132.21, 132.27, 138.93, 166.39, 172.45.

5-Allyl-1-t-butyl-2-methylenepentanedioate LTP091

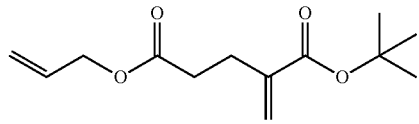 [SMILES: C=CCOC(=O)CCC(=C)C(=O)OC(C)(C)C]

A dry Schlenk flask was charged with the compound LTP089 (4.00 g, 15.61 mmol), N,N-Dimethylmethyleneiminium iodide (7.22 g, 39.02 mmol, 2.5 eq.) and then it was flushed with argon. Absolute t-BuOH (100 mL) was added to the flask and the mixture was stirred at 70-75° C. for 20 h. The organic solvent was evaporated in vacuo. The residue was dissolved in Et$_2$O (200 mL) and extracted with sat. NaHCO$_3$ (150 mL), 10% KHSO$_4$ (150 mL), 10% Na$_2$S$_2$O$_5$ (150 mL), sat. NaCl (150 mL), dried over MgSO$_4$. Solvent was evaporated. The crude product was purified by column chromatography (hexane-ethyl acetate 8:1) to afford the desired product (3.04 g, 81%) as a colourless oil.

$^1$H NMR (400 MHz, CDCl$_3$): 1.48 (9H, s), 2.49-2.55 (2H, m), 2.56-2.64 (2H, m), 4.56 (2H, dt, J=5.7, 1.4), 5.21 (1H, dt, J=10.4, 1.2), 5.29 (1H, dt, J=10.4, 1.2), 5.49 (1H, d, J=1.2), 5.83-5.95 (1H, m). 6.08 (1H, d, J=1.2).

$^{13}$C NMR (101 MHz, CDCl$_3$): 27.53, 28.17, 33.29, 65.22, 80.88, 118.30, 124.87, 132.30, 140.57, 165.99, 172.56.

1-Allyl-5-t-butyl-2-methylenepentanedioate LTP097

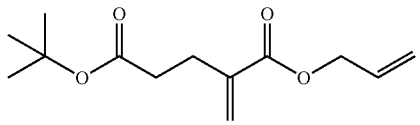 [SMILES: C=CCOC(=O)C(=C)CCC(=O)OC(C)(C)C]

A dry Schlenk flask was charged with the compound LTP096 (5.00 g, 18.36 mmol), N,N-Dimethylmethyleneiminium iodide (8.49 g, 45.91 mmol, 2.5 eq.) and then it was flushed with argon. Absolute allyl alcohol (50 mL) was added to the flask and the mixture was stirred at 70° C. for 20 h. The organic solvent was evaporated in vacuo. The residue was dissolved in Et$_2$O (200 mL) and extracted with sat. NaHCO$_3$ (150 mL), 10% KHSO$_4$ (150 mL), 10% Na$_2$S$_2$O$_5$ (150 mL), sat. NaCl (150 mL), dried over MgSO$_4$. Solvent was evaporated. The crude product was purified by column chromatography (hexane-ethyl acetate 10:1) to afford the desired product (2.37 g, 54%) as a colourless oil.

$^1$H NMR (400 MHz, CDCl$_3$): 1.43 (9H, s), 2.38-2.48 (2H, m), 2.56-2.66 (2H, m), 4.56 (2H, dt, J=5.6, 1.5), 5.24 (1H, dt, J=10.4, 1.3), 5.33 (1H, dt, J=17.2, 1.6), 5.60 (1H, d, J=1.3), 5.95 (1H, ddt, J=17.2, 10.4, 5.6). 6.21 (1H, d, J=1.3).

$^{13}$C NMR (101 MHz, CDCl$_3$): 27.57, 28.23, 34.35, 65.47, 80.57, 118.20, 125.87, 132.28, 139.23, 166.51, 172.13.

Diallyl-2-((diethoxyphosphoryl)methyl)pentanedioate LTP016

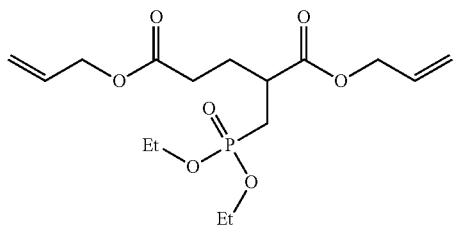 [SMILES: C=CCOC(=O)CCC(CP(=O)(OCC)OCC)C(=O)OCC=C]

Diethyl phosphite (439 mg, 410 µL, 3.18 mmol, 1 eq.) was dissolved in absolute dichloromethane (8 mL) under argon and cooled to 0° C. A solution of trimethyl aluminium (2 M in hexanes, 1.59 mL, 3.18 mmol, 1 equiv.) was added dropwise and the solution was stirred at 0° C. for 30 min. The solution of the compound LTP013 (712 mg, 3.18 mmol, 1 eq.) in dichloromethane (3 mL) was added during 10 min at 0° C., the mixture was stirred next 30 min at the same temperature and then the cooling bath was removed. The reaction mixture was stirred at room temperature overnight. After 16 h the reaction was quenched with 2 N hydrochloric acid (10 mL). The organic layer was separated and a water phase was extracted with DCM (2×20 mL). The combined organic layers were washed with water (20 mL), brine (20 mL) and dried over anhydrous MgSO$_4$. The crude product was an oil, which was filtered through pad of silica gel (EtOAc) to afford the desired product (1.04 g, 90%) as a colourless oil.

$^1$H NMR (400 MHz, CDCl$_3$): 1.24-1.28 (6H, m), 1.81 (1H, ddd, J=18.5, 15.4, 5.3), 1.90-2.02 (2H, m), 2.21 (1H, ddd, J=18.1, 15.5, 8.5), 2.27-2.39 (2H, m), 2.79 (1H, tdd, J=13.6, 8.3, 5.5), 4.03 (4H, tt, J=8.7, 5.2), 4.53 (4H, dd, J=12.1, 5.7), 5.18 (2H, ddd, J=10.4, 6.8, 1.4), 5.27 (2H, ddd, J=17.2, 12.6, 1.3), 5.79-5.93 (2H, m).

5-Allyl-1-t-butyl-2-((diethoxyphosphoryl)methyl)pentanedioate LTP093

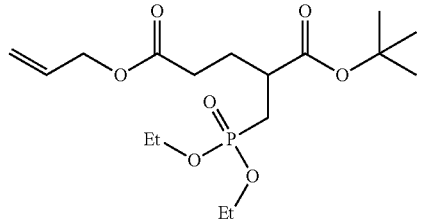 [SMILES: C=CCOC(=O)CCC(CP(=O)(OCC)OCC)C(=O)OC(C)(C)C]

Diethyl phosphite (1.72 g, 1.60 mL, 12.44 mmol, 1 eq.) was dissolved in absolute dichloromethane (30 mL) under argon and cooled to 0° C. A solution of trimethyl aluminium (2 M in hexanes, 6.22 mL, 12.44 mmol, 1 equiv.) was added dropwise and the solution was stirred at 0° C. for 30 min. The solution of the compound LTP091 (2.99 g, 12.44 mmol, 1 eq.) in dichloromethane (10 mL) was added during 15 min at 0° C., the mixture was stirred next 30 min at the same temperature and then the cooling bath was removed. The reaction mixture was stirred at room temperature overnight. After 20 h the reaction was quenched with 2 N hydrochloric acid (40 mL). The organic layer was separated and a water phase was extracted with DCM (2×50 mL). The combined organic layers were washed with water (20 mL), brine (20 mL) and dried over anhydrous MgSO$_4$. The crude product was an oil, which was filtered through pad of silica gel (EtOAc-hexane 2:1) to afford the desired product (4.13 g, 88%) as a colourless oil.

$^1$H NMR (400 MHz, CDCl$_3$): 1.28 (6H, td, J=7.1, 1.7), 1.42 (9H, s), 1.69-1.80 (1H, m), 1.84-2.00 (2H, m), 2.12-2.24 (1H, m), 2.26-2.45 (2H, m), 2.59-2.73 (1H, m), 4.06 (4H, dq, J=8.2, 7.1), 4.54 (2H, dt, J=5.7, 1.4), 5.19 (1H, dq, J=10.4, 1.3), 5.27 (1H, dq, J=17.2, 1.5), 5.82-5.93 (1H, m).

1-Allyl-5-t-butyl-2-((diethoxyphosphoryl)methyl) pentanedioate LTP100

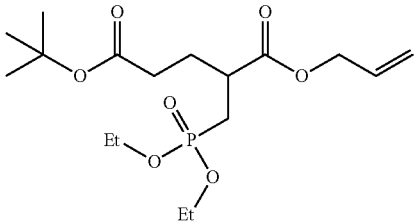 [SMILES: C=CCOC(=O)C(CCC(=O)OC(C)(C)C)CP(=O)(OCC)OCC]

Diethyl phosphite (1.36 g, 1.27 mL, 9.86 mmol, 1 eq.) was dissolved in absolute dichloromethane (26 mL) under argon and cooled to 0° C. A solution of trimethyl aluminium (2 M in hexanes, 4.93 mL, 9.86 mmol, 1 equiv.) was added dropwise and the solution was stirred at 0° C. for 30 min. The solution of the compound LTP097 (2.37 g, 9.86 mmol, 1 eq.) in dichloromethane (9 mL) was added during 15 min at 0° C., the mixture was stirred next 30 min at the same temperature and then the cooling bath was removed. The reaction mixture was stirred at room temperature overnight. After 16 h the reaction was quenched with 2 N hydrochloric acid (35 mL). The organic layer was separated and a water phase was extracted with DCM (2×45 mL). The combined organic layers were washed with water (20 mL), brine (20 mL) and dried over anhydrous MgSO$_4$. The crude product was an oil, which was filtered through pad of silica gel (EtOAc-hexane 2:1) to afford the desired product (3.20 g, 86%) as a colourless oil.

$^1$H NMR (400 MHz, CDCl$_3$): 1.29 (6H, tdd, J=7.1, 3.3, 0.4), 1.42 (9H, s), 1.78-1.88 (1H, m), 1.89-1.99 (2H, m), 2.16-2.33 (3H, m), 2.75-2.86 (1H, m), 4.01-4.12 (4H, m), 4.59 (2H, dq, J=5.8, 1.2), 5.23 (1H, dq, J=10.4, 1.3), 5.32 (1H, dq, J=17.2, 1.5), 5.91 (1H, ddt, J=17.2, 10.4, 5.8).

$^{13}$C NMR (101 MHz, CDCl$_3$): 16.47 (d, J$_{C,P}$=2.0), 16.53 (d, J$_{C,P}$=1.8), 37.91 (d, J$_{C,P}$=142.6), 28.18, 28.82 (d, J$_{C,P}$=13.0), 32.78, 39.37, 61.83 (d, J$_{C,P}$=6.5), 61.92 (d, J$_{C,P}$=6.3), 65.66, 80.66, 118.63, 171.87, 173.92 (d, J$_{C,P}$=7.9).

5-(Allyloxy)-2-((diethoxyphosphoryl)methyl)-5-oxopentanoic acid LTP111

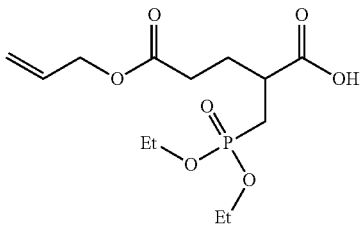 [SMILES: C=CCOC(=O)CCC(CP(=O)(OCC)OCC)C(=O)O]

Phosphonate LTP093 (1.50 g, 3.96 mmol), was dissolved in dichloromethane (15 mL) and the mixture was cooled to 0° C. Trifluoroacetic acid (15 mL) was added slowly during 15 minutes. The reaction mixture was stirred at room temperature overnight (18 h). Then the solvents were removed in vacuo. The residue was dissolved in PhCH$_3$ (2×15 mL) and evaporated. The crude product was purified on silica gel (chloroform-methanol 12:1) to furnish the desired product (1.22 g, 95%) as an oil.

$^1$H NMR (400 MHz, CDCl$_3$): 1.31 (6H, td, J=7.1, 2.1), 1.80-2.05 (3H, m), 2.25-2.49 (3H, m), 2.78-2.92 (1H, m), 4.05-4.17 (4H, m), 4.59 (2H, dq, J=5.9, 1.3), 5.25 (1H, dq, J=10.4, 1.2), 5.33 (1H, dq, J=17.2, 1.5), 5.90 (1H, ddt, J=17.2, 10.4, 5.9), 11.40 (1H, bs).

$^{13}$C NMR (101 MHz, CDCl$_3$): 16.31 (2C, d, J$_{C,P}$=6.2), 27.43 (d, J$_{C,P}$=131.9), 28.21, 31.19, 39.02 (d, J$_{C,P}$=3.7), 62.97 (d, J$_{C,P}$=5.4), 63.03 (d, J$_{C,P}$=5.1), 65.98, 119.07, 131.76, 173.48 (d, J$_{C,P}$=8.5), 177.84.

5-(Allyloxy)-4-((diethoxyphosphoryl)methyl)-5-oxopentanoic acid LTP104

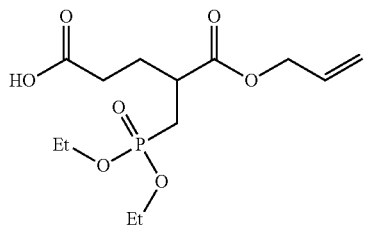 [SMILES: C=CCOC(=O)C(CCC(=O)O)CP(=O)(OCC)OCC]

Phosphonate LTP100 (3.19 g, 8.43 mmol), was dissolved in dichloromethane (30 mL) and the mixture was cooled to 0° C. Trifluoroacetic acid (30 mL) was added slowly during 20 minutes. The reaction mixture was stirred at room temperature overnight (16 h). Then the solvents were removed in vacuo. The residue was dissolved in PhCH$_3$ (2×15 mL) and evaporated. The crude product was purified on silica gel (chloroform-methanol 12:1) to furnish the desired product (2.60 g, 96%) as an oil.

$^1$H NMR (400 MHz, CDCl$_3$): 1.30 (6H, td, J=7.0, 2.1), 1.83-2.07 (3H, m), 2.23-2.36 (1H, m), 2.37-2.49 (2H, m), 2.75-2.87 (1H, m), 4.04-4.19 (4H, m), 4.56 (2H, dt, J=5.8, 1.4), 5.21 (1H, dq, J=10.4, 1.2), 5.29 (1H, dq, J=17.2, 1.5), 5.88 (1H, ddt, J=17.2, 10.4, 5.8), 12.11 (1H, bs).

$^{13}$C NMR (101 MHz, CDCl$_3$): 16.21 (d, J$_{C,P}$=2.6), 16.27 (d, J$_{C,P}$=2.6), 27.30 (d, J$_{C,P}$=144.2), 28.15 (d, J$_{C,P}$=12.6), 31.35, 38.99 (d, J$_{C,P}$=3.7), 62.99 (d, J$_{C,P}$=2.5), 63.06 (d, J$_{C,P}$=2.4), 65.48, 118.52, 132.03, 172.39, 178.38 (d, J$_{C,P}$=8.3).

(5-(Allyloxy)-2-((allyloxy)carbonyl)-5-oxopentyl) phosphonic acid LTP018

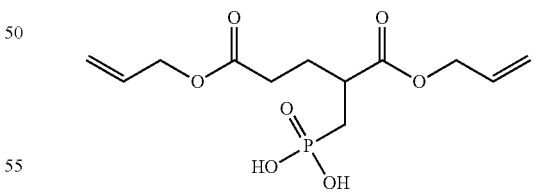

The compound LTP016 (4.02 g, 11.09 mmol) was dissolved in absolute dichloromethane (62 mL) under argon and cooled to 0° C. Bromotrimethylsilane (6.79 g, 5.86 mL, 44.38 mmol, 4 eq.) was added dropwise during 20 min and the solution was stirred at 0° C. overnight. The volatiles were removed in vacuo and the residue was diluted with mixture of acetonitrile and water (30 mL, 4:1) and evaporated. The crude product was obtained in quantitative yield (3.40 g) and it was used for the next step without purification.

¹H NMR (400 MHz, CDCl₃): 1.84-2.02 (3H, m), 2.21-2.36 (1H, m), 2.37-2.43 (2H, m), 2.79-2.92 (1H, m), 4.55-4.64 (4H, m), 5.20-5.27 (2H, m), 5.27-5.32 (1H, m), 5.32-5.37 (1H, m), 5.84-5.97 (2H, m), 9.89 (2H, bs).

5-(Allyloxy)-5-oxo-2-(phosphonomethyl)pentanoic acid LTP116

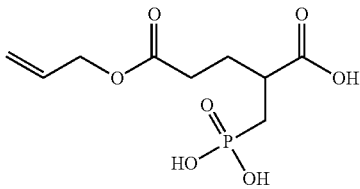 [SMILES: C=CCOC(=O)CCC(CP(=O)(O)O)C(=O)O]

The compound LTP111 (500 mg, 1.55 mmol) was dissolved in absolute dichloromethane (10 mL) under argon and cooled to 0° C. Bromotrimethylsilane (1.43 g, 1.23 mL, 9.31 mmol, 6 eq.) was added dropwise during 20 min and the solution was stirred at 0° C. overnight. The volatiles were removed in vacuo and the residue was diluted with mixture of acetonitrile and water (20 mL, 4:1) and evaporated. The crude product was obtained in quantitative yield (413 mg) and it was used for the next step without purification.

¹H NMR (400 MHz, d⁶-DMSO): 1.56-2.00 (3H, m), 2.24-2.42 (2H, m), 2.52-2.61 (2H, m), 4.53 (2H, dt, J=5.4, 1.6), 5.20 (1H, dq, J=10.3, 1.4), 5.29 (1H, dq, J=17.3, 1.7), 5.90 (1H, ddt, J=17.3, 10.3, 5.4), 7.53 (3H, bs).
¹³C NMR (101 MHz, d⁶-DMSO): 27.62 (d, $J_{C,P}$=9.6), 29.48 (d, $J_{C,P}$=137.5), 31.09, 31.26, 64.43, 117.74, 132.78, 172.02, 175.55 (d, $J_{C,P}$=10.6).

5-(Allyloxy)-5-oxo-4-(phosphonomethyl)pentanoic acid LTP115

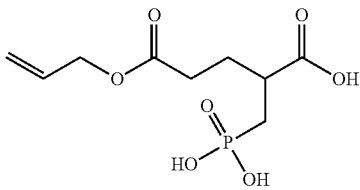 [SMILES: C=CCOC(=O)CCC(CP(=O)(O)O)C(=O)O]

The compound LTP104 (500 mg, 1.55 mmol) was dissolved in absolute dichloromethane (10 mL) under argon and cooled to 0° C. Bromotrimethylsilane (1.43 g, 1.23 mL, 9.31 mmol, 6 eq.) was added dropwise during 20 min and the solution was stirred at 0° C. overnight. The volatiles were removed in vacuo and the residue was diluted with mixture of acetonitrile and water (20 mL, 4:1) and evaporated. The crude product was obtained in quantitative yield (413 mg) and it was used for the next step without purification.

¹H NMR (400 MHz, d⁶-DMSO): 1.59-1.81 (2H, m), 1.82-1.99 (2H, m), 2.11-2.28 (2H, m), 2.61-2.72 (1H, m), 4.53 (2H, dt, J=5.6, 1.5), 5.20 (1H, dq, J=10.5, 1.4), 5.31 (1H, dq, J=17.3, 1.7), 5.91 (1H, ddt, J=17.3, 10.5, 5.6), 7.09 (3H, bs).
¹³C NMR (101 MHz, d⁶-DMSO): 28.10 (d, $J_{C,P}$=11.2), 29.72 (d, $J_{C,P}$=137.4), 31.12 (2C), 64.67, 117.85, 132.76, 173.72, 173.80 (d, $J_{C,P}$=9.1).

Diallyl-2-((bis((4-acetoxybenzyl)oxy)phosphoryl)methyl)pentanedioate LTP021

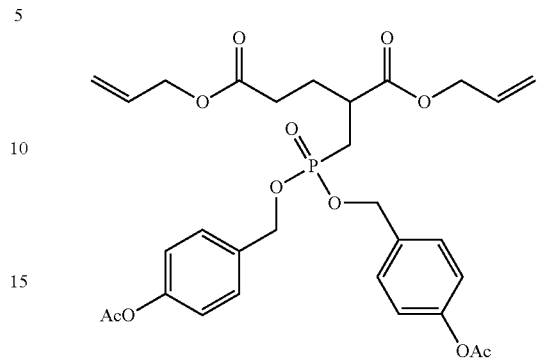

Compound LTP018 (104 mg, 0.340 mmol, 1 eq.) was dissolved in dry THF (1.5 mL). Triphenylphosphine (223 mg, 0.849 mmol, 2.5 eq.) and 4-acetoxybenzyl alcohol (141 mg, 0.849 mmol, 2.5 eq.) was added in one portion and finally DIAD (172 mg, 167 µL, 0.849 mmol, 2.5 eq.) was added by dropwise during 5 min (exothermic reaction). The reaction mixture was stirred for 1 h at rt. THF was evaporated by rotavap and the crude product was purified by column chromatography (DCM/EtOAc 2:1). The desired product (150 mg, 73%) was obtained as a viscous colourless oil.

¹H NMR (400 MHz, CDCl₃): 1.81-2.01 (2H, m), 2.29 (6H, s), 2.30-2.40 (4H, m), 2.75-2.90 (1H, m), 4.37-4.52 (2H, m), 4.55 (2H, d, J=5.4), 4.85-5.06 (4H, m), 5.16-5.42 (4H, m), 5.74-6.01 (2H, m), 7.07 (4H, dd, J=8.6, 2.3), 7.35 (4H, dd, J=7.3, 2.5).

1-(4-Acetoxybenzyl)-5-allyl-2-((bis((4-acetoxybenzyl)oxy)phosphoryl) methyl) pentanedioate LTP119

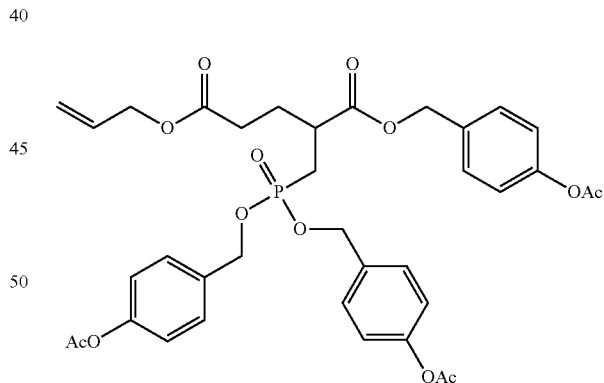

Compound LTP116 (300 mg, 1.13 mmol, 1 eq.) was dissolved in dry THF (9 mL). Triphenylphosphine (1.18 g, 4.51 mmol, 4 eq.) and 4-acetoxybenzyl alcohol (749 mg, 4.51 mmol, 4 eq.) was added in one portion and finally DIAD (912 mg, 888 µL, 4.51 mmol, 4 eq.) was added by dropwise during 5 min (exothermic reaction). The reaction mixture was stirred for 1 h at rt. THF was evaporated by rotavap and the crude product was purified by column chromatography (EtOAc/hexane 2:1 to EtOAc). The desired product (275 mg, 34%) was obtained as a viscous colourless oil.

¹H NMR (400 MHz, CDCl₃): 1.82-2.02 (3H, m), 2.25-2.39 (3H, m), 2.30 (3H, s), 2.31 (6H, s), 2.79-2.91 (1H, m), 4.55 (2H, dt, J=5.7, 1.4), 4.88-5.04 (6H, m), 5.22 (1H, dq, J=10.4, 1.3), 5.29 (1H, dq, J=17.2, 1.5), 5.89 (1H, ddt, J=17.2, 10.4, 5.7), 7.03-7.11 (6H, m), 7.29-7.37 (6H, m).

5-(4-Acetoxybenzyl)-1-allyl-2-((bis((4-acetoxybenzyl)oxy)phosphoryl) methyl) pentanedioate LTP122

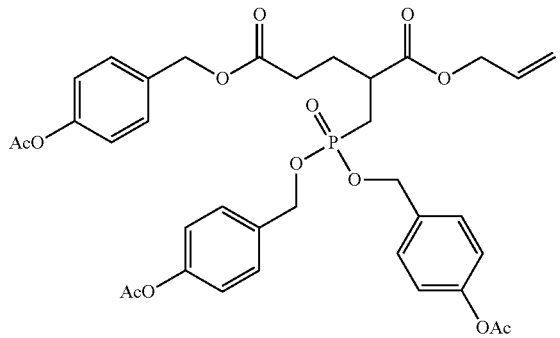 [SMILES: C=CCOC(=O)C(CCC(=O)OCc1ccc(OC(C)=O)cc1)CP(=O)(OCc1ccc(OC(C)=O)cc1)OCc1ccc(OC(C)=O)cc1]

Compound LTP122 (400 mg, 1.50 mmol, 1 eq.) was dissolved in dry THF (12 mL). Triphenylphosphine (1.58 g, 6.01 mmol, 4 eq.) and 4-acetoxybenzyl alcohol (999 mg, 6.01 mmol, 4 eq.) was added in one portion and finally DIAD (1.22 g, 1.18 mL, 6.01 mmol, 4 eq.) was added by dropwise during 5 min (exothermic reaction). The reaction mixture was stirred for 1 h at rt. THF was evaporated by rotavap and the crude product was purified by column chromatography (EtOAc). The desired product (1.0 g, 94%) was obtained as a viscous colourless oil.

$^1$H NMR (400 MHz, CDCl$_3$): 1.76-2.00 (3H, m), 2.22-2.38 (3H, m), 2.27 (3H, s), 2.28 (6H, s), 2.73-2.86 (1H, m), 4.43 (2H, dt, J=5.8, 1.6), 4.85-5.02 (6H, m), 5.17 (1H, dq, J=10.3, 1.2), 5.24 (1H, dq, J=17.2, 1.5), 5.89 (1H, ddt, J=17.2, 10.3, 5.8), 7.02-7.09 (6H, m), 7.28-7.38 (6H, m).

$^{13}$C NMR (101 MHz, CDCl$_3$): 21.05, 21.11 (2C), 21.68, 21.90, 21.96, 28.15 (d, $J_{C,P}$=142.2), 28.39 (d, $J_{C,P}$=13.5), 31.32, 39.11 (d, $J_{C,P}$=3.7), 64.53, 65.64, 65.71, 66.74 (d, $J_{C,P}$=2.5), 66.80 (d, $J_{C,P}$=2.1), 69.99, 118.63, 121.59, 121.73, 121.81 (d, $J_{C,P}$=2.5), 128.00, 129.24, 129.49, 131.79, 133.42, 133.63 (d, $J_{C,P}$=1.8), 133.69 (d, $J_{C,P}$=1.4), 138.73, 149.95, 150.53, 150.71 (d, $J_{C,P}$=1.7), 169.30, 169.40, 169.58, 172.14, 173.40 (d, $J_{C,P}$=7.8).

2-((Bis((4-acetoxybenzyl)oxy)phosphoryl)methyl) pentanedioic acid LTP023

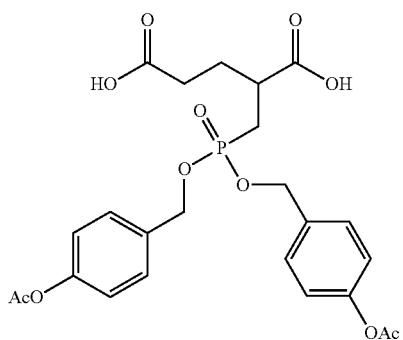 [SMILES: CC(=O)Oc1ccc(COP(=O)(CC(CCC(=O)O)C(=O)O)OCc2ccc(OC(C)=O)cc2)cc1]

The starting material LTP021 (144 mg, 0.239 mmol, 1 eq.) was dissolved in dry THF (2 mL). Pd(PPh$_3$)$_4$ (13.8 mg, 0.012 mmol, 5 mol %) was added in one portion and finally phenyl silane (103 mg, 117 µL, 0.956 mmol, 4 eq.) was added by dropwise during 2 min. The reaction mixture was stirred at rt under inert atmosphere for 1 h. THF was evaporated and crude product was filtered through pad of silica gel (EtOAc/MeOH 2:1) and finally purified by preparative HPLC. The desired product (50 mg, 40%) was obtained as an amorphous solid (after lyophilisation).

$^1$H NMR (400 MHz, CDCl$_3$): 1.70-2.04 (2H, m), 2.28 (6H, s), 2.31-2.49 (4H, m), 2.70-2.81 (1H, m), 4.85-5.04 (4H, m), 7.05 (4H, dd, J=8.4, 1.6), 7.32 (4H, dd, J=8.5, 1.6), 7.81 (2H, s).

5-(4-Acetoxybenzyl)-4-((bis((4-acetoxybenzyl)oxy) phosphoryl)methyl)-5-oxopentanoic acid LTP120

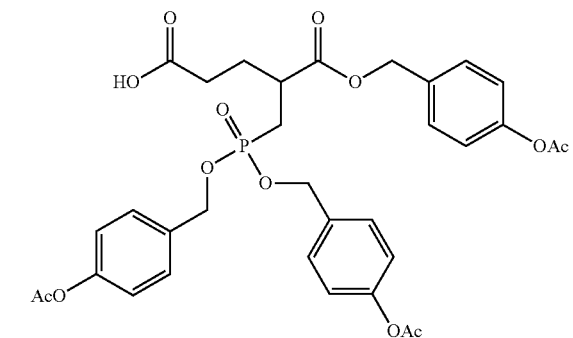 [SMILES: CC(=O)Oc1ccc(COC(=O)C(CCC(=O)O)CP(=O)(OCc2ccc(OC(C)=O)cc2)OCc2ccc(OC(C)=O)cc2)cc1]

The starting material LTP119 (139 mg, 0.196 mmol, 1 eq.) was dissolved in dry THF (2 mL). Pd(PPh$_3$)$_4$ (11.3 mg, 0.010 mmol, 5 mol %) was added in one portion and finally phenyl silane (42 mg, 48 µL, 0.391 mmol, 2 eq.) was added by dropwise during 2 min. The reaction mixture was stirred at rt under inert atmosphere for 1 h. THF was evaporated and crude product was filtered through pad of silica gel (CHCl$_3$/MeOH 20:1 to 10:1) and finally purified by preparative HPLC. The desired product (114 mg, 87%) was obtained as an oil.

$^1$H NMR (400 MHz, CDCl$_3$): 1.82-1.97 (2H, m), 2.29 (3H, s), 2.30 (6H, s), 2.16-2.37 (4H, m), 2.72-2.85 (1H, m), 4.86-5.03 (6H, m), 6.03 (1H, bs), 7.00-7.08 (6H, m), 7.28-7.35 (6H, m).

$^{13}$C NMR (101 MHz, CDCl$_3$): 21.25 (3C), 27.97 (d, $J_{C,P}$=142.8), 28.13 (d, $J_{C,P}$=13.1), 30.80, 38.98 (d, $J_{C,P}$=3.6), 66.35, 67.32 (d, $J_{C,P}$=3.7), 67.38 (d, $J_{C,P}$=3.6), 121.88 (2C), 122.05 (2C), 122.06 (2C), 129.55 (2C), 129.60 (2C), 129.78 (2C), 133.22, 133.51, 133.57, 150.73, 150.91, 150.93, 169.59, 169.67, 169.74, 173.51 (d, $J_{C,P}$=8.5), 175.36.

5-(4-Acetoxybenzyl)-2-((bis((4-acetoxybenzyl)oxy) phosphoryl)methyl)-5-oxopentanoic acid LTP123

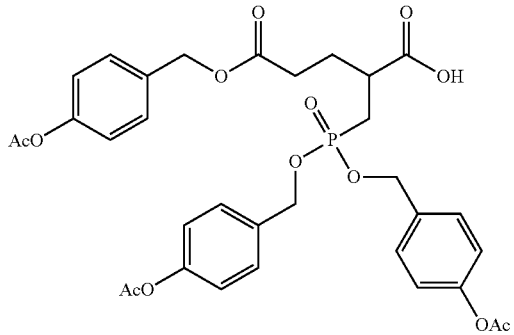 [SMILES: CC(=O)Oc1ccc(COC(=O)CCC(CP(=O)(OCc2ccc(OC(C)=O)cc2)OCc2ccc(OC(C)=O)cc2)C(=O)O)cc1]

The starting material LTP122 (500 mg, 0.703 mmol, 1 eq.) was dissolved in dry THF (4 mL). Pd(PPh$_3$)$_4$ (41 mg, 0.035 mmol, 5 mol %) was added in one portion and finally phenyl silane (152 mg, 173 µL, 1.41 mmol, 2 eq.) was added by dropwise during 2 min. The reaction mixture was stirred at rt under inert atmosphere for 1 h. THF was evaporated and crude product was filtered through pad of silica gel (CHCl$_3$/MeOH 15:1) and finally purified by preparative HPLC. The desired product (246 mg, 52%) was obtained as an oil.

$^1$H NMR (400 MHz, CDCl$_3$): 1.83-2.04 (2H, m), 2.27 (6H, s), 2.28 (3H, s), 2.30-2.47 (4H, m), 2.72-2.83 (1H, m), 4.88-5.03 (4H, m), 5.05 (2H, s), 7.05 (6H, dd, J=8.5, 2.0), 7.32 (6H, dd, J=8.1, 1.4), 9.24 (1H, bs).

$^{13}$C NMR (101 MHz, CDCl$_3$): 21.14 (2C), 21.15, 27.89 (d, $J_{C,P}$=143.0), 28.22 (d, $J_{C,P}$=13.8), 31.35, 38.79 (d, $J_{C,P}$=3.5), 65.79, 67.47, 67.54, 121.77 (2C), 121.94 (4C), 129.43 (2C), 129.44 (2C), 129.52 (2C), 133.32, 133.38, 133.49, 150.56, 150.85 (2C), 169.52, 169.53, 169.57, 172.40, 176.57 (d, $J_{C,P}$=7.5).

1-((5-methyl-2-oxo-1,3-dioxol-4-yl)methyl) 5-(2-(trimethylsilyl)ethyl) 2-((diethoxyphosphoryl)methyl)pentanedioate TT-160614

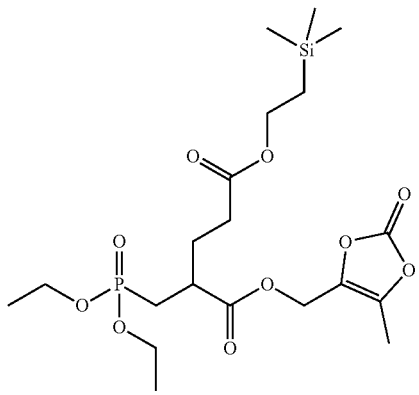 [SMILES: CCOP(=O)(CC(CCC(=O)OCC[Si](C)(C)C)C(=O)OCc1oc(=O)oc1C)OCC]

To a solution of 2-((diethoxyphosphoryl)methyl)-5-oxo-5-(2-(trimethylsilyl)ethoxy)pentanoic acid (1.49 g, 3.90 mmol), 4-(hydroxymethyl)-5-methyl-1,3-dioxol-2-one (663 mg, 5.1 mmol) and HOBt (690 mg, 5.1 mmol) in anhydrous DMF (10 ml) a solution of EDC.HCl (980 mg, 5.1 mmol) and DMAP (623 mg, 5.1 mmol) in DMF (10 ml) was added. The mixture was stirred at RT overnight. The solvent was evaporated and the residue was extracted with EtOAc—H2O mixture (1:1, 200 ml). Aqueous portion was extracted with EtOAc (50 ml) again. Organic extracts were dried with MgSO4 and evaporated. The residue was chromatographed on a silica gel column in EtOAc→1% MeOH/EtOAc. Yield 1.75 g of oil (91%).

$^1$H NMR (400 MHz, CDCl$_3$): 0.04 (s, 9H, Si—CH$_3$); 0.98 (m, 2H, Si—CH$_2$); 1.29-1.33 (m, 6H, CH$_3$(Et)), 1.88 (ddd, 1H, $J_{1b-P}$=18.7, $J_{gem}$=15.4, $J_{1b-2}$=5.0, H-1b), 1.95-2.03 (m, 2H, H-3), 2.19 (t, 3H, $J_{CH3-CH2}$=0.5, 4'—CH$_3$), 2.21 (ddd, $J_{1a-P}$=17.8, $J_{gem}$=15.4, $J_{1a-2}$=8.9, H-1a), 2.27-2.35 (m, 2H, H-4), 2.84 (m, 1H, H-2), 4.05-4.12 (m, 4H, CH$_2$ (Et)), 4.16 (m, 2H, OCH$_2$ (TMSE)), 4.84 (dq, 1H, $J_{gem}$=13.9, $J_{CH2-CH3}$=0.5, 3'-CH$_2$b), 4.89 (dq, 1H, $J_{gem}$=13.9, $J_{CH2-CH3}$=0.5, 3'-CH$_2$a).

$^{13}$C NMR (101 MHz, CDCl$_3$): −1.55 (Si—CH$_3$), 9.37 (4'-CH$_3$), 16.37 (d, $J_{CH3-P}$=6.0, CH$_3$(Et)), 17.26 (Si—CH$_2$), 27.69 (d, $J_{1-P}$=128.7, C-1), 28.31 (C-3), 31.41 (C-4), 39.15 (d, $J_{2-P}$=3.7, C-2), 54.17 (3'-CH$_2$), 61.81-61.92 (m, CH$_2$ (Et)), 62.90 (OCH$_2$ (TMSE)), 133.24 (C-3'), 140.20 (C-4'), 152.01 (C-1'), 171.40 (C-5), 173.48 (d, $J_{C-2-1-P}$=7.7, COO).

ESI MS: 517 ([M+Na]$^+$).

HR ESI MS: calcd for C$_{20}$H$_{35}$O$_{10}$NaPSi 517.16293; found 517.16306.

1-((5-methyl-2-oxo-1,3-dioxol-4-yl)methyl) 5-(2-(trimethylsilyl)ethyl) 2-((bis((5-methyl-2-oxo-1,3-dioxol-4-yl)methoxy)phosphoryl)methyl)pentanedioate TT-230614

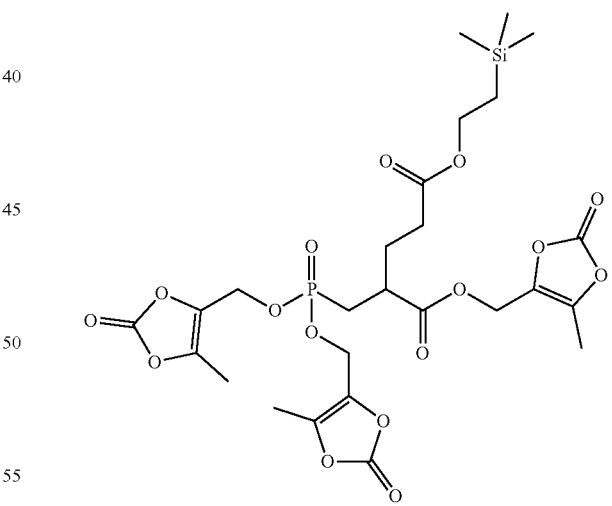

To a solution of 1-((5-methyl-2-oxo-1,3-dioxol-4-yl)methyl) 5-(2-(trimethylsilyl)ethyl) 2-((diethoxyphosphoryl)methyl)pentanedioate (1.70 g, 3.438 mmol) in anhydrous acetonitrile (40 ml) Me$_3$SiBr (3.6 ml, 27.5 mmol) was added at 0° C. The mixture was kept at 0° C. overnight, then evaporated and codistilled with MeCN, dissolved in dioxane (30 ml) and treated with water (240 □l, 13.3 mmol). The solution was stirred 30 min at room temperature then toluen (30 ml) was added and the solvents were evaporated. To a solution of resulting phosphonic acid, triphenylphosphine (5.4 g, 20.6 mmol) and 4-(hydroxymethyl)-5-methyl-1,3-dioxol-2-one (2.68 g, 20.6 mmol) in THF (80 ml) DIAD (4.0 ml, 20.6 mmol) was added dropwise. The mixture was stirred 6 h at room temperature. The solvent was removed in vacuo and the residue was chromatographed on a silica gel column in EtOAc→3% MeOH/EtOAc. Yield 1.01 g (44%).

$^1$H NMR (400 MHz, CDCl$_3$): 0.04 (s, 9H, Si—CH$_3$), 0.98 (m, 2H, Si—CH$_2$), 1.94-2.02 (m, 3H, H-3, H-1b), 2.20 (3×s, 9H, 4'-CH$_3$), 2.25-2.34 (m, 3H, H-1a, H-4), 2.83 (m, 1H, H-2), 4.16 (m, 2H, OCH$_2$ (TMSE)), 4.77-4.93 (m, 6H, 3'-CH$_2$).

$^{13}$C NMR (101 MHz, CDCl$_3$): −1.56 (Si—CH$_3$), 9.30, 9.33 (4'-CH$_3$), 17.24 (Si—CH$_2$), 28.15 (d, $J_{1-P}$=141.5, C-1), 28.26 (d, $J_{3-P}$=14.5, C-3), 31.16 (C-4), 38.76 (d, $J_{2-P}$=3.8, C-2), 54.37 (COO—CH$_2$-3'), 55.23, 55.35 (2×d, $J_{C-O-P}$=5.8, 6.0, P—O—CH$_2$), 63.02 (OCH$_2$ (TMSE)), 132.96 (C-3'), 133.29, 133.30 (2×d, $J_{3'-P}$=6.0, C-3'), 140.30, 140.31, 140.44 (C-4'), 151.71, 151.74, 152.07 (C-1'), 172.24 (C-5), 172.93 (d, $J_{C-2-1-P}$=6.6, COO).

ESI MS: 685 ([M+Na]$^+$).

HR ESI MS: calcd for C$_{26}$H$_{35}$O$_{16}$NaPSi 685.13242; found 685.13262.

4-((hydroxy((5-methyl-2-oxo-1,3-dioxol-4-yl)methoxy)phosphoryl)methyl)-5-((5-methyl-2-oxo-1,3-dioxol-4-yl)methoxy)-5-oxopentanoic acid TT-200714

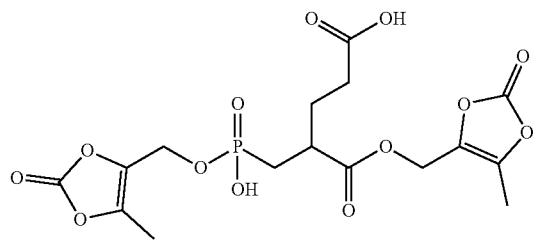 [SMILES: Cc1oc(=O)oc1COC(=O)C(CCC(=O)O)CP(=O)(O)OCc1oc(=O)oc1C]

A solution of 1-((5-methyl-2-oxo-1,3-dioxol-4-yl)methyl) 5-(2-(trimethylsilyl)ethyl) 2-((bis((5-methyl-2-oxo-1,3-dioxol-4-yl)methoxy)phosphoryl)methyl) pentanedioate (690 mg, 1.04 mmol) in anhydrous dichloromethane (10 ml) was treated with TFA (1 ml) at 0° C. The mixture was stirred 48 h at 0° C. then evaporated and the residue was chromatographed twice on a silica gel column in EtOAc→50% MeOH/EtOAc. Yield 110 mg (23%).

$^1$H NMR (400 MHz, CD3COCD$_3$): 1.80-2.12 (m, 4H, H-3, H-1), 2.21 (bs, 6H, 2×CH$_3$), 2.32, 2.40 (2×bs, 2H, H-4), 2.90 (bs, 1H, H-2), 4.74-5.09 (m, 4H, O—CH$_2$). $^{13}$C NMR (101 MHz, CD3COCD$_3$): 9.34, 9.43 (2×CH$_3$), 29.0 (C-1, C-3), 31.7 (C-4), 40.1 (C-2), 54.92, 55.22 (2×OCH$_2$), 134.69, 136.26 (C-3'), 139.88, 141.21 (C-4'), 152.97, 153.22 (C-1'), 172.15 (C-5), 175.50 (COO).

ESI MS: 449 ([M−H]$^-$).

HR ESI MS: calcd for C$_{16}$H$_{18}$O$_{13}$P 449.04905; found 449.04895.

Bis((5-methyl-2-oxo-1,3-dioxol-4-yl)methyl)2-((diethoxyphosphoryl)methyl) pentanedioate TT-301014

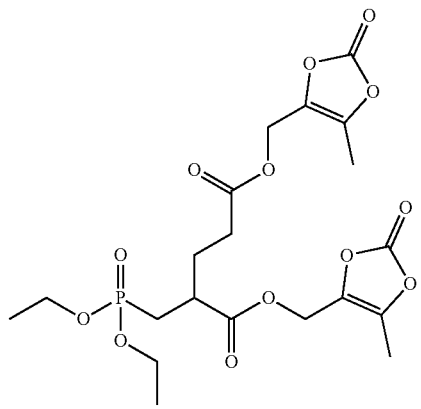 [SMILES: CCOP(=O)(CC(CCC(=O)OCc1oc(=O)oc1C)C(=O)OCc1oc(=O)oc1C)OCC]

Dibenzyl 2-((diethoxyphosphoryl)methyl)pentanedioate (2.31 g, 5.0 mmol) was hydrogenated in anhydrous THF (100 ml) in the presence of catalytic amount of 10% Pd/C at room temperature and 1 atm overnight. The catalyst was filtered off and 4-(hydroxymethyl)-5-methyl-1,3-dioxol-2-one (1.49 g, 11.0 mmol), HOBt (1.49 g, 11.0 mmol) were added. A solution of EDC.HCl (2.11 g, 11.0 mmol) and DMAP (1.34 g, 11.0 mmol) in DMF (60 ml) was added and the mixture was stirred at room temperature overnight. Solvents were evaporated and the residue was partitioned between EtOAc—H2O (1:1, 200 ml). The aqueous solution was extracted with EtOAc (100 ml) again and combined organic extracts were dried (MgSO4) and evaporated. The residue was chromatographed on a silica gel column in EtOAc→2% MeOH/EtOAc. Yield 2.13 g (84%) of oil.

$^1$H NMR (400 MHz, CDCl$_3$): 1.30-1.33 (m, 6H, CH$_3$ (Et)), 1.87 (ddd, 1H, $J_{1b-P}$=18.6, $J_{gem}$=15.4, $J_{1b-2}$=5.5, H-1b), 1.96-2.08 (m, 2H, H-3), 2.18, 2.19 (2×s, 2×3H, 4'-CH$_3$), 2.21 (ddd, $J_{1a-P}$=18.1, $J_{gem}$=15.4, $J_{1a-2}$=8.5, H-1a), 2.32-2.44 (m, 2H, H-4), 2.84 (m, 1H, H-2), 4.05-4.13 (m, 4H, CH$_2$ (Et)), 4.82-4.93 (m, 4H, 3'-CH$_2$).

$^{13}$C NMR (101 MHz, CDCl$_3$): 9.35, 9.37 (4'-CH$_3$), 16.36, 16.37 (2×d, $J_{CH3-P}$=5.9, CH$_3$(Et)), 27.72 (d, $J_{1-P}$=143.2, C-1), 27.86 (d, $J_{3-P}$=12.6, C-3), 30.88 (C-4), 38.96 (d, $J_{2-P}$=3.5, C-2), 53.84, 54.22 (3'-CH$_2$), 61.91-62.00 (m, CH$_2$ (Et)), 133.15, 133.30 (C-3'), 140.17, 140.30 (C-4'), 152.01, 152.05 (C-1'), 171.72 (C-5), 173.29 (d, $J_{C-2-1-P}$=8.6, COO).

ESI MS: 529 ([M+Na]$^+$).

HR ESI MS: calcd for C$_{20}$H$_{27}$O$_{13}$NaP 529.10815; found 529.10819.

(5-((5-methyl-2-oxo-1,3-dioxol-4-yl)methoxy)-2-(((5-methyl-2-oxo-1,3-dioxol-4-yl)methoxy)carbonyl)-5-oxopentyl)phosphonic acid TT-120814

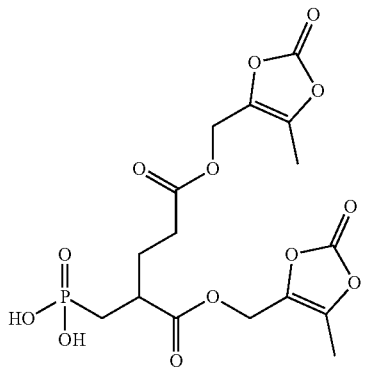 [SMILES: Cc1oc(=O)oc1COC(=O)CCC(CP(=O)(O)O)C(=O)OCc1oc(=O)oc1C]

A solution of bis((5-methyl-2-oxo-1,3-dioxol-4-yl)methyl) 2-((diethoxyphosphoryl)methyl) pentanedioate (253 mg, 0.5 mmol) in anhydrous acetonitrile (5 ml) was treated with Me$_3$SiBr (530 μl, 4.0 mmol) at 0° C. The solution was kept at 0° C. overnight. The volatiles were evaporated and the residue was codistilled with MeCN and treated with water (0.25 ml). The sample was purified on a C-18 reverse phase column in gradient H$_2$O→55% MeOH/H$_2$O. Yield 170 mg (75%).

ESI MS: 449 ([M−H]$^-$).

HR ESI MS: calcd for C$_{16}$H$_{18}$O$_{13}$P 449.04905; found 449.04877.

Bis((5-methyl-2-oxo-1,3-dioxol-4-yl)methyl) 2-((bis((5-methyl-2-oxo-1,3-dioxol-4-yl)methoxy)phosphoryl)methyl)pentanedioate TT-190215

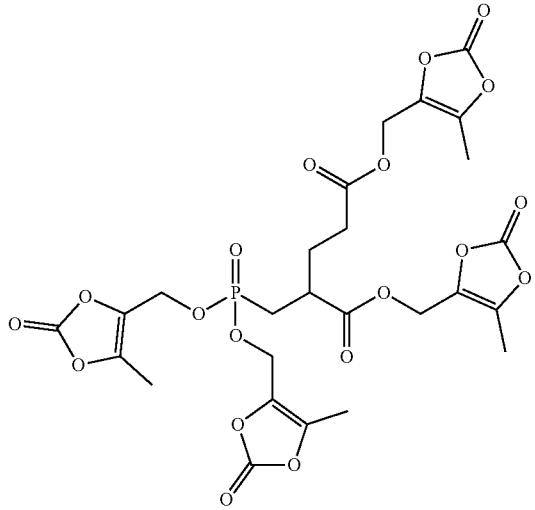 [SMILES: Cc1oc(=O)oc1COC(=O)CCC(CP(=O)(OCc1oc(=O)oc1C)OCc1oc(=O)oc1C)C(=O)OCc1oc(=O)oc1C]

A solution of bis((5-methyl-2-oxo-1,3-dioxol-4-yl)methyl) 2-((diethoxyphosphoryl)methyl) pentanedioate (250 mg, 0.494 mmol) in anhydrous acetonitrile (5 ml) was treated with Me$_3$SiBr (530 μl, 4.0 mmol) at 0° C. The solution was kept at 0° C. overnight. The volatiles were evaporated and the residue was codistilled with MeCN, dissolved in dioxane (5 ml) and treated with water (36 μl, 2.0 mmol). The solution was stirred 30 min at room temperature then toluen (5 ml) was added and the solvents were evaporated. To a solution of resulting phosphonic acid, triphenylphosphine (777 mg, 2.96 mmol) and 4-(hydroxymethyl)-5-methyl-1,3-dioxol-2-one (386 mg, 2.96 mmol) in THF (10 ml, DIAD (583 μl, 2.96 mmol) was added dropwise. The mixture was stirred 6 h at room temperature. The solvent was removed in vacuo and the residue was chromatographed on a silica gel column in EtOAc→4% MeOH/EtOAc. Yield 160 mg (48%).

$^1$H NMR (400 MHz, CDCl$_3$): 1.93-2.01 (m, 3H, H-3, H-1b), 2.19, 2.20 (3×s, 3H, 6H, 3H, 4×CH3), 2.24-2.45 (m, 3H, H-4, H-1a), 2.82 (m, 1H, H-2), 4.77-4.96 (m, 8H, O—CH2).

$^{13}$C NMR (101 MHz, CDCl$_3$): 9.24, 9.27, 9.29 (4×CH3), 27.90 (d, J3-P=14.0, C-3), 28.07 (d, J1-P=141.8, C-1), 30.67 (C-4), 38.51 (d, J2-P=3.7, C-2), 53.88, 54.40 (2×OCH2), 55.23, 55.37 (2×d, JCH2-O—P=6.0 and 5.8, CH2-O—P), 132.89-133.30 (m, C-3'), 140.23, 140.34, 140.51 (C-4'), 151.72, 151.75, 152.05, 152.07 (C-1'), 171.49 (C-5), 172.74 (d, JC-P=7.4, COO).

ESI MS: 697 ([M+Na]$^+$).

HR ESI MS: calcd for C$_{26}$H$_{27}$O$_{19}$NaP 697.07764; found 697.07752.

bis((5-methyl-2-oxo-1,3-dioxol-4-yl)methyl) 2-((hydroxy((5-methyl-2-oxo-1,3-dioxol-4-yl)methoxy)phosphoryl)methyl)pentanedioate TT-110814

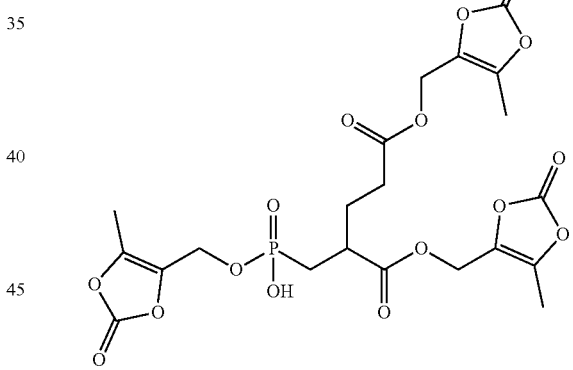

A solution of bis((5-methyl-2-oxo-1,3-dioxol-4-yl)methyl) 2-((bis((5-methyl-2-oxo-1,3-dioxol-4-yl)methoxy) phosphoryl)methyl)pentanedioate (256 mg, 0.38 mmol) and LiN3 (37 mg, 1.07 mmol) in DMF (2 ml) was stirred at room temperature overnight. The solvent was evaporated and the residue was purified on a silica gel column in 10-50% MeOH/EtOAc. Yield 136 mg (64%).

$^1$H NMR (400 MHz, CDCl$_3$): 1.74-2.07 (m, 4H, H-3, H-1), 2.16, 2.18, 2.18 (3×s, 9H, 3×CH$_3$), 2.26-2.41 (m, 2H, H-4), 2.78 (m, 1H, H-2), 4.69-4.96 (m, 6H, O—CH$_2$).

$^{13}$C NMR (101 MHz, CDCl$_3$): 9.02, 9.20, 9.22 (3×CH$_3$), 27.80-29.13 (C-1, C-3), 30.78 (C-4), 39.62 (C-2), 53.92, 54.28, 54.44 (3×OCH$_2$), 133.23, 133.33 (C-3'), 134.94 (d, J$_{3'-C-O-P}$=7.0, C-3'), 139.23, 140.39, 140.48 (C-4'), 152.22, 152.29, 152.46 (C-1'), 172.57 (C-5), 174.78 (m, COO).

ESI MS: 561 ([M−H]$^-$)

HR ESI MS: calcd for C$_{21}$H$_{22}$O$_{16}$P 561.06509; found 561.06496.

Example 3

Selective Deprotection of Phosphonate Diesters

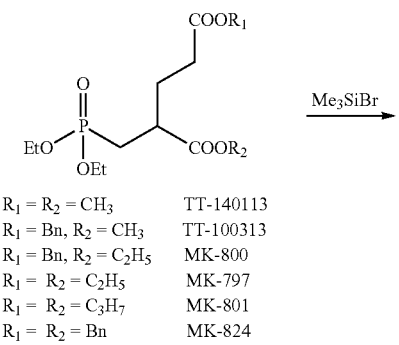

| | |
|---|---|
| $R_1 = R_2 = CH_3$ | TT-140113 |
| $R_1 = Bn, R_2 = CH_3$ | TT-100313 |
| $R_1 = Bn, R_2 = C_2H_5$ | MK-800 |
| $R_1 = R_2 = C_2H_5$ | MK-797 |
| $R_1 = R_2 = C_3H_7$ | MK-801 |
| $R_1 = R_2 = Bn$ | MK-824 |

Bromotrimethylsilane (9.3 mL; 70 mmol) was added at 0° C. to a solution of appropriate phosphonate diester (17.5 mmol) in acetonitrile (100 mL) and kept at 0° C. for 24 h. The solution was evaporated, the residue coevaporated with acetonitrile, followed by water and toluene. The crude product was purified by chromatography on silica gel in system chloroform-ethyl acetate-methanol (2:2:1).

The following compounds were prepared:

[5-(Methyloxy)-2-(methoxycarbonyl)-5-oxopentyl]phosphonic acid. TT-140113

Yield: 3.2 g (73%) of a colorless syrup. $^1$H NMR (CDCl$_3$, ppm) δ: 1.84 (m, 1H, H-1a); 1.97 (m, 2H, H-3); 2.15 (m, 1H, H-1b); 2.36 (m, 2H, H-4); 2.79 (m, 1H, H-2); 3.66 (s, 3H, R$_1$=Me); 3.69 (s, 3H, R$_2$=Me). $^{13}$C NMR (CDCl$_3$, ppm) δ: 29.53 (d, $J_{C,P}$=12.8, C-3); 30.33 (d, $J_{C,P}$=140.4, C-1); 32.10 (C-4); 40.89 (d, $J_{C,P}$=3.4, C-2); 52.43 (R$_1$=Me); 52.47 (R$_2$=Me); 174.83 (COOR$_1$); 176.44 (d, $J_{C,P}$=8.1, COOR$_2$). ESI MS, m/z:

[5-(Benzyloxy)-2-(methoxycarbonyl)-5-oxopentyl] phosphonic acid. TT-100313

Yield: 4.5 g (78%) of a colorless syrup. The crude product was used for the preparation of compound TT-110313 without purification and identification.

[5-(Benzyloxy)-2-(ethoxycarbonyl)-5-oxopentyl] phosphonic acid. MK-800

Yield: 4.0 g (66%) of a white waxy solid. ESI MS, m/z: 687.3 [2M–H]$^-$ (43), 343.1 [M–H]$^-$ (50). HRMS (ESI): For C$_{15}$H$_{20}$O$_7$P [M–H]$^-$ calculated: 343.09521; found: 34309513.

[5-Ethoxy-2-(ethoxycarbonyl)-5-oxopentyl]phosphonic acid. MK-797

Yield: 3.0 g (60%) of a colorless syrup. $^{31}$P{$^1$H} NMR (CDCl$_3$, ppm) δ: 26.70. $^1$H NMR (CDCl$_3$, ppm) δ: 1.29 (m, 6H, 2×CH$_3$, Et), 2.06 (m, 3H), 2.27 (m, 3H), 2.83 (m, 1H, H-2), 4.14 (m, 4H, 2×CH$_2$, Et). ESI MS, m/z: 563.3 [2M–H]$^-$ (100), 281.2 [M–H]$^-$ (62). HRMS (ESI): For C$_{10}$H$_{18}$O$_7$P [M–H]$^-$ calculated: 281.07956; found: 281.07958. Anal. Calcd. for C$_{10}$H$_{19}$O$_7$P: C, 42.56; H, 6.79; P, 10.97. Found: C, 42.07; H, 6.87; P, 10.59.

[5-Oxo-5-propoxy-2-(propoxycarbonyl)pentyl]phosphonic acid. MK-801

Yield: 3.6 g (67%) of a white waxy solid. $^{31}$P{$^1$H} NMR (CD$_3$OD, ppm) δ: 21.38. $^1$H NMR (CD$_3$OD, ppm) δ: 0.92 (m, 6H, 2×CH$_3$, Pr), 1.39 (m, 2H), 1.67 (m, 3H), 2.09 (m, 3H), 2.31 (m, 2H), 2.88 (m, 1H), 4.16 (m, 4H). ESI MS, m/z: 619.3 [2M–H]$^-$ (100), 309.1 [M–H]$^-$ (47). HRMS (ESI): For C$_{12}$H$_{22}$O$_7$P [M–H]$^-$ calculated: 309.11086; found: 309.11101.

[5-(Benzyloxy)-2-(benzyloxycarbonyl)-5-oxopentyl] phosphonic acid. MK-824

Yield: 6.0 g (85%) of a colorless syrup. ESI MS, m/z: 811.3 [2M–H]$^-$ (12), 405.1 [M–H]$^-$ (26).

Example 4

Esterification of Phosphonic Acids—POM Esters, POC Esters, Alkyl Esters

| | |
|---|---|
| $R_1 = Bn, R_2 = CH_3, R_3 = POC$ | MK-792 |
| $R_1 = Bn, R_2 = CH_3, R_3 = C_{10}H_{21}$ | MK-796 |
| $R_1 = R_2 = C_2H_5, R_3 = POM$ | MK-798 |
| $R_1 = Bn, R_2 = C_2H_5, R_3 = POM$ | MK-803 |
| $R_1 = Bn, R_2 = C_2H_5, R_3 = POC$ | MK-805 |
| $R_1 = R_2 = Bn, R_3 = POC$ | MK-825 |
| $R_1 = R_2 = Me, R_3 = POC$ | TT-010213 |
| $R_1 = R_2 = Me, R_3 = POM$ | TT-201212A |
| $R_1 = R_2 = Me, R_3 = (CH_2CH_2O)_6OEt$ | TT-250113 |

POC—Cl
(POM—Cl,
RBr,
R—OTs)
DBU,
dioxane

DBU (2 mmol) was added to a solution of appropriate phosphonic acid (1 mmol) in dry dioxane (10 mL) and then heated with POC—Cl (20 mmol, 80° C., 4 h) or POM-Cl (4 mmol, reflux, 6 h) or decyl bromide (2.3 mmol, reflux, 3 h) or 3,6,9,12,15,18-hexaoxaicosyl p-toluensulfonate (2.1 mmol, reflux, 6 h), respectively. The reaction course was monitored by TLC in system toluene-acetone (4:1); detection was performed by spraying of the TLC plate with a solution of phosphomolybdenic acid and heating. Reaction mixture was evaporated and the residue chromatographed on a silica gel column (200 mL) in system toluene-acetone (4:1)

for POM and POC esters, toluene-acetone (8:1) for decyl ester, or 12% MeOH/CHCl$_3$ for 3,6,9,12,15,18-hexaoxaicosyl ester.

The following compounds were prepared:

5-Benzyl 1-methyl 2-((bis{[(isopropoxycarbonyl)oxy]methoxy}phosphoryl)methyl)-pentanedioate. MK-792

Yield: 194 mg (34%) of a colourless syrup. $^{31}$P{$^1$H} NMR (CDCl$_3$, ppm) δ: 29.85. $^1$H NMR (CDCl$_3$, ppm) δ: 1.31-1.33 (m, 12H, CH$_3$ iPr), 1.96-2.06 (m, 3H, H-3, H-1b), 2.34-2.44 (m, 3H, H-4, H-1a), 2.84 (m, 1H, H-2), 3.69 (s, 3H, COOCH$_3$), 4.93 (2×septet, 2H, $J_{CH,CH3}$=6.3, 2×CH iPr), 5.11 (s, 2H, CH$_2$ Bn), 5.60-5.68 (m, 4H, 2×OCH$_2$O), 7.30-7.38 (m, 5H, H-2',3',4'). $^{13}$C NMR (CDCl$_3$, ppm) δ: 21.59 (CH$_3$ iPr), 28.16 (d, $J_{3,P}$=13.6, C-3), 28.54 (d, $J_{1,P}$=143.2, C-1), 31.34 (C-4), 38.65 (d, $J_{2,P}$=3.6, C-2), 52.15 (OCH$_3$), 66.41 (CH$_2$ Bn), 73.27 (CH iPr), 83.94 and 83.95 (2×d, $J_{C-O-P}$=6.2, OCH$_2$O), 128.25 (C-2'), 128.26 (C-4'), 128.54 (C-3'), 135.76 (C-1'), 153.11 and 153.13 (OC(O)O), 172.12 (C-5), 173.82 (d, $J_{C-C-C-P}$=8.7, 2-COO). ESI MS, m/z: 585.5 [M+Na]$^+$ (100), 563.5 [MH]$^+$ (31). HRMS (ESI): For C$_{24}$H$_{36}$O$_{13}$P [MH]$^+$ calculated: 563.18880; found: 563.18868.

5-Benzyl 1-methyl 2-((bis(decyloxy)phosphoryl)methyl)pentanedioate. MK-796

Yield: 351 mg (57%) of a colourless syrup. $^{31}$P{$^1$H} NMR (CDCl$_3$, ppm) δ: 28.39. $^1$H NMR (CDCl$_3$, ppm) δ: 0.90 (7, 6H, $J_{CH3,CH2}$=6.9, 2×CH$_3$, decyl), 1.30 (m, 28H, 14×CH$_2$, decyl), 1.65 (m, 4H, CH$_2$), 1.86 (ddd, 1H, 2.03 (m, 2H), 2.26 (ddd, 1H), 2.41 (m, 2H), 2.83 (tdd, 1H, H-2), 3.71 (s, 3H, COOCH$_3$), 4.00 (qd, 4H, 2×OCH$_2$, decyl), 5.13 (s, 2H, CH$_2$, Bn), 7.36 (m, 5H, H-arom.). ESI MS, m/z: 1243.8 [2M+Na]$^+$ (38), 633.4 [M+Na]$^+$ (100). HRMS (ESI): For C$_{34}$H$_{59}$O$_7$PNa [M+Na]$^+$ calculated: 633.38906; found: 633.38806.

Diethyl 2-({bis[(pivaloyloxy)methoxy]phosphoryl}methyl)pentanedioate. MK-798

Yield: 429 mg (84%) of a yellowish syrup. $^{31}$P{$^1$H} NMR (CDCl$_3$, ppm) δ: 29.46. $^1$H NMR (CDCl$_3$, ppm) δ: 1.25 (m, 24H, 8×CH$_3$, POM, Et), 1.99 (m, 3H), 2.34 (m, 3H), 2.80 (m, 1H, H-2), 4.17 (m, 4H, 2×CH$_2$, Et), 5.67 (m, 4H, 2×OCH$_2$O). ESI MS, m/z: 533.1 [M+Na]$^+$ (100). HRMS (ESI): For C$_{22}$H$_{39}$O$_{11}$PNa [M+Na]$^+$ calculated: 533.21222; found: 533.21221. Anal. Calcd. for C$_{22}$H$_{39}$O$_{11}$P: C, 51.76; H, 7.70; P, 6.07. Found: C, 51.98; H, 7.55; P, 6.01.

5-Benzyl 1-ethyl 2-({bis[(pivaloyloxy)methoxy]phosphoryl}methyl)pentanedioate. MK-803

Yield: 183 mg (32%) of a colourless syrup. $^{31}$P{$^1$H} NMR (CDCl$_3$, ppm) δ: 29.40. $^1$H NMR (CDCl$_3$, ppm) δ: 1.25 (m, 21H, 7×CH$_3$, POM, Et), 2.01 (m, 3H), 2.39 (m, 3H), 2.82 (m, 1H, H-2), 4.17 (q, 2H, $J_{CH2,CH3}$=7.1, CH$_2$, Et), 5.13 (s, 2H, CH$_2$ Bn), 5.66 (d, 2H, J=13.1, OCH$_2$O), 5.67 (d, 2H, J=13.1, OCH$_2$O), 7.36 (m, 5H, H-arom.). ESI MS, m/z: 595.3 [M+Na]$^+$ (100). HRMS (ESI): For C$_{27}$H$_{41}$O$_{11}$PNa [M+Na]$^+$ calculated: 595.22787; found: 595.22783.

5-Benzyl 1-ethyl 2-((bis{[(isopropoxycarbonyl)oxy]methoxy}phosphoryl)methyl)-pentanedioate. MK-805

Yield: 217 mg (38%) of a colourless syrup. $^{31}$P{$^1$H} NMR (CDCl$_3$, ppm) δ: 29.46. $^1$H NMR (CDCl$_3$, ppm) δ: 1.27 (t, 3H, $J_{CH3,CH2}$=7.1, CH$_3$, Et), 1.33 (d, 6H, $J_{CH3,CH}$=1.6, 2×CH$_3$, iPr), 1.34 (d, 6H, $J_{CH3,CH}$=1.6, 2×CH$_3$, iPr), 2.04 (m, 3H), 2.41 (m, 3H), 2.83 (m, 1H, H-2), 4.17 (q, 2H, $J_{CH2,CH3}$=7.1, CH$_2$, Et), 5.13 (s, 2H, CH$_2$, Bn), 5.66 (m, 4H, 2×OCH$_2$O, POC), 7.36 (m, 5H, H-arom.). ESI MS, m/z: 1175.7 [2M+Na]$^+$ (6), 599.3 [M+Na]$^+$ (100). HRMS (ESI): For C$_{25}$H$_{38}$O$_{13}$PNa [M+Na]$^+$ calculated: 577.20445; found: 577.20468.

Dibenzyl 2-((bis{[(isopropoxycarbonyl)oxy]methoxy}phosphoryl)methyl)pentanedioate. MK-825

Yield: 247 mg (39%) of a colourless syrup. $^{31}$P{$^1$H} NMR (CDCl$_3$, ppm) δ: 29.31. $^1$H NMR (CDCl$_3$, ppm) δ: 1.34 (4×d, 12H, 4×CH$_3$, POC), 2.04 (m, 3H), 2.37 (m, 3H), 2.90 (m, 1H, H-2), 4.93 (m, 2H, 2×CH, POC), 5.11 (s, 2H, CH$_2$, Bn), 5.14 (d, 2H, CH$_2$, Bn), 5.63 (m, 4H, 2×OCH$_2$O), 7.35 (m, 10H, H-arom.). ESI MS, m/z: 661.2 [M+Na]$^+$ (100).

Dimethyl 2-((bis{[(isopropoxycarbonyl)oxy]methoxy}phosphoryl)methyl)-pentanedioate. TT-010213

Yield: 177 mg (37%) of a colourless syrup. $^1$H NMR (CDCl$_3$, ppm) δ: 1.31 (4×d, 12H, 4×Me, POM); 1.98 (m, 2H, H-3); 2.00 (ddd, 1H, $J_{1a,P}$=19.1, $J_{gem}$=15.6, $J_{1a,2}$=5.4, H-1a); 2.32 (m, 2H, H-4); 2.37 (ddd, 1H, $J_{1b,P}$=19.0, $J_{gem}$=15.6, $J_{1a,2}$=8.6, H-1b); 2.82 (m, 1H, H-2); 3.65 (s, 3H, Me, R$_1$); 3.70 (s, 3H, Me, R$_2$); 4.92 (2×sept, 2H, 2×CH, POC); 5.58-5.68 (m, 4H, 2×CH$_2$, POC). $^{13}$C NMR (CDCl$_3$, ppm) δ: 21.58 (4×CH$_3$, POC); 28.13 (d, $J_{C,P}$=13.5, C-3); 28.45 (d, $J_{C,P}$=143.3, C-1); 31.09 (d, $J_{C,P}$=1.1, C-4); 38.62 (d, $J_{C,P}$=3.6, C-2); 51.69 (Me, R$_1$); 52.17 (Me, R$_2$); 73.28 (CH, POC); 83.91, 83.92 (2×d, $J_{C,P}$=6.2, 2×CH$_2$, POC); 153.10, 153.12 (2×CO, POC); 172.74 (COOR$_1$); 173.83 (d, $J_{C,P}$=8.9, COOR$_2$). ESI MS, m/z:

Dimethyl 2-((bis{[(pivaloyloxy)methoxy]phosphoryl}methyl)pentanedioate. TT-201212A Yield: 195 mg (40%) of a colourless syrup. $^1$H NMR (CDCl$_3$, ppm) δ: 1.22 (2×s, 2×9H, 6×Me, POM); 1.91-2.03 (m, 3H, H-1a+H-3); 2.26-2.38 (m, 3H, H-1b+H-4); 2.80 (dtt, 1H, $J_{2,P}$=13.5, $J_{2,1b}$=$J_{2,3b}$=8.4, $J_{2,1a}$=$J_{2,3a}$=5.5, H-2); 3.65 (s, 3H, Me, R$_1$); 3.70 (s, 3H, Me, R$_2$); 5.61-5.67 (m, 4H, 2×CH$_2$, POM). $^{13}$C NMR (CDCl$_3$, ppm) δ: 26.79 (6×CH$_3$, POM); 28.14 (d, $J_{C,P}$=13.3, C-3); 28.69 (d, $J_{C,P}$=142.8, C-1); 31.07 (d, $J_{C,P}$=1.1, C-4); 38.70 (C, POM); 38.71 (d, $J_{C,P}$=3.5, C-2); 51.71 (Me, R$_1$); 52.17 (Me, R$_2$); 81.36, 81.39 (2×d, $J_{C,P}$=6.2, 2×CH$_2$, POM); 172.72 (COOR$_1$); 173.87 (d, $J_{C,P}$=9.1, COOR$_2$). 176.80, 176.81 (2×CO, POM). ESI MS, m/z: 505.2 [M+Na]$^+$ (100). HRMS (ESI): For C$_{20}$H$_{35}$O$_{11}$PNa [M+Na]$^+$ calculated: 505.18092; found: 505.18099.

Dimethyl 2-((bis((3,6,9,12,15,18-hexaoxaicosyl)oxy)phosphoryl)methyl)pentanedioate TT-250113

Yield: 342 mg (41%) of a colourless syrup. $^1$H NMR (CDCl$_3$, ppm) δ: 1.20 (t, 6H, $J_{14',13'}$=7.0, H-14'); 1.94 (ddd, 1H, $J_{1a,P}$=18.8, $J_{gem}$=15.5, $J_{1a,2}$=5.6, H-1a); 1.98 (m, 2H, H-3); 2.28 (ddd, 1H, $J_{1b,P}$=18.5, $J_{gem}$=15.5, $J_{1b,2}$=8.4, H-1b); 2.33 (m, 2H, H-4); 2.82 (m, 1H, H-2); 3.51 (q, 4H, $J_{13',14'}$=7.0, H-13'); 3.56-3.68 (m, 44H, H-2' to H-12'); 3.65 (s, 3H, Me, $R_1$); 3.69 (s, 3H, Me, $R_2$); 4.15 (m, 4H, H-1'). $^{13}$C NMR (CDCl$_3$, ppm) δ: 15.11 (C-14'); 27.65 (d, $J_{C,P}$=143.3, C-1); 28.17 (d, $J_{C,P}$=12.6, C-3); 31.16 (d, $J_{C,P}$=1.0, C-4); 38.99 (d, $J_{C,P}$=3.6, C-2); 51.66 (Me, $R_1$); 52.04 (Me, $R_2$); 64.71, 64.76 (2xd, $J_{C,P}$=5.9, 2×C-1'); 66.60 (C-13'); 70.60-69.77 (m, C-2' to C-12'); 170.90 (COOR$_1$); 174.32 (d, $J_{C,P}$=9.2, COOR$_2$). ESI MS, m/z: 861.5 [M+Na]$^+$ (100). HRMS (ESI): For $C_{36}H_{72}O_{19}P$ [M+H]$^+$ calculated: 839.43999; found: 839.44023.

Example 5

Esterification of Phosphonic Acids—Alkyl Salicylyl Esters

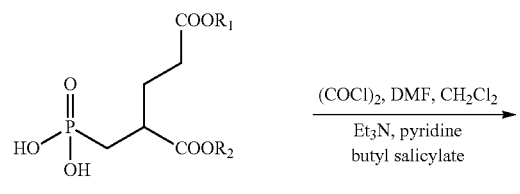

R$_1$ = Bn, R$_2$ = CH$_3$ MK-794
R$_1$ = R$_2$ = CH$_3$ TT-100113

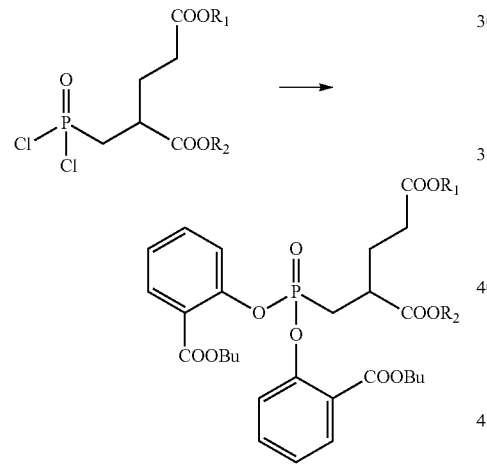

Catalytic amount of DMF (10 μL), followed by oxalyl chloride (0.6 mL; 7 mmol) were added to a solution of phosphonic acid (1 mmol) in dry dichloromethane (10 mL). The mixture was stirred for 2 h and evaporated. The residue (intermediary phosphochloridate) was dissolved in dichloromethane (5 mL), cooled to −10° C. and dry pyridine (0.16 mL) was added dropwise. The resulting mixture was immediately added to a cooled (−30° C.) mixture of butyl salicylate (0.4 g; 2.1 mmol) and triethyl amine (0.85 mL) in dichloromethane (8 mL). The reaction mixture was warmed slowly to room temperature, then stirred for 12 h and evaporated. The residue was chromatographed on a column of silica gel (80 mL) in system toluene-acetone (10:1). The following compounds were prepared:

5-Benzyl 1-methyl 2-({bis[2-(butoxycarbonyl)phenoxy]phosphoryl}methyl)pentane-dioate. MK-794

Yield: 0.41 g (60%) of a yellowish syrup. $^{31}$P{$^1$H} NMR (CDCl$_3$, ppm) δ: 23.45. $^1$H NMR (400 MHz, CDCl$_3$, ppm) δ: 0.965 (t, 3H, $J_{CH3,CH2}$=7.4, CH$_3$), 0.968 (t, 3H, $J_{CH3,CH2}$=7.4, CH$_3$), 1.46 (m, 4H, CH$_2$), 1.73 (m, 4H, CH$_2$), 2.18 (m, 2H), 2.51 (m, 3H), 2.80 (m, 1H), 3.18 (m, 1H), 3.66 (s, 3H, COOCH$_3$), 4.29 (2×t, 4H, $J_{CH2,CH2}$=6.7, OCH$_2$ (Bu)), 5.11 (s, 2H, CH$_2$ (Bn)), 7.23 (m, 4H, H-arom.), 7.34 (m, 5H, H-arom.), 7.40 (m, 2H, H-arom.), 7.88 (m, 2H, H-arom.). ESI MS, m/z: 1387.3 [2M+Na]$^+$ (12), 705.1 [M+Na]$^+$ (100), 683.1 [MH]$^+$ (48). HRMS (ESI): For $C_{36}H_{43}O_{11}PNa$ [M+Na]$^+$ calculated: 705.24352; found: 705.24280.

Dimethyl 2-({bis[2-(butoxycarbonyl)phenoxy]phosphoryl}methyl)pentanedioate. TT-100113

Yield: 0.48 g (79%) of a yellowish syrup. $^1$H NMR (CDCl$_3$, ppm) δ: 0.95 (2×t, 6H, $J_{4''',3'''}$=7.4, H-4'''); 1.43 (m, 4H, H-3'''); 1.68-1.74 (m, 4H, H-2'''); 2.13 (m, 2H, H-3); 2.41 (m, 2H, H-4); 2.50 (ddd, 1H, $J_{1a,P}$=19.8, $J_{gem}$=15.5, $J_{1a,2}$=6.1, H-1a); 2.79 (ddd, 1H, $J_{1b,P}$=19.4, $J_{gem}$=15.5, $J_{1b,2}$=7.7, H-1b); 3.18 (m, 1H, H-2); 3.64 (s, 3H, Me, $R_1$); 3.65 (s, 3H, Me, $R_2$); 4.28 (2×t, 4H, $J_{1'',2''}$=6.8, H-1''); 7.19 (m, 2H, H-5'); 7.21 (m, 2H, H-3'); 7.39 (m, 2H, H-4'); 7.86 (m, 2H, H-6'). $^{13}$C NMR (CDCl$_3$, ppm) δ: 13.70 (C-4'''); 19.18 (C-3'''); 28.17 (d, $J_{C,P}$=12.4, C-3); 28.37 (d, $J_{C,P}$=144.7, C-1); 30.63 (C-2'''); 31.24 (d, $J_{C,P}$=0.8, C-4); 38.76 (d, $J_{C,P}$=3.4, C-2); 51.59 (Me, $R_1$); 52.04 (Me, $R_2$); 65.03, 65.05 (C-1''); 122.49, 122.54 (2×d, $J_{C,P}$=0.9, C-3'); 123.36, 123.40 (C-1'); 124.90, 124.91 (2×d, $J_{C,P}$=1.4, C-5'); 133.52, 133.55 (2×d, $J_{C,P}$=0.6, C-6'); 133.34, 133.35 (C-4'); 149.12, 149.13 (2×d, $J_{C,P}$=9.4, C-2'); 164.64, 164.67 (2×d, $J_{C,P}$=1.1; COOBu); 172.99 (COOR$_1$); 174.20 (d, $J_{C,P}$=11.0, COOR$_2$). ESI MS, m/z: 629.3 [M+Na]$^+$ (100). HRMS (ESI): For $C_{30}H_{39}O_{11}PNa$ [M+Na]$^+$ calculated: 629.21222; found: 629.21169.

Example 6

Synthesis of Bis Amidates

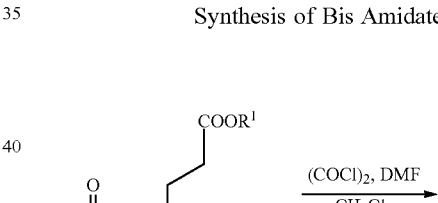

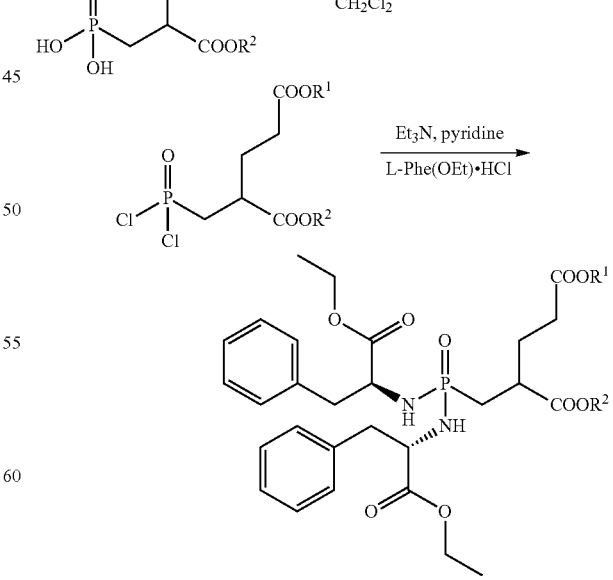

R$_1$ = R$_2$ = CH$_3$ TT-280113

Catalytic amount of DMF (10 μL), followed by oxalyl chloride (0.6 mL; 7 mmol) were added to a solution of phosphonic acid (1 mmol) in dry dichloromethane (10 mL). The mixture was stirred for 2 h and evaporated. The residue (intermediary phosphochloridate) was dissolved in dichloromethane (5 mL), cooled to −10° C. and dry pyridine (0.16 mL) was added dropwise. The resulting mixture was immediately added to a cooled (−30° C.) mixture of 1-phenylalanine ethyl ester hydrochloride (0.48 g; 2.1 mmol) and triethyl amine (0.85 mL) in dichloromethane (8 mL). The reaction mixture was warmed slowly to room temperature, then stirred overnight and finally washed with an aqueous solution of citric acid (20 ml). Organic portion was dried and concentrated. The residue was chromatographed on a column of silica gel (80 mL) in system MeOH-EtOAc-CHCl$_3$ (4:50:50).

The following compound was prepared:

Dimethyl 2-((bis(((S)-1-ethoxy-1-oxo-3-phenylpropan-2-yl)amino)phosphoryl)methyl)pentanedioate TT-280113

Yield: 0.39 g (48%) of a yellowish syrup (mixture of diastereomers). $^1$H NMR (CDCl$_3$, ppm) δ: 1.20, 1.21, 1.23 (4×t, 6H, J$_{2'',1''}$=7.1, H-2''); 1.19, 1.35 (2×m, 1H, H-1a); 1.73-1.98 (m, 3H, H-1b+H-3); 2.13-2.32 (m, 2H, H-4); 2.59, 2.73 (m, 1H, H-2); 2.77, 2.85, 2.95, 3.07 (4×m, 4H, H-3'); 3.58, 3.61 (2×s, 3H, Me, R$_2$); 3.65, 3.66 (2×s, 3H, Me, R$_1$); 3.95, 4.04 (2×m, 2H, H-1''); 4.07-4.28 (m, 4H, H-2'+H-1''); 7.10, 7.18 (2×m, 4H, H-5'); 7.20-7.32 (m, 6H, H-6'+H-7'). $^{13}$C NMR (CDCl$_3$, ppm) δ: 14.04, 14.05, 14.08 (C-2''); 28.69, 28.81 (2×d, J$_{C,P}$=14.0 and 15.0, C-3); 30.91 (2×d, J$_{C,P}$=115.9, C-1); 31.01 (C-4); 39.11, 39.25 (2×d, J$_{C,P}$=3.3 and 3.6, C-2); 40.30, 40.46, 40.81, 40.93 (4×d, J$_{C,P}$=4.4, 4.5, 4.9 and 5.4, C-3'); 51.66, 51.67 (Me, R$_1$); 52.07, 52.13 (Me, R$_2$); 53.56, 53.94, 53.96, 54.37 (C-2'); 61.21, 61.22, 61.25, 61.33 (C-1'); 126.82, 126.87, 126.90, 126.91 (C-7'); 128.36, 128.41, 128.42, 128.44 (C-6'); 129.47, 129.59, 129.65, 129.69 (C-5'); 136.30, 136.37, 136.64, 136.67 (C-4'); 172.95, 172.98, 173.00, 173.02 (COOR$_1$); 173.16, 173.22 (2×d, J$_{C,P}$=3.1 and 2.4, C-1'); 175.03, 175.45 (2×d, J$_{C,P}$=4.8 and 4.1, COOR$_2$). ESI MS, m/z: 626.9 [M+Na]$^+$ (100). HRMS (ESI): For C$_{30}$H$_{41}$O$_9$N$_2$PNa [M+Na]$^+$ calculated: 627.24419; found: 627.24396.

Example 7

Synthesis of Monoesters

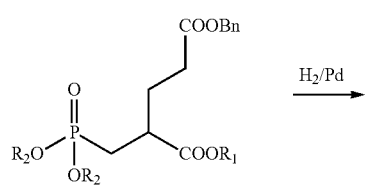

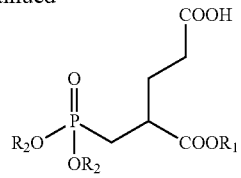

| | | |
|---|---|---|
| R$_1$ = CH$_3$, R$_2$ = POM | | TT 150313 |
| R$_1$ = CH$_3$, R$_2$ = POC | | MK-793 |
| R$_1$ = CH$_3$, R$_2$ = butyl salicylyl | | MK-795 |
| R$_1$ = CH$_3$, R$_2$ = C$_{10}$H$_{21}$ | | MK-799 |
| R$_1$ = C$_2$H$_5$, R$_2$ = POM | | MK-804 |
| R$_1$ = C$_2$H$_5$, R$_2$ = POC | | MK-806 |

10% Pd/C (90 mg) was added to a solution of benzyl ester (1 mmol) in THF (30 mL) and the mixture was hydrogenated at room temperature and atmospheric pressure for 15 h. The catalyst was removed by filtration through a pad of Celite. The crude filtrate was finally purified by additional filtration through a Whatman nylon membrane filter. The filtrate was evaporated to give a desired monoester as a colorless syrup in yield 90-100%. The reaction course was monitored by TLC in system ethyl acetate-acetone-ethanol-water (18:3:2:2), detection was performed by spraying with bromocresol green solution and heating (white spot of the product).

The following products were prepared:

4-({Bis[(pivaloyloxy)methoxy]phosphoryl}methyl)-5-methoxy-5-oxopentanoic acid. TT 150313

$^1$H NMR (400 MHz, CDCl$_3$, ppm) δ:1.25 (s, 18H, 6×CH$_3$), 2.02 (m, 3H), 2.38 (m, 3H), 2.85 (m, 1H, H-2), 3.73 (s, 3H, COOCH$_3$), 5.67 (d, 4H, J=13.1, 2×OCH$_2$O).

4-((Bis{[(isopropoxycarbonyl)oxy]methoxy}phosphoryl)methyl)-5-methoxy-5-oxopentanoic acid. MK-793

$^{31}$P{$^1$H} NMR (CDCl$_3$, ppm) δ: 30.01. $^1$H NMR (400 MHz, CDCl$_3$, ppm) δ: 1.32-1.34 (m, 12H, CH$_3$), 1.98-2.08 (m, 3H, H-3, H-1b), 2.33-2.44 (n, 3H, H-4, H-1a), 2.86 (m, 1H, H-2), 3.72 (s, 3H, COOCH$_3$), 4.94 (2×sept, 2H, OCH (CH$_3$)$_2$), 5.61-5.69 (m, 4H, OCH$_2$O). 13C NMR (CDCl$_3$, ppm) δ: 21.59 (CH$_3$), 27.85 (d, J$_{3,P}$=12.9, C-3), 28.40 (d, J$_{1,P}$=143.3, C-1), 30.94 (C-4), 38.51 (d, J$_{2,P}$=3.6, C-2), 52.21 (OCH$_3$), 73.52 (CH iPr), 84.02 and 84.03 (2×d, J$_{C,P}$=6.3, OCH$_2$O), 153.12 and 153.15 (O(CO)O), 173.83 (d, J$_{C,P}$=9.6, COOMe), 176.38 (COOH). ESI MS, m/z: 495.4 [M+Na]$^+$ (100), 473.4 [MH]$^+$ (58). HRMS (ESI): For C$_{17}$H$_{29}$O$_{13}$PNa [M+Na]$^+$ calculated: 495.12380; found: 495.12378.

4-({Bis[2-(butoxycarbonyl)phenoxy]phosphoryl}methyl)-5-methoxy-5-oxopentanoic acid MK-795

$^{31}$P{$^1$H} NMR (CDCl$_3$, ppm) δ: 24.12. $^1$H NMR (400 MHz, CDCl$_3$, ppm) δ: 0.95 (m, 6H, CH$_3$), 1.44 (m, 4H, CH$_2$CH$_3$), 1.72 (m, 4H, CH$_2$CH$_2$CH$_3$), 2.05-2.19 (m, 2H, H-3), 2.39-2.57 (m, 3H, H-1a, H-4), 2.82 (ddd, 1H, J$_{1b,P}$=19.6, J$_{gem}$=15.6, J$_{1b,2}$=7.6, H-1b), 3.20 (m, 1H, H-2), 3.66 (s, 3H, OCH$_3$), 4.27-4.31 (m, 4H, COOCH$_2$), 7.19-7.25 (m, 4H, H-arom.), 7.40 (m, 2H, H-arom.), 7.87 (m, 2H, H-arom.). $^{13}$C NMR (CDCl$_3$, ppm) δ: 13.61 (CH$_3$), 19.11 (CH$_2$CH$_3$), 27.85 (d, J$_{3,P}$=11.9, C-3), 28.28 (d, J$_{1,P}$=144.8, C-1), 30.58 (CH$_2$CH$_2$CH$_3$), 31.12 (C-4), 38.62 (d, J$_{2,P}$=3.1, C-2), 51.96 (OCH$_3$), 65.01 and 65.02 (2×OCH$_2$), 122.43-122.50 (m, C-3'), 123.31-123.37 (m, C-1'), 124.91 (C-5'), 131.48 and 131.50 (C-6'), 133.32 (C-4'), 149.01-149.10 (m, C-2'), 164.59 and 164.62 (COOBu), 174.08 (d, J$_{C,P}$=11.5, COOMe), 177.32 (COOH). ESI MS, m/z: 615.2 [M+Na]$^+$ (100). HRMS (ESI): For C$_{29}$H$_{37}$O$_{11}$PNa [M+Na]$^+$ calculated: 615.19657; found: 615.19577.

4-{[Bis(decyloxy)phosphoryl]methyl}-5-methoxy-5-oxopentanoic acid. MK-799

$^{31}$P{$^1$H} NMR (CDCl$_3$, ppm) δ: 29.45. $^1$H NMR (400 MHz, CDCl$_3$, ppm) δ: 0.88 (t, 6H, J$_{CH3,CH2}$=7.1, CH$_3$ (H-10')), 1.23-1.36 (m, 28H, CH$_2$ (H-3'-H-9')), 1.61-1.67 (m, 4H, CH$_2$ (H-2')), 1.90 (ddd, 1H, J$_{1a,P}$=18.5, J$_{gem}$=15.5, J$_{1a,2}$=5.5, H-1a), 1.95-2.05 (m, 2H, H-3), 2.26 (ddd, 1H, J$_{1b,P}$=18.3, J$_{gem}$=15.5, J$_{1b,2}$=8.2, H-1b), 2.31-2.43 (m, 2H, H-4), 2.84 (m, 1H, H-2), 3.70 (s, 3H, COOCH$_3$), 3.98-4.02 (m, 4H, CH$_2$ (H-1')). $^{13}$C NMR (CDCl$_3$, ppm) δ: 14.09 (C-10'), 22.65 (C-9'), 25.47 (C-3'), 27.45 (d, J$_{1,P}$=142.9, C-1), 28.14 (d, J$_{3,P}$=12.1, C-3), 29.16 (C-4'), 29.28 and 29.51 (C-5',6',7'), 30.46 (d, J$_{2',P}$=6.1, C-2'), 31.12 (C-4), 31.87 (C-8'), 38.92 (d, J$_{2,P}$=3.5, C-2), 52.01 (OCH$_3$), 66.05-66.11 (m, C-1'), 174.41 (d, J$_{C,P}$=9.1, COOMe), 176.11 (COOH). −ESI MS, m/z: 1039.8 [2M−H]$^-$ (10), 519.4 [M−H]$^-$ (100). HRMS (−ESI): For C$_{27}$H$_{52}$O$_7$P [M−H]$^-$ calculated: 519.34561; found: 519.34549.

4-({Bis[(pivaloyloxy)methoxy]phosphoryl}methyl)-5-ethoxy-5-oxopentanoic acid. MK-804

$^{31}$P{$^1$H} NMR (CDCl$_3$, ppm) δ: 29.56. $^1$H NMR (400 MHz, CDCl$_3$, ppm) δ: 1.25 (m, 21H, CH$_3$), 2.01 (m, 3H), 2.37 (m, 3H), 2.83 (ddd, 1H), 4.18 (m, 2H, CH$_2$CH$_3$), 5.68 (d, 4H, J=12.9, OCH$_2$O). ESI MS, m/z: 505.1 [M+Na]$^+$ (100). HRMS (ESI): For C$_{20}$H$_{35}$O$_{11}$PNa [M+Na]$^+$ calculated: 505.18092; found: 505.18109.

4-((Bis{[(isopropoxycarbonyl)oxy]methoxy}phosphoryl)methyl)-5-ethoxy-5-oxopentanoic acid. MK-806

$^{31}$P{$^1$H} NMR (CDCl$_3$, ppm) δ: 29.72. $^1$H NMR (400 MHz, CDCl$_3$, ppm) δ: 1.30 (m, 15H, CH$_3$), 2.03 (m, 3H), 2.40 (m, 3H), 2.85 (m, 1H), 4.18 (q, 2H, J$_{CH2,CH3}$=7.1, CH$_2$CH$_3$), 4.94 (dq, 2H, J=12.4 and 6.2, OCH(CH$_3$)$_2$), 5.61-5.75 (m, 4H, OCH$_2$O). ESI MS, m/z: 509.0 [M+Na]$^+$ (100). HRMS (ESI): For C$_{18}$H$_{31}$O$_{13}$PNa [M+Na]$^+$ calculated: 509.13945; found: 509.13962.

Example 8

Synthesis of Dicarboxylic Acid

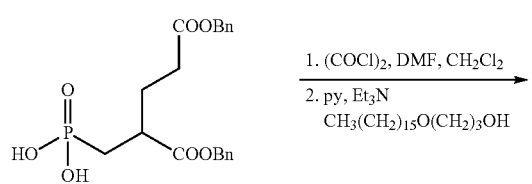

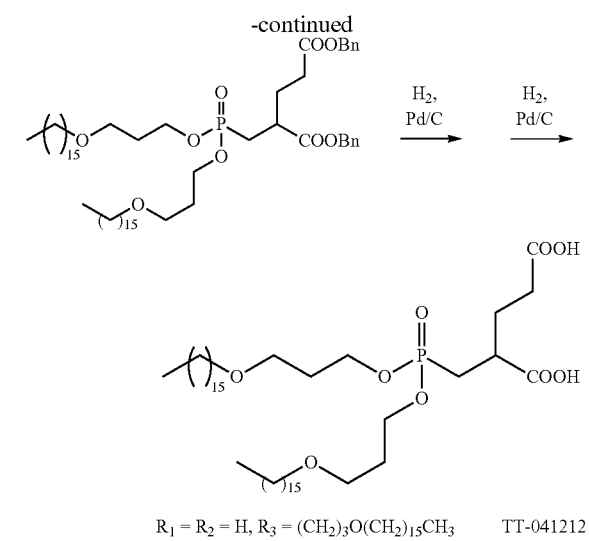

Catalytic amount of DMF (10 μL), followed by oxalyl chloride (0.6 mL; 7 mmol) were added to a solution of compound MK-824 (1 mmol) in dry dichloromethane (10 mL). The mixture was stirred for 2 h and evaporated. The residue (intermediary phosphochloridate) was dissolved in dichloromethane (5 mL), cooled to −10° C. and dry pyridine (0.16 mL) was added dropwise. The resulting mixture was immediately added to a cooled (−30° C.) mixture of hexadecyloxypropyl alcohol (0.63 g; 2.1 mmol) and triethyl amine (0.85 mL) in dichloromethane (8 mL). The reaction mixture was warmed slowly to room temperature, then stirred for 12 h and evaporated. The residue was chromatographed on a column of silica gel (80 mL) in system toluene-acetone (10:1). The fractions containing phosphonic ester intermediate were evaporated (580 mg, 60%), the residue was hydrogenated in THF (30 mL) in the presence of 10% Pd/C (cat.) at atmospheric pressure for 24 h. The catalyst was removed by filtration through a pad of celite. The crude filtrate was finally purified by additional filtration through a Whatman nylon membrane filter. The filtrate was evaporated to give a desired monoester which was crystallized from hexane in freezer (−20° C.).

The following compound was prepared:

2-((Bis(3-(hexadecyloxy)propoxy)phosphoryl)methyl)pentanedioic acid. TT-041212

Yield 670 mg (85%) of crystals. $^1$H NMR (CDCl$_3$, ppm) δ: 0.87 (t, 6H, J$_{19',18'}$=7.0, H-19'); 1.19-1.35 (m, 52H, H-6' to H-18'); 1.54 (m, 4H, H-5'); 1.90 (m, 1H, H-1a); 1.91 (m, 4H, H-2'); 2.04 (m, 2H, H-3); 2.30 (ddd, 1H, J$_{1b,P}$=18.2, J$_{gem}$=15.6, J$_{1b,2}$=8.5, H-1b); 2.47 (m, 2H, H-4); 2.83 (m, 1H, H-2); 3.39 (t, 4H, J$_{4',5'}$=6.8, H-4'); 3.48 (m, 4H, H-3'); 4.12 (m, 4H, H-1'). $^{13}$C NMR (CDCl$_3$, ppm) δ: 14.11 (C-19'); 22.68 (C-18'); 26.13 (C-6'); 27.24 (d, J$_{C,P}$=142.3, C-1); 28.04 (d, J$_{C,P}$=12.6, C-3); 29.70-29.36 (m, C-5'+C-7' to C-16'); 30.64, 30.66 (2×d, J$_{C,P}$=6.4, C-2'); 31.43 (C-4); 31.91 (C-17'); 39.11 (bd, J$_{C,P}$=3.3, C-2); 63.42 (d, J$_{C,P}$=6.5, C-1'); 66.46 (C-3'); 71.23 (C-4'); 177.19 (C-5); 178.06 (d, J$_{C,P}$=8.4, C-6). Elem. An. for C$_{44}$H$_{87}$O$_9$P calc.: C 66.80, H 11.08, P 3.92; found: C 66.93, H 11.18, P 3.79.

Structure numbering for NMR assignment.

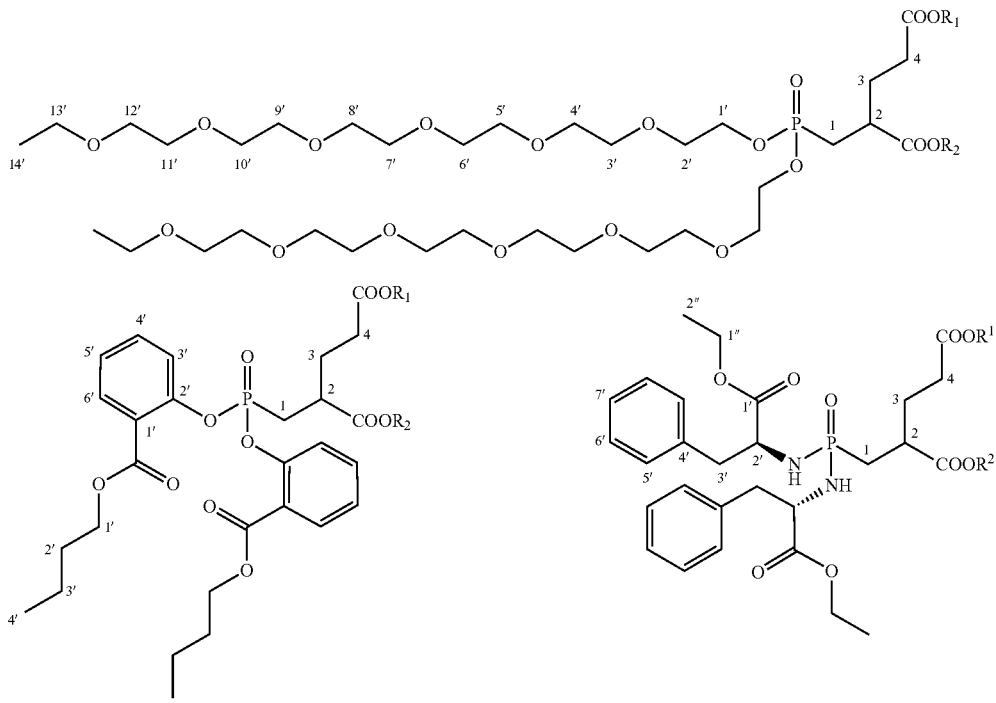

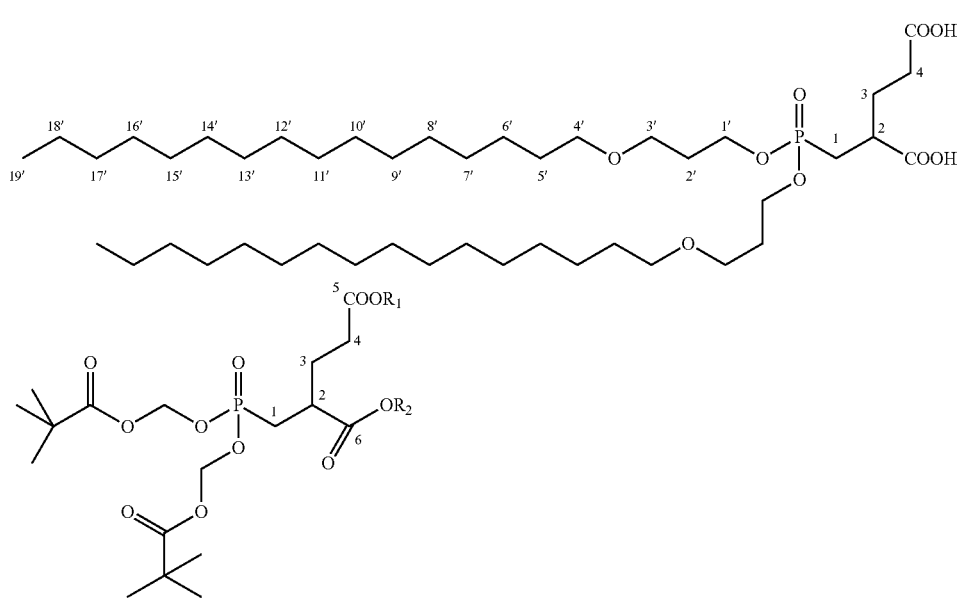

Example 9

Simple Alkyl Esters are not Effective 2PMPA Prodrugs

In general, the prodrugs were screened by an in vitro metabolic stability screen, and if positive, followed by an in vivo single time point pharmacokinetic study, and in select cases, an in vivo full time course pharmacokinetic study (FIG. 3). In this Example, the four acidic functional groups in 2-PMPA were systematically capped. The carboxylic acids were first masked with simple alkyl esters (Compounds 1, 2, and 3). In vitro chemical and metabolic stability of the prodrugs then were conducted, following 60 min incubation in plasma stability screens for prodrugs. Simple carboxylic esters like 1, 2 and 3, unexpectedly, turned out to be too stable, likely due to a very hydrophilic nature of the phophonate containing part of their molecules (FIG. 4 shows the stability screen for compound 1).

Example 10

Capping Both Phosphonates and Alpha Carboxylate Critical for Enhancing Permeability Masking of the phosphonate while keeping the carboxylates free as in the bis-isopropyloxycarbonyl methyl derivative (bis-POC, 4) and bis-pivaloyloxy methyl derivative (bis POM, 5) below alone is not feasible because of the chemical instability of those derivatives. The likely cause is direct participation of the α-carboxylate in the hydrolysis of the POC or POM group. Combination of both approaches as illustrated by example below renders compounds 6 and 7 with good compound penetrability. These compounds are, however, only converted to the corresponding carboxylate ester 1 which is stable in plasma and did not show the ability to release 2-PMPA. Very similar results were obtained with corresponding diethyl esters. In vitro metabolic stability of the 2-PMPA prodrugs 6 and 7 also were conducted. These prodrugs were found to be stable to chemical hydrolysis and unstable in mouse plasma and mouse liver microsomes (FIG. 5 shows the stability screen for compound 6).

Single time point pharmacokinetic studies were then performed on the 2-PMPA prodrugs to evaluate for enhancement in prodrug permeability and PMPA release. FIG. 6 shows the concentrations of 6, 7 and 8 tested and their comparison to 2-PMPA following oral administration at 30 mg/kg equivalent dose of 2-PMPA. Compounds 6 and 7 showed 25-50 fold enhancement in permeability when compared to 2-PMPA alone. More importantly, 8 with a free γ-carboxylate also showed similar enhancement in permeability. However no release of 2-PMPA was observed from any of these prodrugs and thus further optimization was needed. Since it is the α-carboxylate responsible for the instability of bis-POC and bis-POM compounds 4 and 5, derivatization of the γ-carboxylate was unnecessary as prodrugs with free γ-carboxylate 8 and 9 also exhibited good oral availability. But even in this case, the bioconversion only proceeded mostly to monoester 10. This was also the case of corresponding ethyl esters (not shown).

Example 11

Pivaloyloxymethyl (POM) and Propyloxycarbonyloxymethyl (POC) on Alpha Carboxylate Found to be Critical for Enhancement of Permeability and Release of Free 2PMPA In vitro metabolic stability screens of compounds JHU 2106 and 2108-2112 in mouse plasma and liver subcellular fractions are shown in FIGS. 7-9 and Tables 2-7. Compound JHU 2106, comprising methyl esters, was found to be too stable and therefore hindered the release of 2-PMPA (FIG. 7A, Table 2). Compound JHU 2108 was also found to be too stable in some of the samples (FIG. 7B, Table 3). Compound JHU 2109 was found to fall apart easily even in HBSS buffer and therefore would not even be able to get metabolized (FIG. 8A, Table 4). Compounds JHU 2110, 2111, and 2112 were found to be stable in HBSS buffer and were able to release 2-PMPA efficiently (FIGS. 8B, 9A-9B; Tables 5-7). An in vivo single time point pharmacokinetic study (method 1) of compounds JHU 2106-2112 in mice suggested that the POM (JHU 2109) and POC (JHU 2110) prodrugs were the most permeable (FIG. 10). A more than 50-fold increase of the POM and POC ester prodrugs/metabolites was seen following oral dosing (method 1; FIG. 7). However, the POM and POC ester prodrugs did not release 2-PMPA (method 2; FIG. 8). Increasing the ester chain length on the carboxylates did not increase 2-PMPA release (FIGS. 9A-9B, Tables 8-9). No or minimal 2-PMPA release was observed with the ethyl and propyl esters. Compounds 2236 and 2237, ethyl and alkyl ester derivatives, were found to be too stable and not much release of 2-PMPA was observed (Tables 8-9).

However, the stability of the simple carboxylic ester could be overcome by introducing another isopropyloxycarbonyloxy methyl or pivaloyloxy methyl moiety on the α-carboxylate. The Tris-POC (JAM0186) and Tris-POM (JAM0168) prodrugs demonstrated sufficient chemical stability, especially the POC moiety, and instability in plasma and liver subcellular fractions depicting the potential of releasing 2-PMPA (FIGS. 10A-10B; scheme for synthesis of Tris-POC shown in FIG. 1). Without wishing to be bound to any one particular theory, it is believed that the double esters on the Tris-POC prodrug allow better release of the prodrug to 2-PMPA. The POM esters on the carboxylate increased 2-PMPA approximately 18-fold following oral dosing. In vivo pharmacokinetic studies at 30 mg/kg equivalent 2-PMPA in mice showed about a 20-fold increase in the 2-PMPA availability (FIG. 10B). This is the first time high micromolar concentrations of 2-PMPA have been achieved in plasma following oral administration.

In addition, compound 2609, with an extra methyl group, also demonstrated sufficient chemical stability, and instability in plasma and liver subcellular fractions (Table 10).

In terms of permeability of the esters on the α-carboxylate, the ethyl ester (compound JHU 2236) showed the most permeability, followed by the methyl ester (compound JHU 2106), and then the propyl ester (compound JHU 2263). Even so, compounds with simple alkyl esters on the α-carboxylate, though they showed some enhancement in permeability, were too stable to cause the release of 2-PMPA in vivo. In addition, both the mono and diesters showed comparable permeabilities and not much difference was observed between the mono ethyl and mono methyl esters. Except for the POM and POC esters on phosphonates (compounds JAM0168 and JAM0186), most of the other functionalities did not show a high permeability in vivo (e.g., compounds JHU 2235 and 2238). The POM and POC esters on phosphonate showed the highest permeability and were chosen as appropriate promoeities for phosphonic acid and further structural modification were based on these for enhancement of 2-PMPA permeability and release.

TABLE 2

Stability results for JHU 2106 in different matrices.

| Time (min) | HBSS | Mouse Plasma | Mouse S9 | Mouse Microsomes | Human Plasma | Human Microsomes |
|---|---|---|---|---|---|---|
| 0 | 100% | 100% | 100% | 100% | 100% | 100% |
| 30 | 92% | 102% | 101% | 102% | 100% | 90% |
| 60 | 94% | 101% | 86% | 103% | 86% | 96% |

TABLE 3

Stability results for JHU 2108 in different matrices.

| Time (min) | HBSS | Mouse Plasma | Mouse S9 | Mouse Microsomes |
|---|---|---|---|---|
| 0 | 100% | 100% | 100% | 100% |
| 30 | 99% | 2% | 106% | 99% |
| 60 | 101% | 1% | 100% | 100% |

TABLE 4

Stability results for JHU 2109 in different matrices.

| Time (min) | HBSS | Mouse Plasma | Mouse S9 | Mouse Microsomes |
|---|---|---|---|---|
| 0 | 100% | 100% | 100% | 100% |
| 30 | 46% | 0% | 1% | 2% |
| 60 | 21% | 0% | 0% | 0% |

TABLE 5

Stability results for JHU 2110 in different matrices.

| Time (min) | HBSS | Mouse Plasma | Mouse S9 | Mouse Microsomes |
|---|---|---|---|---|
| 0 | 100% | 100% | 100% | 100% |
| 30 | 101% | 2% | 1% | 2% |
| 60 | 93% | 0.4% | 0.1% | 0.1% |

TABLE 6

Stability results for JHU 2111 in different matrices.

| Time (min) | HBSS | Mouse Plasma | Mouse S9 | Mouse Microsomes |
|---|---|---|---|---|
| 0 | 100% | 100% | 100% | 100% |
| 30 | 100% | 3% | 1% | 3% |
| 60 | 95% | 1% | 2% | 2% |

TABLE 7

Stability results for JHU 2112 in different matrices.

| Time (min) | HBSS | Mouse Plasma | Mouse S9 | Mouse Microsomes |
|---|---|---|---|---|
| 0 | 100% | 100% | 100% | 100% |
| 30 | 93% | 2% | 0% | 2% |
| 60 | 93% | 1% | 0.1% | 0.1% |

TABLE 8

Stability results for JHU 2236 in different matrices.

| Time (min) | Mouse Microsomes | Mouse Plasma | Mouse S9 | Human Microsomes | Human plasma |
|---|---|---|---|---|---|
| 0 | 100% | 100% | 100% | 100% | 100% |
| 30 | 99% | 99% | 103% | 88% | 81% |
| 60 | 88% | 83% | 103% | 73% | 59% |

TABLE 9

Stability results for JHU 2237 in different matrices.

| Time (min) | Mouse Microsomes | Mouse Plasma | Mouse S9 | Human Microsomes | Human plasma |
|---|---|---|---|---|---|
| 0 | 100% | 0% | 100% | 100% | 100% |
| 30 | 2% | 0% | 1% | 1% | 50% |
| 60 | 0% | 0% | 0% | 0% | 18% |

TABLE 10

Stability results for JHU 2608, 2609 and 2610 in different species

| JHU# | Time (min) | Human Microsomes | Human Plasma | Mouse Microsomes | Mouse Plasma |
|---|---|---|---|---|---|
| JHU 2608 | 0 | 100% | 100% | 100% | 100% |
| | 30 | 80% | 109% | 49% | 0% |
| | 60 | 61% | 76% | 22% | 0% |
| JHU 2609 | 0 | 100% | 100% | 100% | 100% |
| | 30 | 27% | 106% | 1% | 0% |
| | 60 | 8% | 75% | 0% | 0% |
| JHU 2610 | 0 | 100% | 100% | 100% | 100% |
| | 30 | 92% | 98% | 86% | 3% |
| | 60 | 81% | 92% | 68% | 1% |

Example 12

2-PMPA Prodrugs with Tris POC Esters in Different Species

The 2-PMPA prodrugs with the Tris-POC esters showed excellent oral bioavailability in rodents and dogs (compound JHU 2609, Table 10; compound JAM0186, FIGS. 11-14, Table 11). The Tris-POC compound enhanced exposures following oral dosing in mice and achieved more than 20-fold enhancement in permeability versus 2-PMPA (FIG. 12). The metabolic stability of the Tris-POC compound in different species was seen, with the dog stability most similar to the human stability (FIG. 13). Relative to the mouse, the dog sample showed a 10 fold increase in the $C_{max}$ of 2-PMPA, showing a high availability of the compound in the dog species (FIG. 14). The metabolic stability of the Tris-POC compound could be further enhanced in different species by the addition of a methyl group (FIG. 15).

TABLE 11

Stability results for TRIS-POC in different species

| Time (min) | Human Microsomes | Human Plasma | Mouse Microsomes | Mouse Plasma |
|---|---|---|---|---|
| 0 | 100% | 100% | 100% | 100% |
| 30 | 3% | 64% | 1% | 1% |
| 60 | 0% | 48% | 0% | 0% |

| Time (min) | Human Microsomes | Human Plasma | Dog Microsomes | Dog Plasma | Monkey Microsomes | Monkey Plasma |
|---|---|---|---|---|---|---|
| 0 | 100% | 100% | 100% | 100% | 100% | 100% |
| 30 | 5% | 102% | 1% | 67% | 0% | 50% |
| 60 | 0% | 77% | 0% | 28% | 0% | 11% |

Example 13

Pharmacological Inhibition of PSMA as IBD Therapy

An Overview of IBD: IBD, an idiopathic, chronic and frequently disabling inflammatory disorder of the intestine, has two subtypes: Crohn's disease (CD) and ulcerative colitis (UC), each accounting for ~50% of IBD patients (Xavier and Podolsky, 2007; Strober et al., 2007; Sartor, 2006). IBD is a widespread GI disease, with a prevalence of ~0.2% in Western population. In the United States alone, there are 1.4 million diagnosed IBD patients, resulting in enormous suffering and health-care costs. It is increasingly clear that IBD is a complex multifactorial disease with both genetic and environmental contributions, the interaction of which leads to IBD (Xavier and Podolsky, 2007; Strober et al., 2007; Sartor, 2006; Kaser et al., 2010). Unfortunately, the etiology of this mucosal dysregulation in UC and CD remain elusive (Kaser et al., 2010). Despite increasing therapeutic options available for the management of IBD, approximately ⅓ of IBD patients do not respond to any given therapy, and there is no cure for IBD (Hamilton et al., 2012). Anti-tumor necrosis factor (TNF)-based therapies, such as infliximab (IFX), adalimumab and certolizumab pegol are currently the most effective therapies for severe UC and CD (Hanauer et al., 2002; Kozuch and Hanauer, 2008; Colombel et al., 2007; Schreiber et al., 2007). However, one-third of patients with CD do not respond to anti-TNF therapies and another third lose responsiveness within six months of initiating therapy (Regueiro et al., 2007; Lawrance, 2014). These nonresponders have more aggressive mucosal immune responses and additional treatments are indicated (Schmidt et al., 2007). Patients with extensive disease or who are at risk for short gut syndrome due to prior resections are usually poor surgical candidates. Currently, the only approved medication for patients who have failed an anti-TNF agent is natalizumab. However, natalizumab has been associated with several cases of progressive and often fatal multifocal leukoencephalopathy (PML; Van et al., 2005). This emphasizes the significance of exploring and identifying new and more effective therapies in patients with IBD.

Human Validation Data: PSMA expression and enzymatic activity is selectively elevated in patient samples with IBD (FIGS. 16-17). Gene-profiling and immunohistological analyses (FIG. 16) showed that PSMA is intensely upregulated in the intestinal mucosa of patients with Crohn's disease (Zhang et al., 2012). To further determine the relevance of PSMA to IBD, PSMA functional enzymatic activity was examined and compared in normal and diseased mucosa of 32 surgical intestinal specimens from 20 subjects (FIG. 17), including healthy controls, patients with IBD, and non-IBD controls (diverticulitis), using previously described methods. A 300-1,000% increase in PSMA activity was found in the intestinal mucosa with active IBD when compared to that in an uninvolved area of the same patients, or the intestine from healthy and non-IBD controls. These data suggest a clear positive association between activation of PSMA and IBD.

Figure 21A:
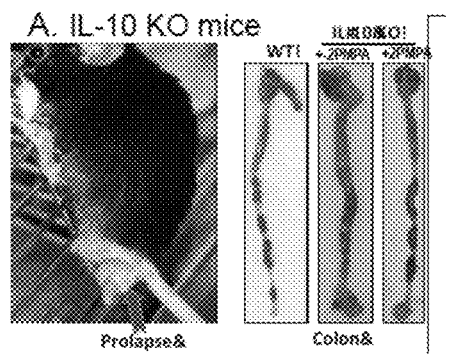
Figure 21B:
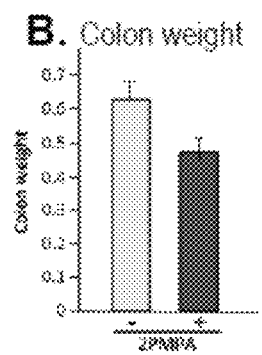
Figure 21C:
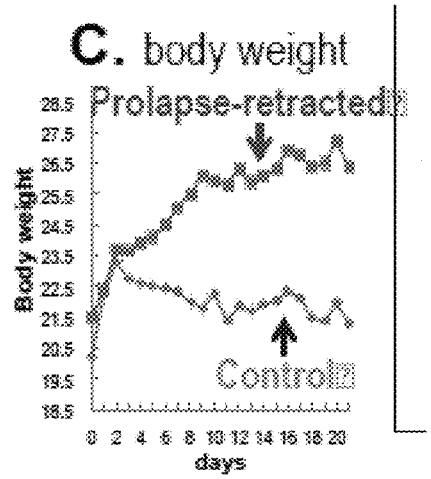
Figure 21D:
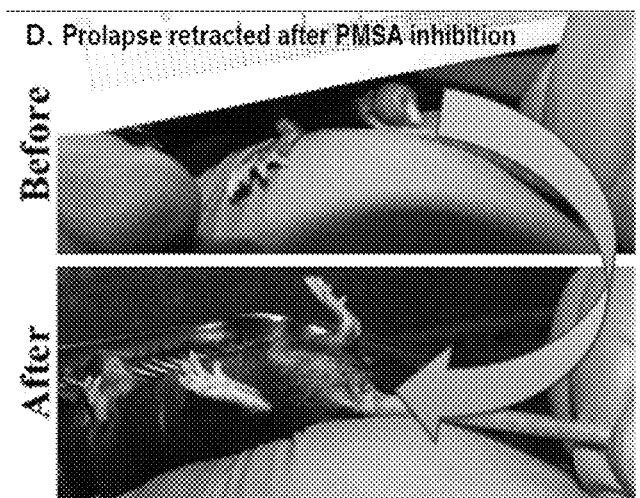

Preclinical Efficacy: PSMA inhibition shows profound efficacy in three major animal models of IBD (FIGS. 18-21). To investigate whether PSMA can be a suitable novel therapeutic target for clinical intervention against IBD, the effect of PSMA prototype inhibitors on three most widely used murine models of IBD was tested, including DNBS-induced colitis, DSS-induced colitis, and IL-10 knockout (IL-10 KO) mice (a genetic model that develops spontaneous colitis). In all three models, PSMA inhibitor treatment dramatically ameliorated symptoms. In the DNBS-induced colitis model (FIG. 18), PSMA inhibition was found to be similar to positive control sulfasalazine. In the DSS colitis model, PSMA inhibition significantly reduced the disease activity index (FIG. 19). Moreover, the PSMA activity in the colonic and cecal mucosa of DSS-treated mice was potently inhibited by PSMA inhibitor, indicating target engagement (FIG. 20). The efficacy of 2-PMPA in treatment of spontaneous colitis in IL-10 KO mice was also remarkable. First, PSMA inhibitor 2-PMPA significantly reduced the disease severity, including macroscopic disease, colonic hypotrophy, and provided better stool consistency (FIGS. 21A-21B). More interestingly, a complete retraction of prolapse in 2 of the 20 mice (10%) treated with the inhibitor was observed (FIG. 21D), a phenomenon that has never been seen in more than 800 IL-10 KO mice used. The improvement of these prolapse-retracting mice was unequivocally obvious in that their body weight increased dramatically when compared to that of untreated control IL-10 KO mice (FIG. 21C). In conclusion, using three major animal models of IBD, the significance of PSMA as a novel therapeutic target for treatment of IBD has been demonstrated.

Novel orally available prodrug of 2-PMPA has been identified that exhibits >20 fold enhancement in 2-PMPA permeability in vivo: The very potent phosphonic acid-based PSMA inhibitor termed 2-PMPA (Ki=300 μM) (Rais et al., 2014) demonstrated excellent efficacy following i.p. administration at 100 mg/kg in both the DSS as well as IL 10 knock out model. However, 2-PMPA is extremely hydrophilic with poor oral availability (F<1%). Given the success of using prodrug approaches to increase the oral bioavailability of other phosphonic acid drugs (Hepsera™ and Viread™) (Barditch-Crovo et al., 1997; Cundy et al., 1997; Barditch-Crovo et al., 2001), a similar strategy for 2-PMPA was employed. An orally bioavailable prodrug of 2-PMPA (Tris-POC-2-PMPA) has been identified that enables ~20 fold enhancement in permeability (FIG. 17). More importantly, the prodrug afforded >10-20 fold sustained concentrations of liberated 2-PMPA for up to 4 hours following oral administration.

Dose Response/Efficacy and Pharmacokinetic Studies of PSMA Inhibitors (2-PMPA and its Oral Prodrug) in Two Murine Models of IBD: IL-10 Knockout (KO) and DSS-Induced Colitis:

The dose response of 2-PMPA (HEPES saline as vehicle) with three doses, 1, 10, and 100 mg/kg, using an i.p. delivery route, has been completed and it was observed that a dose dependent effect with 100 mg/kg provided the most benefit. The 2-PMPA Tris POC prodrug has also been tested in a preliminary experiment at one high dose via the oral route (100 mg/kg) using a 50% PEG/water vehicle. Unfortunately, the vehicle itself showed detrimental effects. Several FDA approved vehicles will be evaluated including ethanol/tween, propylene glycol and 2-Hydroxypropyl-beta-cyclodextrin (HP-beta-CD) for solubility and compatibility (Thackaberry, 2013). Once the optimal vehicle is identified, a dose response of the oral 2-PMPA Tris POC prodrug delivered at 3, 10, and 30 mg/kg p.o. (equivalent 2-PMPA) will be completed. To evaluate efficacy, for DSS model of colitis, the prodrug will be evaluated orally at three different doses mentioned above at the same time (day 1) as DSS is given to induce colitis. The treatment duration will be 7 days, as described in FIG. 23. For IL-10 KO model of colitis, 3 month old mice will be given the prodrug and treatment duration will be 2 weeks, as described in FIG. 26.

For the pharmacokinetic studies, at the end of treatment on day 7 (DSS model) and day 14 (IL-10 KO model) at 2 hour post dose, blood and colonic mucosa will be collected for drug PK analysis. Plasma will be generated from blood by centrifugation and all samples will be stored at −80° C. until further analysis. Concentrations of inhibitors in plasma and tissue will be determined via LC/MS/MS as described previously (Rais et al., 2014).

Determine the cellular and molecular mechanisms of PSMA inhibition in IBD including effects on intestinal epithelial cells, dendritic cells (DCs), and intestinal mucosal cytokine profiles: Involvement of PSMA in the pathogenesis of IBD is novel and little is known. Explanation of this association is beyond the current knowledge on PSMA. Therefore, it is important to understand how PSMA is involved in IBD at the cellular and/or molecular levels.

The major site of PSMA expression in the intestine is the mucosa (FIGS. 21 and 22), where immunohistological analysis shows PSMA is predominantly expressed in the intestinal epithelial cells (FIG. 21). Therefore, to determine if the PSMA inhibitors target directly to the intestinal epithelial cells, the first logical site of drug action would be the intestinal epithelial cells. The hypothesis is that in the state of IBD, intestinal epithelial cells, which are the first defense line in the gut to keep the commensal and invading bacteria at bay, may sense a change in luminal bacteria and respond with a surge of PSMA expression. This increase of PSMA activity would then promote subsequent secretion of proinflammatory factors such as cytokines, and trigger an inflammatory cascade that leads to IBD. To test this hypothesis, colonic epithelial cells (CECs), both Caco-2 cells (a widely used colonic epithelial cell line) and CECs isolated from mice (WT, control and IL-10KO), will be used, as schematically illustrated in FIG. 27. For normal CECs or Caco-2 cells, inflammatory conditions will be induced by 10 nm LPS during cell culture (LPS will activate the proinflammatory cascade through TLR4 that are highly expressed on CECs). CECs isolated from IL-10KO mice (3-month old) will be inflamed, and thus there is no need for induction with LPS. Cytokine levels in culture medium (secreted) will be analyzed by multiplex ELISA (using BIORAD Bio-Plex 200 System with HTF and automated washer), as previously described (Alex et al., 2009; Alex et al., 2010) for 17 different cytokines and chemokines, and those in the cells will be analyzed by RT-PCR. The cytokines/chemokines to be analyzed include IL-1α, IL-1β, IL-2, IL-4, IL-6, IL-10, IL-12 (p40), IL-13, IL-17, IFN (Interferon)-γ, TNFα, G-CSF, CCL2 (MCP-1), CCL3 (MIP-1α), CCL4 (MIP-1β), CXCL8 (IL-8), and CXCL10 (IP-10). It will be determined if LPS treatment activates the gene expression of PSMA by directly measuring PSMA activity. If PSMA inhibitors suppress the expression and secretion of proinflammatory cytokines and/or enhance the expression and secretion of anti-inflammatory cytokines (such as IL-10 and/or IL-22), it would suggest that increased PSMA expression promotes inflammation in CECs, and thereby confirms the hypothesis that the PSMA inhibitors indeed target directly to the CECs.

Another target for PSMA inhibitors might be the highly specialized dendritic cells (DCs). IBD has been considered as a T-cell-driven inflammatory disease, by highly specialized immune cells called dendritic cells (DCs). DCs determine whether T-cell responses are immunogenic (against harmful invading pathogens) or tolerogenic (against harmless antigens). In the gut, intestinal DCs recognize and respond to bacteria from the gut lumen and maintain intestinal immune homeostasis by generating tolerogenic T-cell responses towards the commensal microbiota. Previous efforts have recently demonstrated a specific DC subset, CD103+DCs, which can be successfully identified in the human colon. The proportion of CD103+DCs was reduced in patients with active IBD (FIG. 28). Recent reports in mice demonstrate intestinal DCs expressing the gut-homing marker $\alpha_4\beta_7$ are required for induction of T-reg and IL-10-producing T-cells (Villablanca et al., 2013). There is strong evidence that expression of $\alpha_4\beta_7$ on murine colonic DCs is confined to the CD103+ subset. Furthermore, proportions of $\alpha_4\beta_7$+DCs are reduced in the inflamed colon of IL-10KO mice (FIG. 29), suggesting IL-10 may play a key role in differentiation of $\alpha_4\beta_7$+ regulatory DC subsets in the gut. This subset of DCs plays a critical role of dampening the T-cell response in normal condition and is lost in the inflammatory condition in both human and murine model of colitis.

Without wishing to be bound to any one particular theory, it is thought that a PSMA inhibitor may up-regulate this particular tolerogenic DC subset, thereby reducing the T-cell-mediated inflammatory response and ameliorate symptoms of colitis in IL-10 KO mice as was observed (FIG. 26). Although PSMA is not normally expressed in the DCs, it is possible that it is expressed in these cells when under inflammatory conditions, and that PSMA expression may suppress the expansion of this specific subset of DCs. Alternatively, it is also possible that the upregulation of PSMA in CECs activates and releases certain cellular factors that inhibit the colonic DC expansion, resulting in the loss of this tolerogenic DCs and leading to a hyper-reactive T-cell response. To test this hypothesis, it will first be determined whether PSMA is upregulated in DCs in the inflammatory condition. The best model for this purpose is the IL-10KO mice, since previous efforts have already demonstrated the therapeutic efficacy of PSMA inhibitors and the loss of the colonic tolerogenic CD103+/$\alpha_4\beta_7$+DC subset in IL-10KO mice. At least one of the following two approaches can be employed: 1) RT-PCR: DCs can be isolated by FACS from colonic mucosa of both WT (control) and IL-10KO mice. PSMA expression can be analyzed by RT-PCR; 2) Immunohistology: Colonic segments of both WT (control) and IL-10KO mice can be examined for the expression of PSMA in DCs using CD103 and $\alpha_4\beta_7$ as marker for DCs (triple labeling).

To determine if PSMA inhibitors promote tolerogenic CD103+/$\alpha_4\beta_7$+DC subset, colonic DCs can be isolated from IL-10 KO mice that are treated or not (control) with 2-PMPA or its prodrug, and further analyzed for CD103+/$\alpha_4\beta_7$+ by FACS, as demonstrated in FIGS. 28-29. If the hypothesis is correct, it is expected that an increase or recovery of the tolerogenic CD103+/$\alpha_4\beta_7$+DC subset toward what occurs in WT mice (see FIG. 29) in the colon of diseased IL-10KO mice will be seen.

In terms of cytokine profiling in the colonic mucosa, it is hypothesized that inhibition of PSMA in general may suppress the proinflammatory cytokines/chemokine and/or enhance anti-inflammatory ones in the colon. To test this hypothesis, total colonic mucosa can be isolated from colitis mice that are treated or not (controls), and a set of 17 cytokines/chemokines (see the list above) in the total mucosal protein extract can be analyzed by multiplex ELISA.

Summary: Recent genomic, clinical, and pharmacological data implicate the metalloenzyme Prostate Specific Membrane Antigen (PSMA), in the etiology of inflammatory bowel disease (IBD). Data illustrate that pharmacological inhibition of PSMA using prototype inhibitors ameliorates IBD symptoms in three preclinical models. Orally available inhibitors have recently been synthesized and characterized.

Given these strong findings, it is hypothesized that PSMA activates a proinflammatory signaling cascade that leads to or enhances intestinal inflammation in IBD, and that specific pharmacological inhibition will be a novel and effective strategy for IBD therapy.

Example 14 (Prophetic)

Pharmacological Inhibition of PSMA as MS Therapy

Introduction: Approximately 50% of 2.3 million Multiple Sclerosis (MS) patients worldwide experience cognitive impairment, for which there is no approved treatment (Dutta and Trapp. Neurology, 2007. 68 (22 Suppl 3): p. S22-31; Calabrese, et al. Arch Neurol, 2009. 66 (9): p. 1144-50), making therapies in MS cognition a large unmet medical need. N-acetylaspartylglutamate (NAAG), one of the most abundant neuropeptides in the mammalian brain (Neale, et al. J Neurochem, 2000. 75 (2): p. 443-52), is thought to serve as the endogenous agonist of the metabotropic glutamate receptor 3 (mGluR3) (Olszewski, et al. Schizophr Res, 2012. 136 (1-3): p. 160-1). Recent clinical data collected in MS patients at Johns Hopkins University revealed a significant positive correlation between hippocampal NAAG concentration and patients' performances on a battery of cognitive tasks (Rahn, et al. Proc Natl Acad Sci USA, 2012. 109 (49): p. 20101-6). Notably, MS patients with low hippocampal NAAG levels showed cognitive impairment while patients with higher levels of hippocampal NAAG exhibited normal cognition. In support, polymorphisms of mGluR3 have recently been linked to differential cognitive abilities (Jablensky, et al. Genes Brain Behav, 2011. 10 (4): p. 410-7; Egan, et al. Proc Natl Acad Sci USA, 2004. 101 (34): p. 12604-9; 8 Harrison, et al. J Psychopharmacol, 2008. 22 (3): p. 308-22; Sartorius, et al. Neuropsychopharmacology, 2008. 33 (11): p. 2626-34).

The brain metallopeptidase Glutamate Carboxypeptidase II (GCPII) catabolizes NAAG in vivo. One of the most potent ($IC_{50}$=300 pM) and selective GCPII inhibitors, termed 2-PMPA, has been shown to significantly increase brain NAAG levels and improve cognition in preclinical models (Olszewski, et al., Transl Psychiatry, 2012. 2: p. e145; Yamada, et al. Mol Pain, 2012. 8: p. 67; Janczura, et al., Eur J Pharmacol, 2013. 701 (1-3): p. 27-32; Gurkoff, et al. Brain Res, 2013. 1515: p. 98-107) including MS (Rahn, et al. Proc Natl Acad Sci USA, 2012. 109 (49): p. 20101-6). To our knowledge, 2-PMPA is the first and only treatment strategy that has been shown to attenuate cognitive impairment in a preclinical model of MS. However, 2-PMPA is a polar bisphosphonate-based compound which is active only after systemic dosing (i.p. or i.v.). It has negligible oral bioavailability and is therefore unsuitable for daily chronic dosing in patients. Using prodrug strategies proven successful in enhancing the oral bioavailability of other bisphosphonate compounds which are now marketed and widely used (ADEFOVIR™ and TENOFOVIR™) (Cundy, et al. J Pharm Sci, 1997. 86 (12): p. 1334-8; Deeks, et al., J Infect Dis, 1997. 176 (6): p. 1517-23; Kearney, et al. Clin Pharmacokinet, 2004. 43 (9): p. 595-612), novel orally bioavailable prodrugs of 2-PMPA can be synthesized. The presently disclosed subject matter provides one such prodrug, with >100-fold increase in bioavailability in dogs, respectively clearly demonstrating feasibility of the approach. Employing an iterative medicinal chemistry and drug metabolism/pharmacokinetic approach, it is proposed to systematically optimize novel prodrugs with the goal of developing an, ultimately, clinical investigation in MS patients.

Prodrugs will be evaluated in an experimental autoimmune encephalomyelitis (EAE) mouse model of multiple sclerosis. Mice will be immunized and receive daily p.o. dosing of either vehicle or 2-PMPA prodrug from the time of immunization until sacrifice (prevention paradigm) or will be treated either with vehicle or 2-PMPA prodrug (treatment paradigm). The development and progression of the resulting deficits will be tracked by EAE disease scores, body weight measurements, and cognitive testing. Postmortem analysis of brain NAAG, 2-PMPA and GCPII inhibition confirming target engagement will be performed in tandem.

NAAG is an mGluR3 agonist which is inactivated by GCPII: N-acetyl aspartyl glutamate (NAAG), one of the most abundant neuropeptides in the mammalian central nervous system (CNS) (Neale, et al. J Neurochem, 2000. 75 (2): p. 443-52), is a selective agonist at metabotropic glutamate receptor 3 (mGluR3) (Olszewski, et al. Schizophr Res, 2012. 136 (1-3): p. 160-1). As with other neurotransmitter/modulators, the concentration of extracellular NAAG is tightly regulated. A 94kD class II membrane bound zinc metalloenzyme termed glutamate carboxypeptidase II (GCPII, also called NAALADase or NAAG peptidase) degrades into N-acetylaspartate (NAA) and glutamate (FIG. 26).

Decreased brain NAAG associated with cognitive impairment: Human studies spanning two decades report that CNS NAAG concentrations are altered in neurological diseases with comorbid cognitive impairment (Jaarsma, et al. J Neurol Sci, 1994. 127 (2): p. 230-3; Rowland, et al., *GABA, and NAAG in schizophrenia*. Schizophr Bull, 2013. 39 (5): p. 1096-104; Tsai, et al., *CNS*. Brain Res, 1991. 556 (1): p.

151-6), including MS (Rahn, et al. Proc Natl Acad Sci USA, 2012. 109 (49): p. 20101-6). Historically post-mortem immunohistochemical or HPLC/MS techniques were required for quantitation of brain NAAG levels, however with the recent development of advanced neuroimaging techniques and increased MRI magnet strength ($\geq$3T), in vivo imaging of NAAG is now possible. Recent clinical data collected at the Johns Hopkins hospital demonstrate a significant and selective positive correlation between hippocampal NAAG concentration in MS patients and their performance on a battery of cognitive tasks (Rahn, et al. Proc Natl Acad Sci USA, 2012. 109 (49): p. 20101-6). Specifically, MS patients with cognitive impairment have low hippocampal NAAG levels while MS patients with normal cognition have higher levels of hippocampal NAAG (FIG. 27).

No clinically available GCPII inhibitor to date: Unfortunately, to date no GCPII inhibitor has high potential for clinical translation. Eisai, Inc (formerly Guilford Pharmaceuticals) developed an orally bioavailable, thiol-based GCPII inhibitor which completed 2 Phase 1 studies. Although the inhibitor was well-tolerated in Phase 1 (REF) subsequent immunological toxicities observed in GLP primate studies halted its development. Importantly the toxicity was not due to the GCPII mechanism, but rather due to the thiol moiety in the compound. As a class, thiol drugs have a risk of inducing hypersensitivity reactions (REF). Given the large unmet medical need for, second generation non-thiol GCPII inhibitors devoid of this immunological risk for advancement into clinical development can be synthesized. Beyond thiol inhibitors, the most potent, selective, and efficacy inhibitors of GCPII described are phosphonic acid based, however they have minimal orally bioavailability.

2-PMPA increases brain NAAG and prevents cognitive deficits in a mouse model: The metabolite NAAG is broken down by the enzyme GCPII. Without wishing to be bound to any one particular theory, it is thought that administration of 2-phosponomethyl pentanedioic acid (2-PMPA), a potent and selective inhibitor of GCPII, would reverse cognitive impairment in an animal model of MS with known learning and memory deficits (Ziehn, et al. EAE. Lab Invest, 2010. 90 (5): p. 774-86). Mice (n=10) were immunized for EAE, injections of 2-PMPA were administered daily from the time of disease induction, and behavior tests were conducted after chronic physical signs of disease were established. While no difference in physical severity was observed, cognition was significantly improved in mice treated with the GCPII inhibitor (EAE+2-PMPA) compared to vehicle-treated controls (EAE+Vehicle) as measured by Barnes maze (a circular land maze analogous to the Morris water maze that is used for animals with physical disabilities) and fear conditioning tests (Rahn, et al. Proc Natl Acad Sci USA, 2012. 109 (49): p. 20101-6). EAE+Vehicle mice had higher Barnes maze path efficiency delta and significantly decreased total latency delta as compared to Control+Vehicle ($P<0.05$), indicating cognitive impairment. Conversely, the total latency and path efficiency of EAE+2-PMPA mice did not differ from Control+Vehicle mice. Furthermore, EAE+2-PMPA mice had significantly improved (i.e. over 2-fold) path efficiency and total latency as compared to EAE+Vehicle mice (FIG. 28A and FIG. 28B, $P<0.01$ and $P<0.05$, respectively). Fear conditioning tests demonstrated a significant difference between fear memory in EAE+2-PMPA mice compared to EAE+Vehicle mice ($P<0.05$). Post mortem analysis demonstrated a significant increase in brain NAAG in EAE+2-PMPA mice versus EAE+Vehicle mice (FIG. 28C, $P<0.05$). Taken together, these data demonstrate that GCPII inhibition restores the cognitive and biological deficits resulting from EAE.

Conduct prodrug efficacy studies in a mouse model of multiple sclerosis: Prodrugs of 2-PMPA will be tested for in vivo efficacy. Preclinical studies will be conducted using the research design in which daily intraperitoneal injection of the GCPII inhibitor 2-PMPA demonstrated significant beneficial effects on cognitive function (Rahn, et al. Proc Natl Acad Sci USA, 2012. 109 (49): p. 20101-6). Mice will be immunized for chronic EAE as previously described (Rahn, et al. Proc Natl Acad Sci USA, 2012. 109 (49): p. 20101-6), and daily oral dosing of prodrug or vehicle will begin from the time of immunization and continue until sacrifice. Control groups not immunized for EAE will be included in to determine if daily 2-PMPA prodrug administration improves learning and memory in healthy non-EAE control mice. An EAE+2-PMPA i.p. control group will be included to determine if oral prodrug treatment is more or less efficacious versus daily intraperitoneal injections 2-PMPA. Animals will be divided into five groups (n=15/group):

Group 1=Control+Vehicle
Group 2=Control+2-PMPA Prodrug
Group 3=EAE+Vehicle
Group 4=EAE+2-PMPA Prodrug
Group 5=EAE+2-PMPA (i.p.)

Mice will be monitored daily for signs of EAE. Approximately two weeks after disease onset, mice will be subjected to elevated plus maze testing, followed by Barnes maze testing, then fear conditioning. Upon completion of the tests (approximately Day 50), animals will be sacrificed and brains will be dissected. NAA, NAAG and 2-PMPA levels will be measured in the hippocampus, cerebellum, and frontal lobe via mass spectrometry. To measure prodrug bioavailability and the effects of GCPII inhibition on brain NAAG, five satellite animals will be sacrificed prior to behavior testing (approximately 4 weeks post-immunization). The remaining 10 animals will be sacrificed following the completion of all behavioral tests. The above tests will be conducted for 2-PMPA prodrugs.

Expected Results: The GCPII inhibitor prodrug is thought to be equally efficacious at preventing cognitive impairment in EAE as compared to daily intraperitoneal injections of 2-PMPA. EAE mice treated with the 2-PMPA prodrug are expected to perform as well as Control (i.e. non-EAE) mice on Barnes maze and fear conditioning tests. Elevated plus maze performance, a measure of anxiety, is not expected to differ between EAE and Control cohorts. It is expected that the prodrug treatment will restore brain NAAG levels equivalent to those observed in Control mice (Rahn, et al. Proc Natl Acad Sci USA, 2012. 109 (49): p. 20101-6). Previous work from our laboratory and others has demonstrated that GCPII inhibition has no effect on cognitive function in Control mice. Therefore, Groups 1 and 2 are not expected to differ with regard to cognitive function. It is possible, however, that the improved bioavailability of the prodrug will cause cognitive enhancing effects in normal mice.

Summary: Despite the fact that over 200,000 MS patients suffer from some type of cognitive impairment in the United States alone, no therapies have been developed to treat MS-associated learning and memory deficits. The failure of clinical trials designed to translate pre-existing therapies for other neurological diseases with comorbid cognitive impairment, such as memantine, rivastigmine, and donepezil in Alzheimer's disease, to treatments for cognitive impairment in MS suggest that alternative and specific treatment pathways should be explored. To our knowledge the present approach is the first to develop a drug treatment that selectively targets an established biological deficit in cognitively impaired MS patients (i.e. the reduction in brain NAAG). Thus, completion of the presently disclosed studies could lead to the first treatment specifically developed to treat cognitive impairment in MS. NMSS thought that our NAAG/GCPII efficacy data were sufficiently important to fund mechanistic research (PI: Dr. Adam Kaplin) into the action of 2-PMPA utilizing GCPII and mGluR3 KO mice, and pharmacological receptor antagonists. While related to Dr. Kaplin's project, this independent project is a logical and translationally-focused continuation of the funded work, as 2-PMPA is not an effective long-term treatment strategy in humans. The presently disclosed studies are required to develop a compound that is safe and effective for human use.

In addition to a novel treatment for cognitive impairment, these studies may also lead to the development of a human biomarker with clinical and treatment applications. Recent advances in magnetic resonance spectroscopy allow for the quantitation of CNS NAAG levels in humans using 3T or 7T MRI scanners. NAAG, therefore, can be used as a disease biomarker to measure changes in NAAG levels in MS patients over time, identify the ~1 million patients who would benefit from our treatment strategy, and monitor drug effects over time or may be susceptible to cognitive impairment.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Although the foregoing subject matter has been described in some detail by way of illustration and example for purposes of clarity of understanding, it will be understood by those skilled in the art that certain changes and modifications can be practiced within the scope of the appended claims.

Alex, P.; Zachos, N. C.; Nguyen, T.; Gonzales, L.; Chen, T. E.; Conklin, L. S.; Centola, M.; Li, X. Distinct cytokine patterns identified from multiplex profiles of murine DSS and TNBS-induced colitis. *Inflamm. Bowel Dis.* 2009, 15:341-352.

Alex, P.; Ye, M.; Zachos, N. Z.; Sipes, J.; Nguyen, T.; Suhodrev, M.; Gonzales, L.; Arora, Z.; Zhang, T.; Centola, M.; Guggino, SE.; Li, X. Clc-5 Knockout mice exhibit novel immunomodulatory effects and are more susceptible to dextran sulphate sodium induced colitis. *J. Immunol.* 2010, 184:3988-3996.

Barditch-Crovo, P.; Deeks, S. G.; Collier, A.; Safrin, S.; Coakley, D. F.; Miller, M.; Kearney, B. P.; Coleman, R. L.; Limy, PAD.; Kahn, J. O.; McGowan, I.; Lietman, P. S. Phase i/ii trial of the pharmacokinetics, safety, and antiretroviral activity of tenofovir disoproxil fumarate in human immunodeficiency virus-infected adults. *Antimicrob. Agents Chemother.* 2001, 45:2733-2739.

Barditch-Crovo, P.; Toole, J.; Hendrix, C. W.; Cundy, K. C.; Ebeling, D.; Jaffe, H. S.; Lietman, P. S. Anti-human immunodeficiency virus (HIV) activity, safety, and pharmacokinetics of adefovir dipivoxil (9-[2-(bis-pivaloyloxymethyl)-phosphonylmethoxyethyl]adenine) in HIV-infected patients. *J. Infect. Dis.* 1997, 176:406-413.

Colombel, J. F.; Sandborn, W. J.; Rutgeerts, P.; Enns, R.; Hanauer, S. B.; Panaccione, R.; Schreiber, S.; Byczkowski, D.; Li, J.; Kent, J. D.; Pollack, P. F., Adalimumab for maintenance of clinical response and remission in patients with Crohn's disease: the CHARM trial. *Gastroenterology* 2007, 132:52-65.

Cundy, K. C.; Sue, I. L.; Visor, G. C.; Marshburn, J.; Nakamura, C.; Lee, W. A.; Shaw, J. P. Oral formulations of adefovir dipivoxil: in vitro dissolution and in vivo bioavailability in dogs. *J. Pharm. Sci.* 1997, 86:1334-1338.

Hamilton, M. J.; Snapper, S. B.; Blumberg, R. S., Update on biologic pathways in inflammatory bowel disease and their therapeutic relevance. *J. Gastroenterol.* 2012, 47:1-8.

Hanauer, S. B.; Feagan, B. G.; Lichtenstein, G. R.; Mayer, L. F.; Schreiber, S.; Colombel, J. F.; Rachmilewitz, D.; Wolf, D. C.; Olson, A.; Bao, W.; Rutgeerts, P., Maintenance infliximab for Crohn's disease: the ACCENT I randomised trial. *Lancet* 2002, 359:1541-1549.

Kaser, A., Zeissig, S., Blumberg, R. S., Inflammatory bowel disease. *Annu. Rev. Immunol.* 2010, 28:573-621.

Kozuch, P. L. and Hanauer, S. B., Treatment of inflammatory bowel disease: A review of medical therapy. *World J. Gastroenterol.* 2008, 14:354-377.

Lawrance, I. C. What is left when anti-tumour necrosis factor therapy in inflammatory bowel diseases fails? *World J. Gastroenterol.* 2014, 20:1248-1258.

Mesters, J. R.; Barinka, C.; Li, W.; Tsukamoto, T.; Majer, P.; Slusher, B. S.; Konvalinka, J.; Hilgenfeld, R., Structure of glutamate carboxypeptidase II, a drug target in neuronal damage and prostate cancer. *EMBO J.* '2 2006, 25:1375-1384.

Rais, R.; Rojas, C.; Wozniak, K.; Wu, Y.; Zhao, M.; Tsukamoto, T.; Rudek, M. A.; Slusher, B. S., Bioanalytical method for evaluating the pharmacokinetics of the GCP-II inhibitor 2-phosphonomethyl pentanedioic acid (2-PMPA). *J. Pharm. Biomed. Anal.* 2014, 88:162-169.

Regueiro, M.; Siemanowski, B.; Kip, K. E.; Plevy, S., Infliximab dose intensification in Crohn's disease. *Inflamm. Bowel Dis.* 2007, 13:1093-1099.

Ristau, B. T.; O'Keefe, D. S.; Bacich, D. J., The prostate-specific membrane antigen: Lessons and current clinical implications from 20 years of research. *Urol. Oncol.* 2013, 32(3):272-9.

Sartor, R. B., Mechanisms of disease: pathogenesis of Crohn's disease and ulcerative colitis. *Nat. Clin. Pract. Gastroenterol. Hepatol.* 2006, 3:390-407.

Schreiber, S.; Khaliq-Kareemi, M.; Lawrance, I. C.; Thomsen, 0.0.; Hanauer, S. B.; McColm, J.; Bloomfield, R.; Sandborn, W. J., Maintenance therapy with certolizumab pegol for Crohn's disease. *N. Engl. J. Med.* 2007, 357: 239-250.

Schmidt, C.; Giese, T.; Hermann, E.; Zeuzem, S.; Meuer, S. C.; Stallmach, A., Predictive value of mucosal TNF-alpha transcripts in steroid-refractory Crohn's disease patients receiving intensive immunosuppressive therapy. *Inflamm. Bowel Dis.* 2007, 13:65-70.

Slusher, B. S.; Rojas, C.; Coyle, J. T., Glutamate Carboxypeptidase II. In: Rawlings and Salvesen, editors. Handbook for Proteolytic Enzymes, Academic Press. 3rd Edition. 2013, 1620-1626.

Strober, W.; Fuss, I.; and Mannon, P., The fundamental basis of inflammatory bowel disease. *J. Clin. Invest.* 2007, 117:514-521.

Thackaberry, E. A. Vehicle selection for nonclinical oral safety studies. *Expert Opin. DrugMetab. Toxicol.* 2013, 9:1635-1646.

Van, A. G.; Van, R. M.; Sciot, R.; Dubois, B.; Vermeire, S.; Noman, M.; Verbeeck, J.; Geboe, s K.; Robberecht, W.; Rutgeerts, P., Progressive multifocal leukoencephalopathy after natalizumab therapy for Crohn's disease. *N. Engl. J. Med.* 2005, 353:362-368.

Villablanca, E. J.; De, C. J.; Torregrosa, P. P.; Cassani, B.; Nguyen, D. D.; Gabrielsson, S.; Mora, J. R. beta7 integrins are required to give rise to intestinal mononuclear phagocytes with tolerogenic potential. *Gut* 2013, Sep. 12.

Xavier, R. J. and Podolsky, D. K., Unravelling the pathogenesis of inflammatory bowel disease. *Nature* 2007, 448:427-434.

Zhang, T.; Song, B.; Zhu, W.; Xu, X.; Gong, Q. Q.; Morando, C.; Dassopoulos, T.; Newberry, R. D.; Hunt, S. R.; Li, E., An ileal Crohn's disease gene signature based on whole human genome expression profiles of disease unaffected ileal mucosal biopsies. *PLoS ONE* 2012; 7:e37139.

Dutta, R. and B. D. Trapp, Pathogenesis of axonal and neuronal damage in multiple sclerosis. *Neurology*, 2007. 68 (22 Suppl 3): p. 522-31; discussion S43-54.

Calabrese, M., et al., Cortical lesions and atrophy associated with cognitiveimpairment in relapsing-remitting multiple sclerosis. *Arch Neurol*, 2009. 66 (9): p. 1144-50.

Neale, J. H., T. Bzdega, and B. Wroblewska, *N-Acetylaspartylglutamate: the most abundant peptide neurotransmitter in the mammalian central nervous system*. J Neurochem, 2000. 75 (2): p. 443-52.

Olszewski, R. T., T. Bzdega, and J. H. Neale, *mGluR3 and not mGluR2 receptors mediate the efficacy of NAAG peptidase inhibitor in validated model of schizophrenia*. Schizophr Res, 2012. 136 (1-3): p. 160-1.

Rahn, K. A., et al., *Inhibition of glutamate carboxypeptidase II (GCPII) activity as a treatment for cognitive impairment in multiple sclerosis*. Proc Natl Acad Sci USA, 2012. 109 (49): p. 20101-6.

Jablensky, A., et al., *Polymorphisms associated with normal memory variation also affect memory impairment in schizophrenia*. Genes Brain Behav, 2011. 10 (4): p. 410-7.

Egan, M. F., et al., *Variation in GRM3 affects cognition, prefrontal glutamate, and riskfor schizophrenia*. Proc Natl Acad Sci USA, 2004. 101 (34): p. 12604-9.

Harrison, P. J., et al., *The group II metabotropic glutamate receptor 3 (mGluR3, mGlu3, GRA13): expression, function and involvement in schizophrenia*. J Psychopharmacol, 2008. 22 (3): p. 308-22.

Sartorius, L. J., et al., *Expression of a GRM3 splice variant is increased in the dorsolateral prefrontal cortex of individuals carrying a schizophrenia risk SNP*. Neuropsychopharmacology, 2008. 33 (11): p. 2626-34.

Olszewski, R. T., et al., *NAAG peptidase inhibitors block cognitive deficit induced by MK-801 and motor activation induced by d-amphetamine in animal models of schizophrenia*. Transl Psychiatry, 2012. 2: p. e145.

Yamada, T., et al., *NAAG peptidase inhibition in the periaqueductal gray and rostral ventromedial medulla reduces flinching in the formalin model of inflammation*. Mol Pain, 2012. 8: p. 67.

Janczura, K. J., et al., *NAAG peptidase inhibitors and deletion of NAAG peptidase gene enhance memory in novel object recognition test*. Eur J Pharmacol, 2013. 701 (1-3): p. 27-32.

Gurkoff, G. G., et al., *NAAG peptidase inhibitor improves motor function and reduces cognitive dysfunction in a model of TBI with secondary hypoxia*. Brain Res, 2013. 1515: p. 98-107.

Cundy, K. C., et al., *Oral formulations of adefovir dipivoxil: in vitro dissolution and in vivo bioavailability in dogs*. J Pharm Sci, 1997. 86 (12): p. 1334-8.

Deeks, S. G., et al., *The safety and efficacy of adefovir dipivoxil, a novel anti-human immunodeficiency virus (HIV) therapy, in HIV-infected adults: a randomized, double-blind, placebo-controlled trial*. J Infect Dis, 1997. 176 (6): p. 1517-23.

Kearney, B. P., J. F. Flaherty, and J. Shah, *Tenofovir disoproxil fumarate: clinical pharmacology and pharmacokinetics*. Clin Pharmacokinet, 2004. 43 (9): p. 595-612.

Jaarsma, D., L. Veenma-van der Duin, and J. Korf, *N-acetylaspartate and N-acetylaspartylglutamate levels in Alzheimer's disease post-mortem brain tissue*. J Neurol Sci, 1994. 127 (2): p. 230-3.

Rowland, L. M., et al., *In vivo measurements of glutamate, GABA, and NAAG in schizophrenia*. Schizophr Bull, 2013. 39 (5): p. 1096-104.

Tsai, G. C., et al., *Reductions in acidic amino acids and N-acetylaspartylglutamate in amyotrophic lateral sclerosis CNS*. Brain Res, 1991. 556 (1): p. 151-6.

Ziehn, M. O., et al., *Hippocampal CA1 atrophy and synaptic loss during experimental autoimmune encephalomyelitis, EAE*. Lab Invest, 2010. 90 (5): p. 774-86.

Jackson, P. F., et al., *Design and pharmacological activity of phosphinic acid based NAALADase inhibitors*. J Med Chem, 2001. 44 (24): p. 4170-5.

Jackson, P. F., et al., *Design, synthesis, and biological activity of a potent inhibitor of the neuropeptidase N-acetylated alpha-linked acidic dipeptidase*. J Med Chem, 1996. 39 (2): p. 619-22.

Slusher, B. S., et al., *Selective inhibition of NAALADase, which converts NAAG to glutamate, reduces ischemic brain injury*. Nat Med, 1999. 5 (12): p. 1396-402.

Rais, R., et al., *Bioanalytical method for evaluating the pharmacokinetics of the GCP-II inhibitor 2-phosphonomethyl pentanedioic acid (2-PMPA)*. J Pharm Biomed Anal, 2013. 88: p. 162-9.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a disease or a condition, the method comprising administering to a subject in need of treatment thereof, a compound of formula (I), or a pharmaceutical composition thereof, in an amount effective for treating the disease or condition, wherein the disease or condition results in excess PSMA activity, and wherein the compound of formula (I) is:

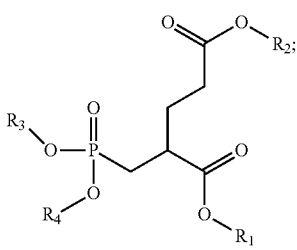
(I)

wherein:
(a) each $R_1$ is H;
    each $R_2$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)-C(=O)-NR_8R_9$;
    each $R_3$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$; and
    each $R_4$ is selected from the group consisting of $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$;

(b) each $R_1$ is alkyl;
    each $R_2$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$;
    each $R_3$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)-C(=O)-NR_8R_9$; and
    each $R_4$ is selected from the group consisting of Ar, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$;

(c) each $R_1$ is $-(CR_5R_6)_n-Ar$;
    each $R_2$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$;
    each $R_3$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$; and
    each $R_4$ is selected from the group consisting of Ar, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$; or (d) each $R_1$ is selected from Ar, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)-C(=O)-NR_8R_9$;
    each $R_2$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$;
    each $R_3$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$; and
    each $R_4$ is selected from the group consisting of H, alkyl, Ar, $-(CR_5R_6)_n-Ar$, $-(CR_5R_6)_n-O-C(=O)-R_7$, $-(CR_5R_6)_n-C(=O)-O-R_7$, $-(CR_5R_6)_n-O-C(=O)-O-R_7$, $-(CR_5R_6)_n-O-R_7$, $-(CR_5R_6)_n-O-[(CR_5R_6)_n-O]_m-R_7$, $-(CR_5R_6)_n-Ar-O-C(=O)-R_7$, $-Ar-C(=O)-O-(CR_5R_6)_n-R_7$, $-(CR_5R_6)_n-NR_8R_9$, and $-(CR_5R_6)_n-C(=O)-NR_8R_9$;

wherein:
each n is an integer from 1 to 20;
each m is an integer from 1 to 20;
each $R_5$ and $R_6$ is independently selected from the group consisting of H, alkyl, and alkylaryl;
each $R_7$ is independently straight chain or branched alkyl;
each Ar is aryl, substituted aryl, heteroaryl or substituted heteroaryl;
each $R_8$ and $R_9$ are independently H or alkyl; and
each $R_3'$ and $R_4'$ are independently H or alkyl; or
pharmaceutically acceptable salts thereof.

2. The method of claim 1, further comprising inhibiting the excess PSMA activity when the compound of formula (I), or a pharmaceutical composition thereof, is administered.

3. The method of claim 1, wherein:

$R_1$ is H;

$R_2$ and $R_3$ are each selected from the group consisting of H, —$(CR_5R_6)_n$—O—$R_7$, —$(CR_5R_6)_n$—Ar—O—C(=O)—$R_7$, —$(CR_5R_6)_n$—O—C(=O)—$R_7$, —Ar—C(=O)—O—$(CR_5R_6)_n$—$R_7$, and —$(CR_5R_6)_n$—O—C(=O)—O—$R_7$; and $R_4$ is selected from the group consisting of —$(CR_5R_6)_n$—O—$R_7$, —$(CR_5R_6)_n$—Ar—O—C(=O)—$R_7$, —Ar—C(=O)—O—$(CR_5R_6)_n$—$R_7$, —$(CR_5R_6)_n$—O—C(=O)—$R_7$ and —$(CR_5R_6)_n$—O—C(=O)—O—$R_7$; or pharmaceutically acceptable salts thereof.

4. The method of claim 1, wherein:

$R_1$ is alkyl;

$R_2$ and $R_3$ are each independently selected from the group consisting of H, alkyl, —$(CR_5R_6)_n$—O—$R_7$, —$(CR_5R_6)_n$—Ar—O—C(=O)—$R_7$, —$(CR_5R_6)_n$—O—$[(CR_5R_6)_n$—O$]_m$—$R_7$, —$(CR_5R_6)_n$—O—C(=O)—$R_7$ and —$(CR_5R_6)_n$—O—C(=O)—O—$R_7$; and $R_4$ is selected from the group consisting of —$(CR_5R_6)_n$—O—$R_7$, —$(CR_5R_6)_n$—Ar—O—C(=O)—$R_7$, —$(CR_5R_6)_n$—O—$[(CR_5R_6)_n$—O$]_m$—$R_7$, —$(CR_5R_6)_n$—O—C(=O)—$R_7$ and —$(CR_5R_6)_n$—O—C(=O)—O—$R_7$; or pharmaceutically acceptable salts thereof.

5. The method of claim 1, wherein:

$R_1$ is selected from —$(CR_5R_6)_n$—O—C(=O)—$R_7$ and —$(CR_5R_6)_n$—O—C(=O)—O—$R_7$; and $R_2$, $R_3$, and $R_4$ are each independently selected from H, Ar, —$(CR_5R_6)_n$—O—C(=O)—$R_7$, and —$(CR_5R_6)_n$—O—C(=O)—O—$R_7$; or pharmaceutically acceptable salts thereof.

6. The method of claim 1, wherein:

one of $R_1$, $R_2$, $R_3$, or $R_4$ is H and the other three are each independently selected from the group consisting of:

—$(CR_5R_6)_n$—O—C(=O)—$R_7$ and —$(CR_5R_6)_n$—O—C(=O)—O—$R_7$;

wherein $R_5$ and $R_6$ are each independently selected from the group consisting of H, $C_{1-8}$ straight-chain alkyl, and $C_{1-8}$ branched-chain alkyl;

$R_7$ is $C_{1-8}$ straight-chain alkyl, and $C_{1-8}$ branched-chain alkyl; or pharmaceutically acceptable salts thereof.

7. The method of claim 1, wherein:

$R_2$ is H; and $R_1$, $R_3$, and $R_4$ are each independently selected from the group consisting of:

—$(CR_5R_6)_n$—O—C(=O)—$R_7$ and —$(CR_5R_6)_n$—O—C(=O)—O—$R_7$;

wherein $R_5$ and $R_6$ are each independently selected from the group consisting of H, $C_{1-8}$ straight-chain alkyl, and $C_{1-8}$ branched-chain alkyl;

$R_7$ is $C_{1-8}$ straight-chain alkyl or $C_{1-8}$ branched-chain alkyl; or pharmaceutically acceptable salts thereof.

8. The method of claim 7, wherein $R_5$ and $R_6$ are each H.

9. The method of claim 1, wherein the compound of formula (I) is selected from the group consisting of:

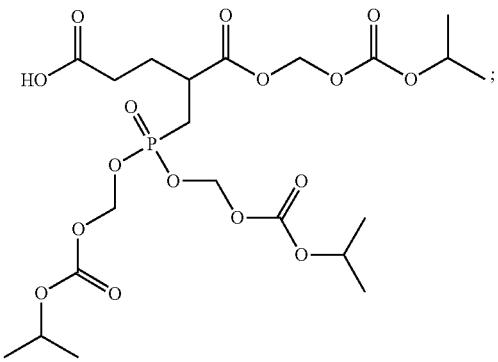

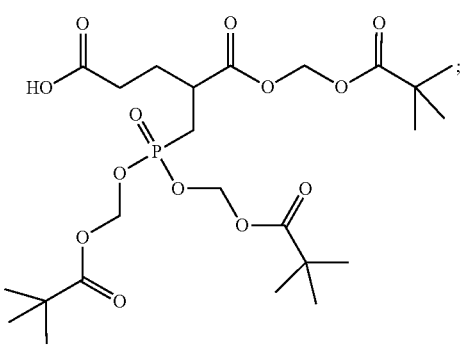

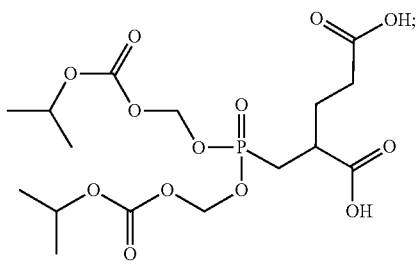

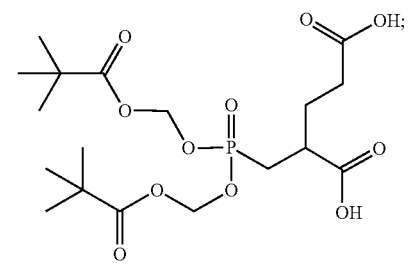

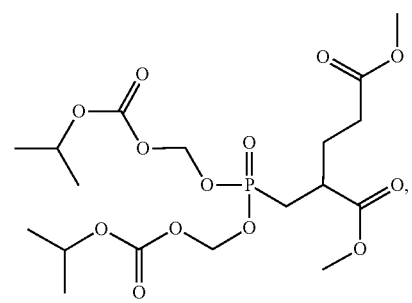

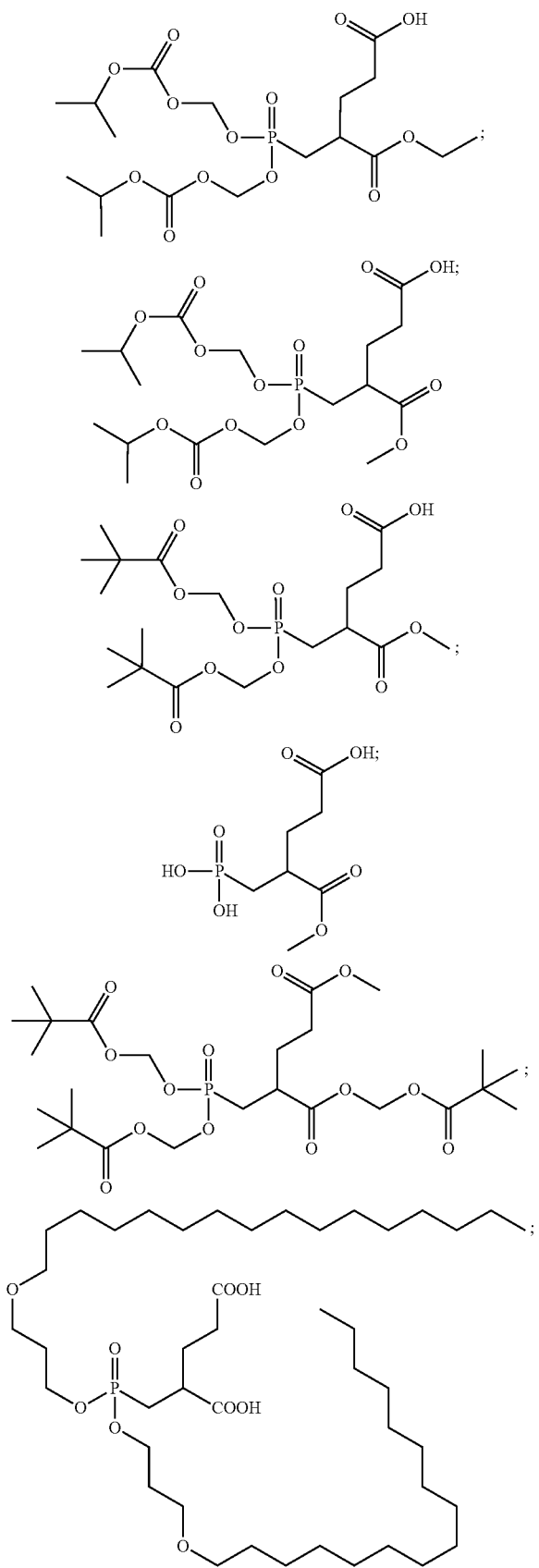
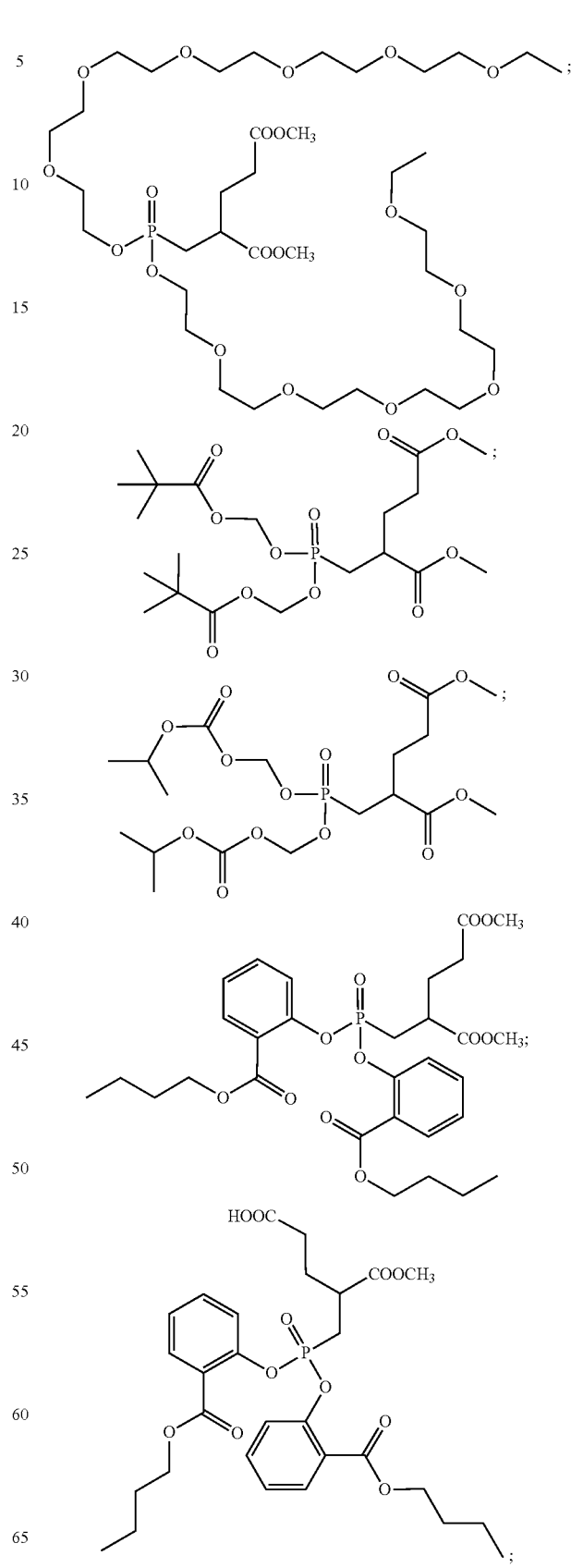

127
-continued
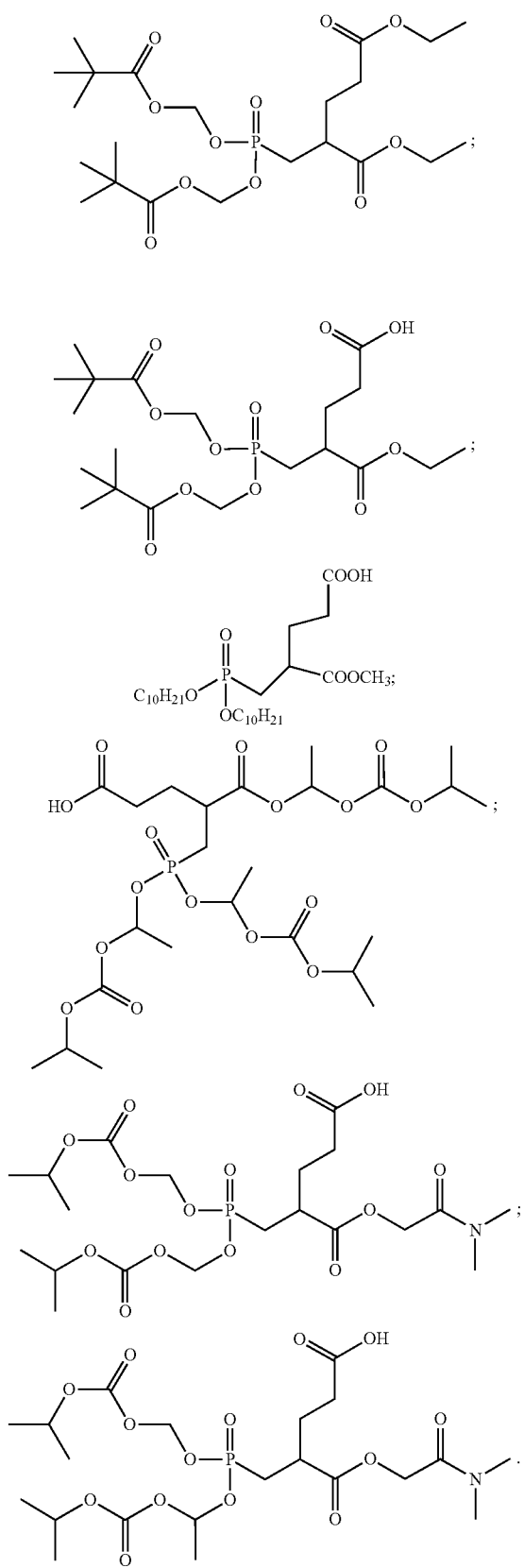
128
-continued
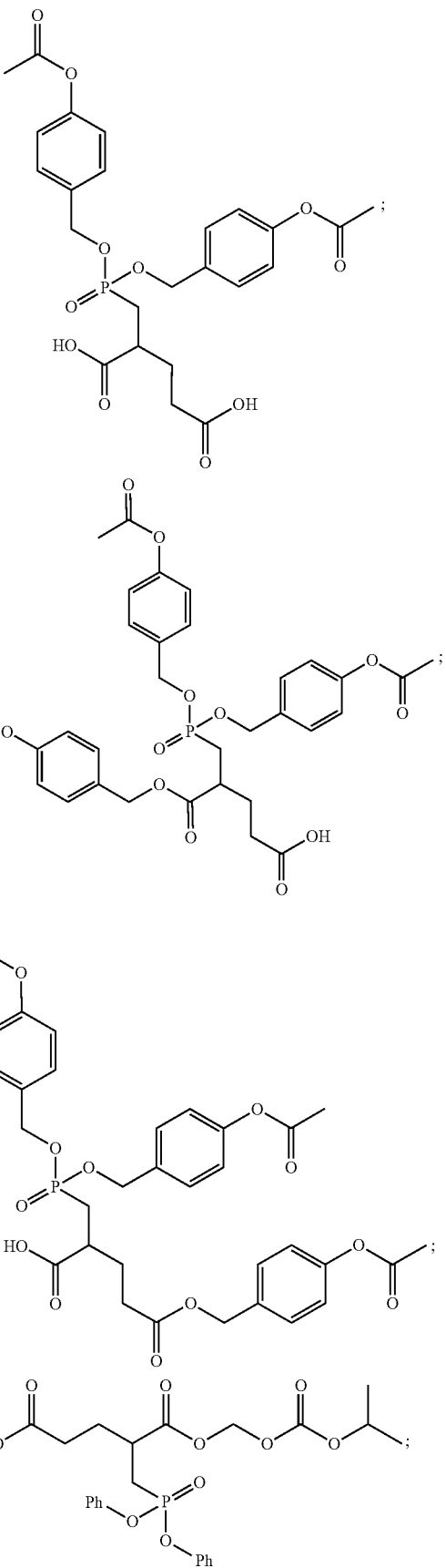

129
-continued
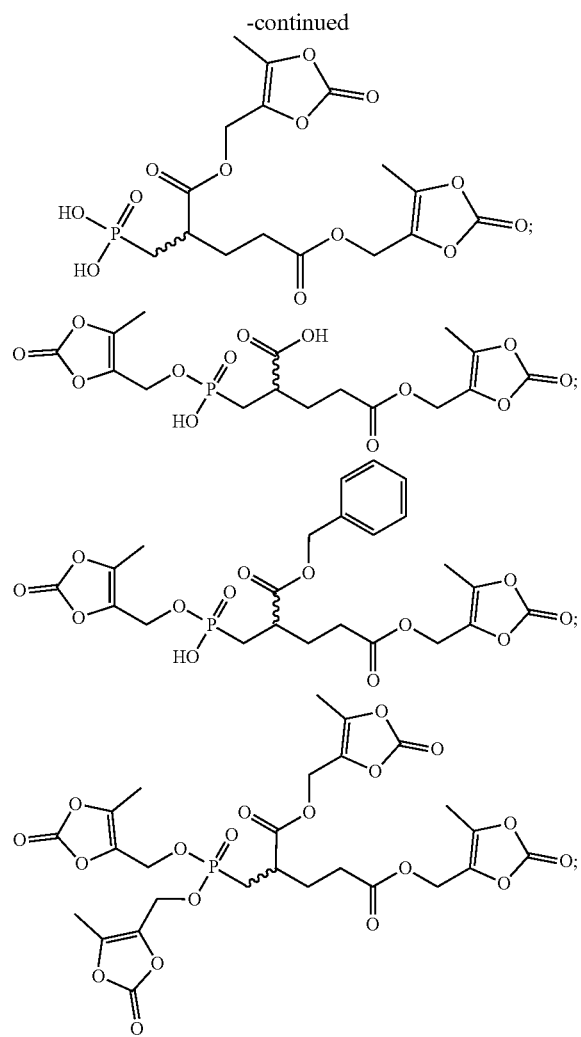
130
-continued
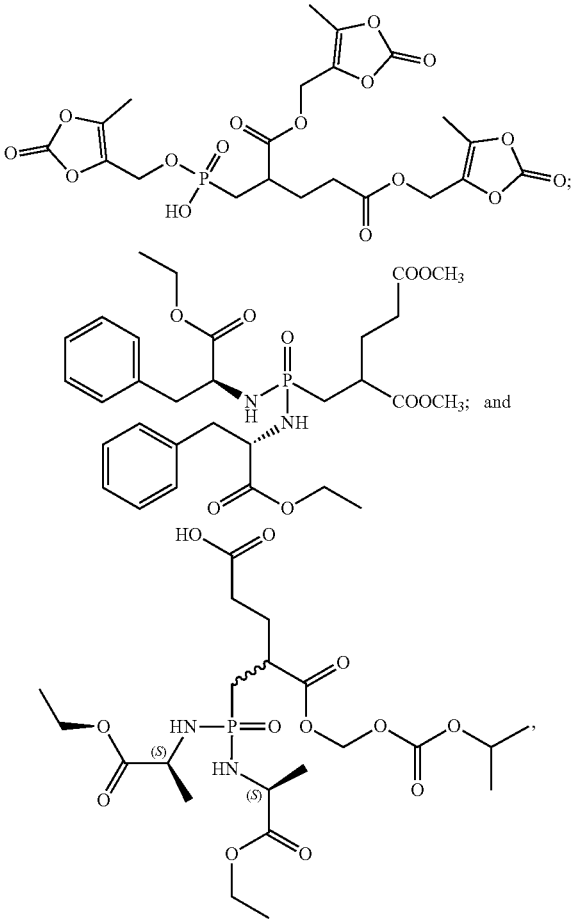
or pharmaceutically acceptable salts thereof.
* * * * *